US012691166B2

(12) United States Patent
Mirkin et al.

(10) Patent No.: US 12,691,166 B2
(45) Date of Patent: Jul. 28, 2026

(54) ANTIVIRAL VACCINES USING SPHERICAL NUCLEIC ACIDS

(71) Applicant: NORTHWESTERN UNIVERSITY, Evanston, IL (US)

(72) Inventors: Chad A. Mirkin, Wilmette, IL (US); Michelle Hope Teplensky, Evanston, IL (US); Max Everett Distler, Evanston, IL (US); Caroline Danielle Kusmierz, San Antonio, TX (US); Cassandra Elizabeth Callmann, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 1025 days.

(21) Appl. No.: 17/684,269

(22) Filed: Mar. 1, 2022

(65) Prior Publication Data

US 2022/0288181 A1    Sep. 15, 2022

Related U.S. Application Data

(60) Provisional application No. 63/250,908, filed on Sep. 30, 2021, provisional application No. 63/160,600, filed on Mar. 12, 2021.

(51) Int. Cl.
| | |
|---|---|
| *C12N 15/113* | (2010.01) |
| *A61K 39/00* | (2006.01) |
| *A61K 39/39* | (2006.01) |
| *A61P 35/00* | (2006.01) |

(52) U.S. Cl.
CPC ...... *A61K 39/001192* (2018.08); *A61K 39/39* (2013.01); *A61P 35/00* (2018.01); *C12N 15/1138* (2013.01); *A61K 2039/55555* (2013.01); *A61K 2039/55561* (2013.01)

(58) Field of Classification Search
CPC .......... A61K 39/12; A61K 2039/55555; A61K 39/39; C12N 15/1138; C12N 2770/20034
See application file for complete search history.

(56) References Cited

U.S. PATENT DOCUMENTS

| | | | |
|---|---|---|---|
| 3,687,808 A | 8/1972 | Merigan et al. |
| 4,469,863 A | 9/1984 | Ts et al. |
| 4,476,301 A | 10/1984 | Imbach et al. |
| 4,489,055 A | 12/1984 | Couvreur et al. |
| 4,845,205 A | 7/1989 | Huynh et al. |
| 4,981,957 A | 1/1991 | Lebleu et al. |
| 5,008,050 A | 4/1991 | Cullis et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,264,618 A | 11/1993 | Felgner et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |

(Continued)

FOREIGN PATENT DOCUMENTS

| | | |
|---|---|---|
| AU | 64763/98 A | 7/1998 |
| CN | 101850117 A | 10/2010 |

(Continued)

OTHER PUBLICATIONS

Agbasi-Porter et al., Transcription inhibition using oligonucleotide-modified gold nanoparticles, Bioconiugate Chem., 17(5):1178-83 (2006).

Aguilera et al., Systemic in vivo distribution of activatable cell penetrating peptides is superior to that of cell penetrating peptides, Integrative Biology, 1(5-6):371-381 (2009).

Ahmadi et al., Shape-controlled synthesis of colloidal platinum nanoparticles, Science, 272(5270):1924-6 (1996).

Akbar et al., IFN-a and IFN-ß: a link between immune memory and chronic inflammation, Immunology, 21(7):337-342 (Jul. 2000).

Akinc et al., A combinatorial library of lipid-like materials for delivery of RNAi therapeutics, Nat. Biotechnol., 26(5):561-569 (2008).

(Continued)

*Primary Examiner* — Bao Q Li
(74) *Attorney, Agent, or Firm* — MARSHALL, GERSTEIN & BORUN LLP

(57) ABSTRACT

Spherical Nucleic Acids (SNAs) are chemically well-defined nanoscale architectures comprised of nucleic acids densely arranged around a spherical nanoparticle core in a highly oriented fashion. SNAs are highly modular structures produced by chemical synthesis and programmed assembly, allowing for their rapid modification to incorporate novel viral antigens. The present disclosure provides a SNA comprising (a) a nanoparticle core; (b) a shell of oligonucleotides attached to the external surface of the nanoparticle core, the shell of oligonucleotides comprising one or more immunostimulatory oligonucleotides; and (c) a viral antigen encapsulated in the nanoparticle core.

41 Claims, 21 Drawing Sheets

Specification includes a Sequence Listing.

(56)          References Cited

U.S. PATENT DOCUMENTS

| | | | |
|---|---|---|---|
| 5,405,939 A | 4/1995 | Suhadolnik et al. | |
| 5,432,272 A | 7/1995 | Benner | |
| 5,434,257 A | 7/1995 | Matteucci et al. | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,502,177 A | 3/1996 | Matteucci et al. | |
| 5,514,785 A | 5/1996 | Van et al. | |
| 5,519,126 A | 5/1996 | Hecht | |
| 5,519,134 A | 5/1996 | Acevedo et al. | |
| 5,525,711 A | 6/1996 | Hawkins et al. | |
| 5,527,899 A | 6/1996 | Froehler | |
| 5,536,821 A | 7/1996 | Agrawal et al. | |
| 5,539,082 A | 7/1996 | Nielsen et al. | |
| 5,541,306 A | 7/1996 | Agrawal et al. | |
| 5,541,307 A | 7/1996 | Cook et al. | |
| 5,550,111 A | 8/1996 | Suhadolnik et al. | |
| 5,552,540 A | 9/1996 | Haralambidis | |
| 5,561,225 A | 10/1996 | Maddry et al. | |
| 5,563,253 A | 10/1996 | Agrawal et al. | |
| 5,565,555 A | 10/1996 | Froehler et al. | |
| 5,567,811 A | 10/1996 | Misiura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,722 A | 1/1997 | Montgomery et al. | |
| 5,594,121 A | 1/1997 | Froehler et al. | |
| 5,596,086 A | 1/1997 | Matteucci et al. | |
| 5,596,091 A | 1/1997 | Switzer | |
| 5,597,909 A | 1/1997 | Urdea et al. | |
| 5,602,240 A | 2/1997 | Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,618,704 A | 4/1997 | Sanghvi et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci et al. | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,681,941 A | 10/1997 | Cook et al. | |
| 5,700,920 A | 12/1997 | Altmann et al. | |
| 5,714,331 A | 2/1998 | Buchardt et al. | |
| 5,719,262 A | 2/1998 | Buchardt et al. | |
| 5,721,218 A | 2/1998 | Froehler | |
| 5,750,692 A | 5/1998 | Cook et al. | |
| 5,763,588 A | 6/1998 | Matteucci et al. | |
| 5,792,608 A | 8/1998 | Swaminathan et al. | |
| 5,792,747 A | 8/1998 | Schally et al. | |
| 5,814,666 A | 9/1998 | Green et al. | |
| 5,830,653 A | 11/1998 | Froehler et al. | |
| 5,955,589 A | 9/1999 | Cook et al. | |
| 6,005,096 A | 12/1999 | Matteucci et al. | |
| 6,051,698 A | 4/2000 | Janjic et al. | |
| 6,218,371 B1 | 4/2001 | Krieg et al. | |
| 6,239,116 B1 | 5/2001 | Krieg et al. | |
| 6,271,209 B1 | 8/2001 | Smith et al. | |
| 6,406,705 B1 | 6/2002 | Davis et al. | |
| 6,552,006 B2 | 4/2003 | Raz et al. | |
| 6,677,153 B2 | 1/2004 | Iversen | |
| 7,223,833 B1 | 5/2007 | Nielsen et al. | |
| 7,238,472 B2 | 7/2007 | Mirkin et al. | |
| 7,667,004 B2 | 2/2010 | Zhong et al. | |
| 7,833,992 B2 | 11/2010 | Vargeese et al. | |
| 7,893,224 B2 | 2/2011 | Manoharan et al. | |
| 8,034,376 B2 | 10/2011 | Manoharan et al. | |
| 8,148,344 B2 | 4/2012 | Akinc et al. | |
| 8,252,756 B2 | 8/2012 | Mirkin et al. | |
| 8,461,117 B2 | 6/2013 | Sufi et al. | |
| 8,507,200 B2 | 8/2013 | Mirkin et al. | |
| 8,664,407 B2 | 3/2014 | Chen et al. | |
| 8,754,062 B2 | 6/2014 | De et al. | |
| 8,791,250 B2 | 7/2014 | Nakayama et al. | |
| 8,809,292 B2 | 8/2014 | Tan et al. | |
| 8,846,080 B2 | 9/2014 | Biemans et al. | |
| 8,933,046 B2 | 1/2015 | Machuy et al. | |
| 8,940,310 B2 | 1/2015 | Barrat et al. | |
| 8,999,947 B2 | 4/2015 | Mirkin et al. | |
| 9,006,197 B2 | 4/2015 | Bumcrot et al. | |
| 9,062,310 B2 | 6/2015 | De Fougerolles et al. | |
| 9,139,827 B2 | 9/2015 | Mirkin et al. | |
| 9,376,690 B2 | 6/2016 | Mirkin et al. | |
| 9,415,109 B2 | 8/2016 | Kumar et al. | |
| 9,422,562 B2 | 8/2016 | Defougerolles et al. | |
| 9,506,056 B2 | 11/2016 | Mirkin et al. | |
| 9,687,448 B2 | 6/2017 | Akinc et al. | |
| 9,693,957 B2 | 7/2017 | Lin et al. | |
| 9,719,089 B2 | 8/2017 | Mirkin et al. | |
| 9,757,475 B2 | 9/2017 | Mirkin et al. | |
| 9,844,562 B2 | 12/2017 | Mirkin et al. | |
| 9,868,693 B2 | 1/2018 | Benenato | |
| 9,868,955 B2 | 1/2018 | Guiducci et al. | |
| 9,889,209 B2 | 2/2018 | Mirkin et al. | |
| 9,890,427 B2 | 2/2018 | Mirkin et al. | |
| 9,901,616 B2 | 2/2018 | Dhar et al. | |
| 9,950,068 B2 | 4/2018 | De et al. | |
| 9,963,700 B2 | 5/2018 | Gollob et al. | |
| 10,098,958 B2 | 10/2018 | Mirkin et al. | |
| 10,182,988 B2 | 1/2019 | Mirkin et al. | |
| 10,208,310 B2 | 2/2019 | Mader et al. | |
| 10,301,622 B2 | 5/2019 | Mirkin et al. | |
| 10,370,656 B2 | 8/2019 | Mirkin et al. | |
| 10,370,661 B2 | 8/2019 | Mirkin et al. | |
| 10,391,116 B2 | 8/2019 | Mirkin et al. | |
| 10,398,784 B2 | 9/2019 | Mirkin et al. | |
| 10,472,628 B2 | 11/2019 | De Fougerolles et al. | |
| 10,507,246 B2 | 12/2019 | Lin et al. | |
| 10,507,249 B2 | 12/2019 | Guild et al. | |
| 10,563,244 B2 | 2/2020 | Mrksich et al. | |
| 10,792,251 B2 | 10/2020 | Mirkin et al. | |
| 10,837,018 B2 | 11/2020 | Radovic-Moreno et al. | |
| 10,894,963 B2 | 1/2021 | Radovic-Moreno et al. | |
| 11,123,294 B2 | 9/2021 | Radovic-Moreno et al. | |
| 11,433,131 B2 | 9/2022 | Mirkin et al. | |
| 11,690,920 B2 | 7/2023 | Mirkin et al. | |
| 11,883,535 B2 | 1/2024 | Mirkin et al. | |
| 2002/0172711 A1 | 11/2002 | Martin et al. | |
| 2003/0026782 A1 | 2/2003 | Krieg | |
| 2003/0044354 A1 | 3/2003 | Carpenter et al. | |
| 2003/0147966 A1 | 8/2003 | Franzen et al. | |
| 2003/0170162 A1 | 9/2003 | Nayfeh et al. | |
| 2004/0014956 A1 | 1/2004 | Woolf et al. | |
| 2004/0033197 A1 | 2/2004 | Madar et al. | |
| 2004/0053384 A1 | 3/2004 | Sligar et al. | |
| 2004/0158051 A1 | 8/2004 | Ozkan et al. | |
| 2004/0170560 A1 | 9/2004 | Fossheim et al. | |
| 2004/0219565 A1 | 11/2004 | Kauppinen et al. | |
| 2005/0130167 A1 | 6/2005 | Bao et al. | |
| 2005/0232866 A1 | 10/2005 | Melchior et al. | |
| 2006/0014191 A1 | 1/2006 | Lao et al. | |
| 2006/0083781 A1 | 4/2006 | Shastri et al. | |
| 2006/0292174 A1 | 12/2006 | De et al. | |
| 2007/0243136 A1 | 10/2007 | Fisher et al. | |
| 2007/0298257 A1 | 12/2007 | Ludwig et al. | |
| 2008/0175893 A1 | 7/2008 | Huang et al. | |

(56) References Cited

U.S. PATENT DOCUMENTS

| | | |
|---|---|---|
| 2008/0181928 A1 | 7/2008 | Hakimi-Mehr et al. |
| 2008/0194463 A1 | 8/2008 | Weller et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0065822 A1 | 3/2009 | Hwang |
| 2009/0209629 A1 | 8/2009 | Mirkin et al. |
| 2009/0246142 A1 | 10/2009 | Bhatia et al. |
| 2009/0322327 A1 | 12/2009 | Gao |
| 2010/0003317 A1 | 1/2010 | Akinc et al. |
| 2010/0092486 A1 | 4/2010 | Kandimalla et al. |
| 2010/0129808 A1 | 5/2010 | Mirkin et al. |
| 2010/0136682 A1 | 6/2010 | Mirkin et al. |
| 2010/0144848 A1 | 6/2010 | Vogel et al. |
| 2010/0166842 A1 | 7/2010 | Lu et al. |
| 2010/0184844 A1 | 7/2010 | Mirkin et al. |
| 2010/0203149 A1 | 8/2010 | Radosz et al. |
| 2010/0233270 A1 | 9/2010 | Mirkin et al. |
| 2011/0020242 A1 | 1/2011 | Zheng et al. |
| 2011/0052680 A1 | 3/2011 | Hendrickson et al. |
| 2011/0052697 A1 | 3/2011 | Farokhzad et al. |
| 2011/0159081 A1 | 6/2011 | Biemans et al. |
| 2011/0223257 A1 | 9/2011 | Zhao et al. |
| 2011/0229529 A1 | 9/2011 | Irvine et al. |
| 2011/0237435 A1 | 9/2011 | Ryan |
| 2012/0149843 A1 | 6/2012 | Chien et al. |
| 2012/0244230 A1 | 9/2012 | Mirkin et al. |
| 2012/0269730 A1 | 10/2012 | Mirkin et al. |
| 2012/0282186 A1 | 11/2012 | Mirkin et al. |
| 2012/0283316 A1 | 11/2012 | Mirkin et al. |
| 2013/0028857 A1 | 1/2013 | Gao et al. |
| 2013/0089614 A1 | 4/2013 | Zhang et al. |
| 2013/0123333 A1 | 5/2013 | Mirkin et al. |
| 2013/0149374 A1 | 6/2013 | Lee et al. |
| 2013/0172404 A1 | 7/2013 | Mirkin et al. |
| 2013/0178610 A1 | 7/2013 | Mirkin et al. |
| 2013/0196951 A1 | 8/2013 | Schoenfisch et al. |
| 2013/0252852 A1 | 9/2013 | Pfeiffer et al. |
| 2013/0295129 A1 | 11/2013 | Irvine et al. |
| 2013/0309172 A1 | 11/2013 | Berlin et al. |
| 2013/0315831 A1 | 11/2013 | Shi et al. |
| 2014/0005258 A1 | 1/2014 | Mirkin et al. |
| 2014/0065425 A1 | 3/2014 | Bogdanov |
| 2014/0068429 A1 | 3/2014 | Belbin et al. |
| 2014/0086849 A1 | 3/2014 | Mckenna |
| 2014/0194493 A1 | 7/2014 | Sah et al. |
| 2014/0314739 A1 | 10/2014 | Petrovsky |
| 2015/0031745 A1 | 1/2015 | Mirkin et al. |
| 2015/0064265 A1 | 3/2015 | Fahmy et al. |
| 2015/0111790 A1 | 4/2015 | Ategeka et al. |
| 2015/0259680 A1 | 9/2015 | Mirkin et al. |
| 2015/0352138 A1 | 12/2015 | Mirkin et al. |
| 2016/0108123 A1 | 4/2016 | Freeman et al. |
| 2016/0186138 A1 | 6/2016 | Chelyapov et al. |
| 2016/0186178 A1 | 6/2016 | Radovic-Moreno et al. |
| 2016/0194642 A1 | 7/2016 | Gryaznov et al. |
| 2016/0206747 A1 | 7/2016 | Mirkin et al. |
| 2016/0237429 A1 | 8/2016 | Cubillos-Ruiz et al. |
| 2016/0274134 A1 | 9/2016 | Mutharasan et al. |
| 2016/0281086 A1 | 9/2016 | Mirkin et al. |
| 2016/0310425 A1 | 10/2016 | Mirkin et al. |
| 2017/0044544 A1 | 2/2017 | Mirkin et al. |
| 2017/0137809 A1 | 5/2017 | Mirkin et al. |
| 2017/0157048 A1 | 6/2017 | Radovic-Moreno et al. |
| 2017/0232109 A1 | 8/2017 | Mirkin et al. |
| 2018/0072810 A1 | 3/2018 | Afar et al. |
| 2018/0080058 A1 | 3/2018 | Mrksich et al. |
| 2018/0085390 A1 | 3/2018 | Mirkin et al. |
| 2018/0117175 A1 | 5/2018 | Mirkin et al. |
| 2018/0153822 A1 | 6/2018 | Karve et al. |
| 2018/0187189 A1 | 7/2018 | Mirkin et al. |
| 2018/0193484 A1 | 7/2018 | Mirkin et al. |
| 2018/0214376 A1 | 8/2018 | Giljohann |
| 2018/0222982 A1 | 8/2018 | Dranoff et al. |
| 2018/0238889 A1 | 8/2018 | Mirkin et al. |

| | | |
|---|---|---|
| 2018/0344873 A1 | 12/2018 | Mirkin et al. |
| 2019/0030185 A1 | 1/2019 | Mirkin et al. |
| 2019/0032087 A1 | 1/2019 | Cullis et al. |
| 2019/0136231 A1 | 5/2019 | Morrissey et al. |
| 2019/0225968 A1 | 7/2019 | Anderson et al. |
| 2020/0022913 A1 | 1/2020 | Mirkin et al. |
| 2020/0101156 A1 | 4/2020 | Mirkin et al. |
| 2020/0208177 A1 | 7/2020 | Watson et al. |
| 2020/0246484 A1 | 8/2020 | Mirkin et al. |
| 2020/0291394 A1 | 9/2020 | Mirkin et al. |
| 2020/0384104 A1 | 12/2020 | Mirkin et al. |
| 2021/0039062 A1 | 2/2021 | Mirkin et al. |
| 2021/0052497 A1 | 2/2021 | Mirkin et al. |
| 2021/0087221 A1 | 3/2021 | Mirkin et al. |
| 2021/0102211 A1 | 4/2021 | Radovic-Moreno et al. |
| 2021/0122778 A1 | 4/2021 | Mirkin et al. |
| 2021/0123057 A1 | 4/2021 | Mirkin et al. |
| 2021/0189397 A1 | 6/2021 | Mirkin et al. |
| 2021/0220454 A1 | 7/2021 | Mirkin et al. |
| 2021/0236651 A1 | 8/2021 | Mirkin et al. |
| 2021/0332495 A1 | 10/2021 | Mirkin et al. |
| 2022/0010302 A1 | 1/2022 | Mirkin et al. |
| 2022/0056220 A1 | 2/2022 | Mirkin et al. |
| 2022/0175956 A1 | 6/2022 | Mirkin et al. |
| 2022/0288181 A1 | 9/2022 | Mirkin et al. |
| 2022/0288225 A1 | 9/2022 | Wu |
| 2022/0348985 A1 | 11/2022 | Mirkin et al. |
| 2022/0349005 A1 | 11/2022 | Mirkin et al. |
| 2022/0364095 A1 | 11/2022 | Mirkin et al. |
| 2022/0370490 A1 | 11/2022 | Mirkin et al. |
| 2022/0387585 A1 | 12/2022 | Mirkin et al. |
| 2023/0088835 A1 | 3/2023 | Mirkin et al. |
| 2023/0147733 A1 | 5/2023 | Mirkin et al. |
| 2023/0381306 A1 | 11/2023 | Mirkin et al. |
| 2023/0382941 A1 | 11/2023 | Mirkin et al. |
| 2024/0150817 A1 | 5/2024 | Mirkin et al. |
| 2024/0165263 A1 | 5/2024 | Mirkin et al. |
| 2024/0309367 A1 | 9/2024 | Mirkin et al. |
| 2024/0318204 A1 | 9/2024 | Mirkin et al. |
| 2024/0382424 A1 | 11/2024 | Mirkin et al. |
| 2024/0398918 A1 | 12/2024 | Mirkin et al. |
| 2025/0002921 A1 | 1/2025 | Stegh et al. |

FOREIGN PATENT DOCUMENTS

| | | | |
|---|---|---|---|
| CN | 103212089 A | 7/2013 | |
| EP | 1072679 A2 | 1/2001 | |
| EP | 2162117 A2 | 3/2010 | |
| EP | 2399608 A1 | 12/2011 | |
| HK | 1152529 | 3/2012 | |
| WO | 96/33739 A1 | 10/1996 | |
| WO | 96/34876 A1 | 11/1996 | |
| WO | 97/12896 A1 | 4/1997 | |
| WO | 98/39352 A1 | 9/1998 | |
| WO | 99/14226 A2 | 3/1999 | |
| WO | 2001/062895 A2 | 8/2001 | |
| WO | 02/96262 A2 | 12/2002 | |
| WO | 03/86280 A2 | 10/2003 | |
| WO | WO-2005004907 A1 * | 1/2005 | ............. A61P 37/04 |
| WO | 2005/063201 A2 | 7/2005 | |
| WO | 2005/063288 A1 | 7/2005 | |
| WO | 2006/138145 A1 | 12/2006 | |
| WO | 2007/008463 A2 | 1/2007 | |
| WO | 2007/047455 A2 | 4/2007 | |
| WO | 2007/064857 A2 | 6/2007 | |
| WO | 2007/096134 A1 | 8/2007 | |
| WO | 2008/014979 A2 | 2/2008 | |
| WO | 2008/151022 A2 | 12/2008 | |
| WO | 2008/151049 A2 | 12/2008 | |
| WO | 2009/061515 A1 | 5/2009 | |
| WO | 2009/073984 A1 | 6/2009 | |
| WO | 2009/120887 A2 | 10/2009 | |
| WO | 2010/060110 A1 | 5/2010 | |
| WO | 2010/105209 A1 | 9/2010 | |
| WO | 2010/120420 A1 | 10/2010 | |
| WO | 2011/017456 A2 | 2/2011 | |
| WO | 2011/028850 A1 | 3/2011 | |
| WO | 2012/055933 A1 | 5/2012 | |
| WO | 2012/068470 A2 | 5/2012 | |

(56)  References Cited

FOREIGN PATENT DOCUMENTS

| WO | 2012/170930 A1 | 12/2012 |
| WO | 2013/012628 A2 | 1/2013 |
| WO | 2013/028843 A1 | 2/2013 |
| WO | 2013/049941 A1 | 4/2013 |
| WO | 2013/151771 A1 | 10/2013 |
| WO | 2014/169264 A2 | 10/2014 |
| WO | 2015/013673 A1 | 1/2015 |
| WO | 2015/013675 A1 | 1/2015 |
| WO | 2015/055630 A1 | 4/2015 |
| WO | 2015/126502 A2 | 8/2015 |
| WO | 2015/187966 A1 | 12/2015 |
| WO | 2016/028940 A1 | 2/2016 |
| WO | 2016/081911 A2 | 5/2016 |
| WO | 2016/115320 A1 | 7/2016 |
| WO | 2017/031086 A1 | 2/2017 |
| WO | 2017/035278 A1 | 3/2017 |
| WO | WO-2017075615 A1 * | 5/2017 | .......... C07K 14/005 |
| WO | 2017/136467 A1 | 8/2017 |
| WO | 2017/193081 A1 | 11/2017 |
| WO | 2018/022694 A1 | 2/2018 |
| WO | 2018/067302 A2 | 4/2018 |
| WO | 2018/152327 A1 | 8/2018 |
| WO | 2018/175445 A1 | 9/2018 |
| WO | 2018/201090 A1 | 11/2018 |
| WO | 2018/213585 A1 | 11/2018 |
| WO | 2019/032241 A1 | 2/2019 |
| WO | 2019/070890 A1 | 4/2019 |
| WO | 2019/118883 A1 | 6/2019 |
| WO | 2019/200262 A1 | 10/2019 |
| WO | 2019/217870 A1 | 11/2019 |
| WO | 2020/056341 A2 | 3/2020 |
| WO | 2020/068905 A1 | 4/2020 |
| WO | 2020/072833 A1 | 4/2020 |
| WO | 2020/118259 A1 | 6/2020 |
| WO | 2020/168005 A1 | 8/2020 |
| WO | 2020/181144 A1 | 9/2020 |
| WO | 2020/219985 A1 | 10/2020 |
| WO | 2020/257674 A1 | 12/2020 |
| WO | 2021/034956 A2 | 2/2021 |
| WO | 2021/177996 A1 | 9/2021 |
| WO | 2021/207630 A1 | 10/2021 |
| WO | 2022/155149 A1 | 7/2022 |
| WO | 2022/183043 A1 | 9/2022 |
| WO | 2022/192038 A1 | 9/2022 |
| WO | 2022/204427 A1 | 9/2022 |
| WO | 2022/212564 A1 | 10/2022 |
| WO | 2023/092040 A1 | 5/2023 |
| WO | 2023/107389 A1 | 6/2023 |

OTHER PUBLICATIONS

Akinc et al., Targeted delivery of RNAi therapeutics with endogenous and exogenous ligand-based mechanisms, Molecular therapy: the journal nfthe American Society of Gene Therapy, 18(7):1357-1364 (2010).

Akira et al., Toll-like receptor signalling, Nature Reviews Immunology, 4(1):499-511 (Jul. 2004).

Alemdaroglu et al., DNA block copolymer micelles—A combinatorial tool for cancer tanotechnology, Advanced materials, 20:899 (2008).

Alexopoulou et al., Recognition of double-stranded RNA and activation of NF-kappaB by Toll-like receptor 3, Nature, 413(1):732-738 (Oct. 2001).

Alfagih et al., Nanoparticles as Adjuvants and Nanodelivery Systems for mRNA-Based Vaccines, Pharm., 13(1):45 (2020).

Ali et al., Vaccines combined with immune checkpoint antibodies promote cytotoxic T-cell activity and tumor eradication, Cancer Immunology Research, 4(2):95-100 (2016).

Alsaiari et al., Endosomal Escape and Delivery of CRISPR/Cas9 Genome Editing Machinery Enabled by Nanoscale Zeolitic Imidazolate Framework, Journal of the American Chemical Society, 140(1):143-146 (Jan. 2018).

Altschul et al., Basic local alignment search tool, J. Mol. Biol., 215(3):403-410 (1990).

Andrews et al., Conjugation of lipid and CpG-containing oligonucleotide yields an efficient method for liposome incorporation, bioconjugate Chem., 22:1279-1286 (2011).

Arsenault et al., Combined CpG and poly I:C stimulation of monocytes results in unique signaling activation not observed with the individual ligands, Cellular Signalling, 25(11):2246-2254 (Nov. 2013).

Ashley et al., The targeted delivery of multicomponent cargos to cancer cells by nanoporous particle-supported lipid bilayers, Nat. Mater., 10:389-397 (2011).

Bachmann et al., Vaccine delivery: a matter of size, geometry, kinetics and molecular patterns, Nature Reviews Immunology, 10(11):787-796 (Oct. 2010).

Bae et al., Targeted drug delivery to tumors: myths, reality and possibility, J. Control Release, 153(3)1198-205 (2011).

Bahnemann, in Photochemical conversion and storage of solar energy (eds. Pelizetti and Schiavello, 251 (1991).

Bailey et al., Efficient encapsulation of DNA plasmids in small neutral liposomes induced by ethanol and calcium, Biochimica et Biophysica Acta (BBA)—Biomembranes, 1468(1-2): 239-252 (Sep. 2000).

Bakker, Melanocyte lineage-specific antigen gp100 in T cellmediated immunotherapy of melanoma, (1996).

Banchelli et al., Phospholipid membranes decorated by cholesterol-based oligonucleotides as soft hybrid nanostructures, J. Phys. Chem. B., 112:10942-10952 (2008).

Banga et al., Cross-linked micellar spherical nucleic acids from thermoresponsive templates, J. Am. Chem. Soc., 139(12):4278-4281 (2017).

Banga et al., Liposomal Spherical Nucleic Acids, J. Am. Chem. Soc., 136(28):9866-9869 (2014).

Barbalat et al., Nucleic Acid Recognition by the Innate Immune System, Annual Review of Immunology, 29(1):185-214 (Apr. 2011).

Barros-Martins et al., Immune responses against SARS-CoV-2 variants after heterologous and homologous ChAdOx1 nCoV-19/BNT162b2 vaccination, Nature Medicine, 27(9):1525-1529 (Sep. 2021).

Barry et al., Role of endogenous endonucleases and tissue site in transfection and CpG-mediated immune activation after naked DNA injection, Human gene therapy, 10(15):2461-2480 (Oct. 1999).

Basu et al., Temperature and salt dependence of higher order structure formation by antisense c-myc and c-myb phosphorothioate oligodeoxyribonucleotides containing tetraguanylate tracts, Nucleic Acids Res., 25:1327-1332 (1997).

Bayyurt et al., Encapsulation of two different TLR ligands into liposomes confer protective immunity and prevent tumor development, Journal of controlled release, 247(10):134-144 (Feb. 2017).

Beutler., Inferences, questions and possibilities in Toll-like receptor signalling, Nature, 430(1):257-263 (Jul. 2004).

Biju V., Chemical modifications and bioconjugate reactions of nanomaterials for sensing, imaging, drug delivery and therapy, Chemical Society Reviews, 43(3):744-764 (Jan. 2014).

Blanco et al., Principles of nanoparticle design for overcoming biological barriers to drug delivery, Nature biotechnology, 33:941-951 (2015).

Blazar et al., Synthetic unmethylated cytosine-phosphate-guanosine oligodeoxynucleotides are potent stimulators of antileukemia responses in naive and bone marrow transplant recipients, Blood, 98:1217-1225 (2001).

Borlinghaus et al., HyVolution-the smart path to confocal super-resolution, Nat. Methods, 13:i-iii (2016).

Bouderault et al., Nanoscale tools to selectively destroy cancer cells, chem. Commun., (18):2118-2120 (2008).

Boutros et al., Safety profiles of anti-CTLA-4 and anti-PD-1 antibodies alone and in combination, Nature Reviews Clinical Oncology, 13:473-486 (2016).

Brando et al., Murine immune responses to liver-stage antigen 1 protein FMP011, a malaria vaccine candidate, delivered with adjuvant AS01B or AS02A, Infection and Immunity, 75(2):838-845 (Feb. 2007).

(56) References Cited

OTHER PUBLICATIONS

Briley et al., In Nanomaterials for Biomedicine; American Chemical Society, 1119:1-20 (2012).

Brodin et al., Correction to "DNA-Mediated Cellular Delivery of Functional Enzymes", J. Am. Chem. Soc., 138(1): 459 (2016).

Brodin et al., DNA-mediated cellular delivery of functional enzymes, J. Am. Chem. Soc., 137(47):14838-14841 (2015).

Brodin et al., DNA-Mediated Cellular Delivery of Functional Enzymes, Journal of the American Chemical Society, 137(47):14838-14841 (Nov. 2015).

Brus, Quantum crystallites and nonlinear optics, Appl. Phys. A., 53:465-474 (1991).

Bunge et al., Lipophilic oligonucleotides spontaneously insert into lipid membranes, bind complementary DNA strands, and sequester into lipid-disordered domains, Langmuir, Mar. 17, 2007, vol. 23, No. 8, pp. 4455-4464.

Burgess, Liposome preparation—Avanti(Registered) Polar Lipids, Sigma-Aldrich, 3 pages (1998).

Cagdas et al., Liposomes as potential drug carrier systems for drug delivery, In Application of Nanotechnology in Drug Delivery, Chapter 1, 51 pages (2014).

Calabrese et al., Biocompatible infinite-coordination-polymer nanoparticle-nucleic-acid conjugates for antisense gene regulation, Angew. Chem. Int. Ed. Engl., 54(2):476-480 (2015).

Calllmann et al., Impact of Liposomal Spherical Nucleic Acid Structure on Immunotherapeutic Function, ACS Central Science, 7(5):892-899 (Apr. 2021).

Calllmann et al., Tumor cell lysate-loaded immunostimulatory spherical nucleic acids as therapeutics for triple-negative breast cancer, PNAS U.S.A., 117(30):17543-17550 (Jul. 2020).

Cao et al., Reversible cell-specific drug delivery with aptamer-functionalized liposomes, Angew. Chem. Int. Ed., 48:6494-6498 (2009).

Capaccioli et al., Cationic lipids improve antisense oligonucleotide uptake and prevent degradation in cultured cells and inhuman serum, Biochem. Biophys. Res. Commun., 197(2):818-825 (1993).

CDC, Adjuvants and Vaccines, URL: https://www.cdc.gov/vaccinesafety/concerns/adjuvants.html.

CDC, SARS-CoV-2 Variant Classifications and Definitions, 1-16 (May 2021), URL: https://stacks.cdc.gov/view/cdc/105817.

Cerritelli et al., PEG-SS-PPS: Reduction-Sensitive Disulfide Block Copolymer Vesicles for Intracellular Drug Delivery, Biomacromolecules, 8(6): 1966-1972 (2007).

Chen et al., Dynamic imaging of genomic loci in living human cells by an optimized CRISPR/Cas system, Cell, 155(7):1479-1491 (Dec. 2013).

Cheng et al., Dendrimer-Based Lipid Nanoparticles Deliver Therapeutic FAH mRNA to Normalize Liver Function and Extend Survival in a Mouse Model of Hepatorenal Tyrosinemia Type I, Advanced Materials, 30(52):e1805308 (2018).

Cheng et al., Selective organ targeting (SORT) nanoparticles for tissue-specific mRNA delivery and CRISPR-Cas gene editing, Nature Nanotechnology, 15:313-320 (2020).

Chien et al., DNA-nanoparticle micelles as supramolecular fluorogenic substrates enabling catalytic signal amplification and detection by DNAzyme probes, Chem. Commun., 47:167-169 (2011).

Chinen et al., Relationships between Poly(ethylene glycol) modifications on RNA-spherical nucleic acid conjugates and cellular uptake and circulation time, Bioconjugate Chemistry, 27(11):2715-2721 (2016).

Chinen et al., Spherical Nucleic Acid Nanoparticle Conjugates Enhance G-Quadruplex Formation and Increase Serum Protein Interactions, Angew. Chemie—Int. Ed., 54(2):527-531 (2015).

Chinnathambi et al., Binding mode of CpG oligodeoxynucleotides to nanoparticles regulates bifurcated cytokine induction via Toll-like receptor 9, Scientific Reports, 2(534):1-9 (2012).

Cho et al., Targeted delivery of siRNA-generating DNA nanocassettes using multifunctional nanoparticles, Small 9 (11): 1964-1973 (2013).

Cho et al., Therapeutic nanoparticles for drug delivery in cancer, Clin. Cancer Res., 14(5)11310-1316 (2008).

Choi et al., Mechanism for the endocytosis of spherical nucleic acid nanoparticle conjugates, Proc. Natl. Acad. Sci. U.S.A., 110(19):7625-7630 (2013).

Chou et al., Strategies for the intracellular delivery of nanoparticles, Chemical Society Reviews, 40(1):233-245 (Jan. 2011).

Clauson et al., The Content of CpG-DNA in Antigen-CpG Conjugate Vaccines Determines Their Cross-Presentation Activity, Bioconjug. Chem., 30(3):561-567 (2019).

Colletti et al., TLR3 Signaling Promotes the Induction of Unique Human BDCA-3 Dendritic Cell Populations, Frontiers in Immunology, 7(88):1-11 (Mar. 2016).

Collin et al., Human dendritic cell subsets: an update, Immunology, 154(1):3-20 (May 2018).

Cook, Medicinal chemistry of antisense oligonucleotides—future opportunities, Anti-Cancer Drug Design, 6(6):585-607 (1991).

Coulie et al., Tumour antigens recognized by T lymphocytes: at the core of cancer immunotherapy, Nature Reviews Cancer, 14(2):135-146 (2014).

Couvreur, Nanoparticles in drug delivery: past, present and future, Advanced drug delivery reviews, 65(1):21-23 (2013).

Curtis et al., A morphology-selective copper organosol†, Angew. Chem. Int. Ed. Engl., 27(11):1530-1533 (1988).

Cutler et al., Polyvalent nucleic acid nanostructures, J. Am. chem. Soc., 133(24)19254-9257 (2011).

Cutler et al., Polyvalent oligonucleotide iron oxide nanoparticle "click" conjugates, Nano Lett., 10(4)11477-1480 (2010).

Cutler et al., Spherical nucleic acids, J. Am. Chem. Soc., 134(3):1376-1391 (2012).

Cutrona et al., Effects in live cells of a c-myc anti-gene PNA linked to a nuclear localization signal, Nature Biotechnology, 18(3):300-303 (Mar. 2000).

Datta et al., The Therapeutic Potential of Antigen-Oligonucleotide Conjugates, Ann. N.Y. Acad. Sci., 1002(1):105-111 (2003).

Dave et al., Programmable assembly of DNA-functionalized liposomes by DNA, ACS Nano, 5(2)11304-1312 (2011).

Dearman et al., Toll-like receptor ligand activation of murine bone marrow-derived dendritic cells, Immunology, 126:475-84 (2009).

Doench et al., Optimized sgRNA design to maximize activity and minimize off-target effects of CRISPR-Cas9, Nature Biotechnology, 34(2):184-191 (Feb. 2016).

Dua et al., Liposomei Methods of Preparation and Applications, International Journal of Pharmaceutical Studies and Research, 3(2)114-20 (2012).

Dupuis et al., Distribution of adjuvant MF59 and antigen gD2 after intramuscular injection in mice, Vaccine, 18(45783):434-439 (Oct. 1999).

Düzgünes et al., Mechanisms and kinetics of liposome-cell interactions, Advanced drug delivery reviews, 40(1-2):3-18 (Nov. 1999).

Englisch et al., Angewandte Chemie, International Edition, 30:613-722 (1991).

Englisch et al., Chemically Modified Oligonucleotides as Probes and Inhibitors, Angewandte Chemie International Edition, 30(6):613-629 (Jun. 1991).

English Translation of CN 101850117 A "A Compound Immunologic Adjuvant and Vaccine." Originally Published in Chinese on Oct. 6, 2010, 6 printed pages. (Year: 2010).

Enustun et al., Coagulation of colloidal gold, J. Am. Chem. Soc., 85(21):3317-3328 (1963).

European Application No. 14883485, European Search Report and Opinion, mailed May 9, 2017.

Excler et al., Vaccine development for emerging infectious diseases, Nature Medicine, 27(4):591-600 (Apr. 2021).

Ezan et al., Pharmacokinetic studies of protein drugs: past, present and future, Advanced Drug Delivery Reviews, 65(8):1065-1073 (Jul. 2013).

Fang et al., Functionalized nanoparticles with long-term stability in biological media, Small, 5(14):1637-1641 (2009).

Farokhzad et al., Nanomedicine: developing smarter therapeutic and diagnostic modalities, Drug Delivery Rev., 58(14):1456-1459 (2006).

(56)　　　　　References Cited

OTHER PUBLICATIONS

Fattal et al., Biodegradable polyalkylcyanoacrylate nanoparticles for the delivery of oligonucleotides, J. Controlled Release, 53(1-3):137-143 (1998).

Ferrari, Cancer nanotechnology: opportunities and challenges, Nature Reviews Cancer, 5:161-171 (2005).

Ferrer et al., Dual toll-like receptor targeting liposomal spherical nucleic acids, Bioconjugate chemistry, 30(3):944-951 (Mar. 2019).

Ferrer et al., Structure-Dependent Biodistribution of Liposomal Spherical Nucleic Acids, ACS. Nano., 14(2):1682-1693 (2020).

Fillion et al., Encapsulation of DNA in negatively charged liposomes and inhibition of bacterial gene expression with fluid liposome-encapsulated antisense oligonucleotides, Biochimica et Biophysica Acta (BBA)—Biomembranes, 1515(1):44-54 (Nov. 2001).

Forster, Zwischenmolekulare Energiewanderung und Fluoreszenz, Annalen der Physik, 437:55-75 (2006).

Freier et al., The ups and downs of nucleic acid duplex stability: structure-stability studies on chemically-modified DNA:RNA duplexes, Nucleic Acids Research, 25(22):4429-4443 (1997).

Frey et al., Bionanotechnology for vaccine design, Current opinion in biotechnology, 52:80-88 (2018).

Fu et al., High-frequency off-target mutagenesis induced by CRISPR-Cas nucleases in human cells, Nature Biotechnology, 31(9):822-826 (Sep. 2013).

Gilbert et al., CRISPR-mediated modular RNA-guided regulation of transcription in eukaryotes, Cell, 154(2):442-451 (Jul. 2013).

Gilbert et al., Genome-Scale CRISPR-Mediated Control of Gene Repression and Activation, Cell, 159(3):647-661 (Oct. 2014).

Giljohann et al., Gene regulation with polyvalent siRNA-nanoparticle conjugates, J. Am. Chem. Soc., 131 (6):2072-2073 (2009).

Giljohann et al., Oligonucleotide loading determines cellular uptake of DNA-modified gold nanoparticles, Nano Letters, 7(12):3818-3821 (2007).

Giljohann et al., Oligonucleotide loading determines cellular uptake of DNA-modified gold nanoparticles, Nano Letters, 7(12):3818-3821 (Dec. 2007).

Golden et al., Human angiotensin-converting enzyme 2 transgenic mice infected with SARS-CoV-2 develop severe and fatal respiratory disease, JCI Insight, 5(19):e142032(1-14) (Oct. 2020).

Grijalva et al., Oligonucleotide delivery: a patent review (2010-2013), Expert Opin. Ther. Pat., 24(7):801-819 (2014).

Gu et al., Biomaterials and emerging anticancer therapeutics: engineering the microenvironment, Nature Reviews Cancer, 16:56-66 (2016).

Guan et al., Impact of sequence specificity of spherical nucleic acids on macrophage activation in vitro and in vivo, Molecular pharmaceutics, 16(10):4223-4229 (2019).

Guan et al., RNA-Based Immunostimulatory Liposomal Spherical Nucleic Acids as Potent TLR7/8 Modulators, Small, 14:e1803284 (2018).

Gulley et al., Avelumab (MSB0010718C), an anti-PD-L1 antibody, in advanced NSCLC patients: A phase 1b, open-label expansion trial in patients progressing after platinum-based chemotherapy, Journal of Clinical Oncology, 33(15):8034-8034 (2015).

Gunnarsson et al., Liposome-based chemical barcodes for single molecule DNA detection using imaging mass soectrometry, Nano. Lett., 10:732-737 (2010).

Gunnarsson et al., Single-molecule detection and mismatch discrimination of unlabeled DNA targets, Nano Lett., 8:183-188 (2008).

Gupta et al., Expanding the genetic editing tool kit: ZFNs, TALENs, and CRISPR-Cas9, The Journal of Clinical Investigation, 124(10):4154-4161 (Oct. 2014).

Hafner et al., Particulate formulations for the delivery of poly(I:C) as vaccine adjuvant, Advanced Drug Delivery Reviews, 65(10):1386-1399 (Oct. 2013).

Hajj et al., Tools for Translation: Non-Viral Materials for Therapeutic MRNA Delivery. Nature Reviews Materials, 2:17056 (2017).

Hanagata, Structure-dependent immunostimulatory effect of CpG oligodeoxynucleotides and their delivery system, Int. J. Nanomedicine, 7:2181-2195 (2012).

Harrington et al., A thermostable Cas9 with increased lifetime in human plasma, Nature Communications, 8(1424):1-8 (Nov. 2017).

Hassler et al., A novel soluble ACE2 protein totally protects from lethal disease caused by SARS-CoV-2 infection, BioRXiv, 1-24 (Mar. 2021).

Hatakeyama et al., Development of a novel systemic gene delivery system for cancer therapy with a tumor-specific cleavable PEG-lipid, Gene Ther., 14(1)68-77 (2006).

Hayashi, Ultrafine particles, J. Vac. Sci. Technol., 5(4):1375-1384 (1987).

Hayashi, Ultrafine Particles, Physics Today, 44-60 (1987).

Hayes, Oliver G., Janet R. McMillan, Byeongdu Lee, and Chad A. Mirkin. "DNA-encoded protein Janus nanoparticles." Journal of the American Chemical Society 140, No. 29 (2018): 9269-9274.

He et al., Synergy of CpG oligodeoxynucleotide and double-stranded RNA (poly I:C) on nitric oxide induction in chicken peripheral blood monocytes, Molecular Immunology, 44(12):3234-3242 (May 2007).

Heil et al., Species-Specific Recognition of Single-Stranded RNA via Toll-like Receptor 7 and 8, Science, 303 (5663):1526-1529 (Mar. 2004).

Heinz et al., Species-specific Regulation of Toll-like Receptor 3 Genes in Men and Mice, Journal of Biological Chemistry, 278(24):21502-21509 (Jun. 2003).

Heit et al., CpG-DNA Aided Cross-Priming by Cross-Presenting B Cells, J. Immunol., 172(3):1501-1507 (2004).

Heit et al., Protective CD8 T Cell Immunity Triggered by CpG-Protein Conjugates Competes with the Efficacy of Live Vaccines, J. Immunol., 174(7):4373-4380 (2005).

Hemmi et al., A Toll-like receptor recognizes bacterial DNA, Nature, 408(1):740-745 (Dec. 2000).

Henglein et al., Absorption spectrum and some chemical reactions of colloidal platinum in aqueous solution, J. Phys. Chem., 99(38):14129-14136 (1995).

Henglein, Mechanism of reactions on colloidal microelectrodes and size quantization effects, Top. Curr. Chem., 143:113-180 (1988).

Henglein, Small-particle research: physicochemical properties of extremely small colloidal metal and semiconductor particles, Chem. Rev., 89(8):1861-1873 (1989).

Herbath et al., Coadministration of Antigen-Conjugated and Free CpG: Effects of in Vitro and in Vivo Interactions in a Murine Model, Immunol. Lett., 160(2):178-185 (2014).

Hirosue et al., Antigen Delivery to Dendritic Cells by Poly(Propylene Sulfide) Nanoparticles with Disulfide Conjugated Peptides: Cross-Presentation and T Cell Activation, Vaccine 28(50):7897-7906 (2010).

HogenEsch et al., Optimizing the utilization of aluminum adjuvants in vaccines: you might just get what you want, NPJ Vaccines, 3(51):1-11 (Oct. 2018).

Hope et al., Generation of multilamellar and unilamellar phospholipid vesicles, Chemistry and Physics of Lipids, 40:89-107(1986).

Hope et al., Production of large unilamellar vesicles by a rapid extrusion procedure: characterization of size distribution, trapped volume and ability to maintain a membrane potential, Biochim Biophys Acta, Jan. 10, 1985, vol. 812, No. 1, pp. 55-65.

Horvath et al., CRISPR/Cas, the immune system of bacteria and archaea, Science, 327(5962):167-170 (Jan. 2010).

Houot et al., T-cell modulation combined with intratumoral CpG cures lymphoma in a mouse model without the need for chemotherapy, Blood, 113(15):3546-3552 (2009).

Hsu et al., Development and applications of CRISPR-Cas9 for genome engineering, Cell, 157(6):1262-1278 (Jun. 2014).

Hu et al., Elucidating the impact of traceless conjugation chemistry on the immunostimulatory efficacy of protein spherical nucleic acids, Northwestern Int. Ins. For Nano., (2019).

Hu et al., Impact of protein spherical nucleic acid design parameters on immunostimulation, Northwestern Int. Ins. For Nano., (2020).

Huang et al., Sequence Multiplicity within Spherical Nucleic Acids, ACS Nano, 14(1):1084-1092 (Jan. 2020).

(56)            References Cited

OTHER PUBLICATIONS

Huang et al., Synergistic Immunostimulation through the Dual Activation of Toll-like Receptor 3/9 with Spherical Nucleic Acids, ACS Nano, 15(8):13329-13338 (Jul. 2021).

Huff., The Airyscan detector from ZEISS: confocal imaging with improved signal-to-noise ratio and super-resolution, Nature Methods, 12(1):i-ii (Dec. 2015).

Hurst et al., Maximizing DNA loading on a range of gold nanoparticle sizes, Anal. chem., 78(24):8313-8318 (2006).

International Application No. PCT/US2022/017984, Invitation to Pay Additional Fees, mailed May 9, 2022.

International Application No. PCT/US2022/018384, International Preliminary Report on Patentability, mailed Sep. 21, 2023.

International Application No. PCT/US18/65765, International Preliminary Report on Patentability, mailed Jun. 25, 2020.

International Application No. PCT/US18/65765, International Search Report and Written Opinion, mailed Mar. 14, 2019.

International Application No. PCT/US2018/054221, International Preliminary Report on Patentability, mailed Apr. 16, 2020.

International Application No. PCT/US2018/054221, International Search Report and Written Opinion, mailed Dec. 26, 2018.

International Application No. PCT/US2022/012023, International Preliminary Report on Patentability, mailed Jul. 27, 2023.

International Application No. PCT/US2022/012023, International Search Report and Written Opinion, mailed Mar. 29, 2022.

International Application No. PCT/US2022/017984, International Preliminary Report on Patentability, mailed Sep. 7, 2023.

International Application No. PCT/US2022/017984, International Search Report and Written Opinion, mailed Jul. 14, 2022.

International Application No. PCT/US2022/018384, International Search Report and Written Opinion, mailed Jun. 17, 2022.

International Preliminary Report on Patentability, United States Patent Office, PCT/US2014/068429, dated Jun. 7, 2016.

International Search Report and Written Opinion of the International Search Authority, United States Patent Office, PCT/US2014/068429, dated Aug. 10, 2015.

Irvine et al., Engineering synthetic vaccines using cues from natural immunity, Nature materials, 12:978-990 (2013).

Irvine et al., Synthetic nanoparticles for vaccines and immunotherapy, Chemical reviews, 115(19):11109-11146 (2015).

Irvine, Drug delivery: One nanoparticle, one kill. Nat. Mater., 10:342 (2011).

Jahn et al., Microfluidic directed formation of liposomes of controlled size, Langmuir, 23(11):6289-6293 (2007).

Jakobsen et al., Assembly of liposomes controlled by triple helix formation, Bioconjugate Chem., 24:1485-1495 (2013).

Jayaraman et al., Maximizing the Potency of SiRNA Lipid Nanoparticles for Hepatic Gene Silencing in Vivo, Angew. Chemie—Int. Ed., 51(34):8529-8533 (2012).

Jeffs et al., A Scalable, Extrusion-Free Method for Efficient Liposomal Encapsulation of Plasmid DNA, Pharmaceutical Research, 22(3):362-372 (Mar. 2005).

Jennifer Doudna lab, Expression plasmid for Cas9 from Geobacillus stearothermophilus with an N-Term MBP and SV40 Nls, synthetic DNA construct, GeoCas9 Plasmids, 1-6 (May 2011).

Jennifer Martinez, Xiaopei Huang, and Yiping Yang. "Toll-like receptor 8-mediated activation of murine plasmacytoid dendritic cells by vaccinia viral DNA." Proceedings of the National Academy of Sciences, vol. 107, No. 4, Apr. 6, 2010, pp. 6442-6447 and one supplemental page. (Year: 2010).

Jensen et al., Spherical Nucleic Acid Nanoparticle Conjugates as an RNAi-Based Therapy for Glioblastoma, Sci. Transl. Med., 5(209):209ra152 (2013).

Jiang et al., Tumor imaging by means of proteolytic activation of cell-penetrating peptides, Proc. Natl. Acad. Sci. U.S. A., 101(51):17867-17872 (2004).

Jin et al., What controls the melting properties of DNA-linked gold nanoparticle assemblies?, J. Am. Chem. Soc., 125:1643-54 (2003).

Jinek et al., A programmable dual-RNA-guided DNA endonuclease in adaptive bacterial immunity, Science, 337(6096):816-821 (Aug. 2012).

Jones et al., Programmable materials and the nature of the DNA bond, Science, 347(6224):1260901 (2015).

Jones et al., Releasable Luciferin Transporter Conjugates: Tools for the Real-Time Analysis of Cellular Uptake and Release, J. Am. Chem. Soc., 128(20):6526-6527 (2006).

June et al., The B7 and CD28 receptor families, Immunology today, 15(7):321-331 (Jul. 1994).

Kadowaki et al., Subsets of human dendritic cell precursors express different toll-like receptors and respond to different microbial antigens, The Journal of experimental medicine, 194(6):863-870 (Sep. 2001).

Kandimalla et al., Secondary structures in CpG oligonucleotides affect immunostimulatory activity, Biochemical and Biophysical Research Communications, 306:948-953 (2003).

Kanekiyo et al., Self-assembling influenza nanoparticle vaccines elicit broadly neutralizing H1N1 antibodies, Nature, 499(7456):102-106 (Jul. 2013).

Kapadia et al., Reduction Sensitive PEG Hydrogels for Codelivery of Antigen and Adjuvant to Induce Potent CTLs, Mol. Pharm., 13(10):3381-3394 (2016).

Kapadia et al., Spherical Nucleic Acid Nanoparticles: Therapeutic Potential, BioDrugs, 32:297-309 (2018).

Kasuya et al., Bio-nanocapsule-liposome conjugates for in vivo pinpoint drug and gene delivery, Methods Enzymol., 464:147-166 (2009).

Katz S., The Reversible Reaction of Sodium Thymonucleate and Mercuric Chloride, Journal of the American Chemical Society, 74(9):2238-2245 (May 1992).

Katz, The Reversible Reaction of Sodium Thymonucleate and Mercuric Chloride, J. Am. Chem. Soc., 74(9):2238-2245 (1952).

Kelly et al., Targeted liposomal drug delivery to monocytes and macrophages, Journal of Drug Delivery, Article ID 727241:1-11 (2011).

Kelty et al., High-throughput synthesis and characterization of nanocrystalline porphyrinic zirconium metal-organic frameworks, Chem. Commun(Camb), 52(50):7854-7857 (2016).

Kemp et al., "Combo" nanomedicine: Co-delivery of multi-modal therapeutics for efficient, targeted, and safe cancer therapy, Advanced Drug Delivery Reviews, 98:3-18 (2016).

Kennedy et al., Multiple roles for CD4 T cells in anti-tumor immune responses, Immunological Reviews, 222(1):129-144 (2008).

Kerkmann et al., Spontaneous Formation of Nucleic Acid-based Nanoparticles Is Responsible for High Interferon-a Induction by CpG-A in Plasmacytoid Dendritic Cells, J. Biol. Chem., 280:8086-8093 (2005).

Khalil et al., The future of cancer treatment: immunomodulation, CARs and combination immunotherapy, Nature reviews Clinical oncology, 13:273-290 (2016).

Kim et al., Cationic solid lipid nanoparticles reconstituted from low density lipoprotein components for delivery of siRNA, Mol. Pharm., 5(4):622-631 (2008).

Kim et al., Effect of bovine serum albumin on the stability of methotrexate-encapsulated liposomes, Arch. Pharmacal Res., 14:336-341 (1991).

Kim et al., Transmutable nanoparticles with reconfigurable surface ligands, Science, 351:579-582 (2016).

Klebanoff et al., CD8+ T-cell memory in tumor immunology and immunotherapy, Immunological Reviews, 211(1):214-224 (2006).

Kleinstiver et al., High-fidelity CRISPR-Cas9 nucleases with no detectable genome-wide off-target effects, Nature, 529 (7587):490-495 (Jan. 2016).

Klinman, Immunotherapeutic uses of CpG oligodeoxynucleotides, Nat. Rev. Immunol., 4:249-259 (2004).

Koshy et al., Biomaterials for enhancing anti-cancer immunity, Current opinion in biotechnology, 40:1-8 (2016).

Kosturko et al., The crystal and molecular structure of a 2:1 complex of 1-methylthymine-mercury (II), Biochemistry, 13(19):3949-3952 (1974).

(56)         References Cited

OTHER PUBLICATIONS

Kramer et al., Comparative Study of 5'- and 3'-Linked CpGAntigen Conjugates for the Induction of Cellular Immune Responses, ACS Omega, 2(1):227-235 (2017).

Kramer et al., Intracellular Cleavable CpG Oligodeoxynucleotide-Antigen Conjugate Enhances Anti-Tumor Immunity, Mol. Ther., 25(1):62-70 (2017).

Kreig, Toll-like receptor 9 (TLR9) agonists in the treatment of cancer, Oncogene, 27:116-167 (2008).

Kreutz et al., Antibody-Antigen-Adjuvant Conjugates Enable Co-Delivery of Antigen and Adjuvant to Dendritic Cells in Cis but Only Have Partial Targeting Specificity, PLoS One, 7(7):e40208 (2012).

Krieg et al., CpG motifs in bacterial DNA trigger direct B-cell activation, Nature, 374(1):546-549 (Apr. 1995).

Krieg, Development of TLR9 agonists for cancer therapy, J. Clin. Invest., 117(5):1184-1194 (2007).

Krieg, Therapeutic potential of Toll-like receptor 9 activation, Nat. Rev. Drug Discov., 5:471-484 (2006).

Kroschwitz, Concise Encyclopedia of Polymer Science and Engineering, John Wiley & Sons, 858-859 (1990).

Kukowska-Latallo et al., Efficient transfer of genetic material into mammalian cells using Starburst polyamidoamine dendrimers, Proc. Natl. Acad. Sci. USA, 93(10):4897-4902 (1996).

Kulkarni et al., Mmp-9 responsive PEG cleavable nanovesicles for efficient delivery of chemotherapeutics to pancreatic cancer, Molecular Pharmaceutics, 11(7):2390-2399 (2014).

Kusmierz et al., Defining the Design Parameters for in Vivo Enzyme Delivery Through Protein Spherical Nucleic Acids, ACS Central Science, 6(5):815-822 (Apr. 2020).

Lancaster et al., The physiological regulation of toll-like receptor expression and function in humans, J. Physiol., 563:945-955 (2005).

Laouini et al., Preparation, characterization and applications of liposomes: state of the art, Journal of colloid science and biotechnology, 1:148-168 (2012).

Laramy et al., ACS Nano, 13(2):1412 (2019).

Lau et al., Neutralizing antibody titres in SARS-CoV-2 infections, Nature Communications, 12(63):1-7 (Jan. 2021).

Lee et al., Imageable Antigen-Presenting Gold Nanoparticle Vaccines for Effective Cancer Immunotherapy In vivo, Angewandte Chemie International Edition, 51(35):8800-8805 (2012).

Lee et al., Induction of Potent Antigen-specific Cytotoxic T Cell Response by PLGA-nanoparticles Containing Antigen and TLR Agonist, Immunel. Netw., 13(1):30-33 (2013).

Lee et al., Silver nanoparticle-oligonucleotide conjugates based on DNA with triple cyclic disulfide moieties, Nano Lett., 7(7):2112-2115 (2007).

Lee et al., Trafficking of endosomal Toll-like receptors, Trends Cell Biol., 24(6):360-369 (2014).

Leonard et al., The TLR3 signaling complex forms by cooperative receptor dimerization, PNAS U.S.A., 105(1):258-263 (Jan. 2008).

Lesieur et al., Size analysis and stability study of lipid vesicles by high-performance gel exclusion chromatography, turbidity, and dynamic light scattering, Analytical Biochemistry, 192(2):334-343 (1991).

Li et al., Combination Delivery of Antigens and CpG by Lanthanides-Based Core-Shell Nanoparticles for Enhanced Immune Response and Dual-Mode Imaging, Advanced Healthcare Materials, 2(10):1309-1313 (2013).

Li et al., Induction of Interleukin-22 (IL-22) production in CD4+ T Cells by IL-17A Secreted from CpG-Stimulated Keratinocytes, Annals of Dermatology, 28(5): 579-585 (Sep. 2016).

Li et al., Materials based tumor immunotherapy vaccines, Current Opinion in Immunology, 25(2):238-245 (2013).

Li et al., Molecular spherical nucleic acids, PNAS, 115(17):4340-4344 (2018).

Li et al., Nucleolin-targeting liposomes guided by aptamer AS1411 for the delivery of siRNA for the treatment of malignant melanomas, Biomaterials, 35(12):3840-3850 (2014).

Li et al., Polymer- and lipid-based nanoparticle therapeutics for the treatment of liver diseases, Nano Today 5 (4):296-312 (2010).

Li et al., Reversible and Chemically Programmable Micelle Assembly with DNA Block-Copolymer Amphiphiles, Nano Lett., 4(6):1055-1058 (2004).

Li et al., Smart asymmetric vesicles with triggered availability of inner cell-penetrating shells for specific intracellular drug delivery, ACS Appl. Mater. Interfaces, 9(21):17727-17735 (2017).

Li et al., Synthesis of nanocrystals of Zr-based metal-organic frameworks with csq-net: significant enhancement in the degradation of a nerve agent simulant, Chem. Commun., 51(54):10925-10928 (2015).

Li et al., Thermal stability of DNA functionalized gold nanoparticles, Bioconjugate chem., 24:1790-1797 (2013).

Liang et al., Aptamer-functionalized lipid nanoparticles targeting osteoblasts as a novel RNA interference-based bone anabolic strategy, Nat. Med., 21(3): 288-294 (2015).

Lin et al., Gold Nanoparticle Delivery of Modified CpG Stimulates Macrophases and Inhibits Tumor Growth for Enhanced Immunotherapy, PLOS One, 8(5):e63550 (2013).

Liu et al., DNA-based micelles: synthesis, micellar properties and size-dependent cell permeability, Chemistry, 16:3791-3797 (2010).

Liu et al., Encapsulation of Poly I:C and the natural phosphodiester CpG ODN enhanced the efficacy of a hyaluronic acid-modified cationic lipid-PLGA hybrid nanoparticle vaccine in TC-1-grafted tumors, International Journal of Pharmaceutics, 553(1-2):327-337 (Dec. 2018).

Liu et al., Freezing directed construction of Bio/Nano interfaces: reagentless conjugation, Denser spherical nucleic acids, and better nanoflares, J. Am. Chem. Soc., 139(28): 9471-9474 (2017).

Liu et al., Membrane anchored immunostimulatory oligonucleotides for in vivo cell modification and localized immunotherapy, Angew. Chem. Int. Ed. Engl., 50(31):7052-7055 (2011).

Liu et al., New poly(d-glucaramidoamine)s induce DNA nanoparticle formation and efficient gene delivery into mammalian cells, J. Am. Chem. Soc., 126(24):7422-7423 (2004).

Liu et al., Silica nanoparticle supported lipid bilayers for gene delivery, chem. Commun., 5100-5102 (2009).

Liu et al., Structural Basis of Toll-Like Receptor 3 Signaling with Double-Stranded RNA, Science, 320(5874): 379-381 (Apr. 2008).

Lokugamage et al., Constrained nanoparticles deliver siRNA and sgRNA to T cells in vivo without targeting ligands, Advanced Materials, 31(41):e1902251 (2019).

Love et al., Lipid-like Materials for Low-Dose, in Vivo Gene Silencing, Proc. Natl. Acad. Sci., 107(5):1864-1869 (2010).

Lu et al., Bioresponsive materials, Nature Reviews Materials, 2:16075 (Oct. 2016).

Lundgren et al., Role of spectral counting in quantitative proteomics, Expert Review of Proteomics , 7(1):39-53 (Jan. 2014).

Luo et al., A STING-activating nanovaccine for cancer immunotherapy, Nature nanotechnology, 12(7):648-654 (Apr. 2017).

Lytton-Jean et al., Highly Cooperative Behavior of Peptide Nucleic Acid Linked DNA Modified Gold Nanoparticle and Combo Polymer Aggregates, Advanced Materials, 21(6):706-709 (2009).

Ma et al., Reductively Responsive Hydrogel Nanoparticles with Uniform Size, Shape, and Tunable Composition for Systemic Sirna Delivery in Vivo, Mol. Pharm., 12(10):3518-3526 (2015).

Macfarlane et al., Nanoparticle Superlattice Engineering with DNA, Science, 334:(6053):204-208 (2011).

Madaan et al., A stepwise procedure for isolation of murine bone marrow and generation of dendritic cells, Journal of Biological Methods, 1:e1 (2014).

Maier et al., Biodegradable Lipids Enabling Rapidly Eliminated Lipid Nanoparticles for Systemic Delivery of RNAi Therapeutics, Mol. Ther., 21(8):1570-1578 (2013).

Majer et al., Nucleic acid-sensing TLRs: trafficking and regulation, Curr Opin Immunol., 44(1):26-33 (Feb. 2017).

Mammadov et al., Virus-like nanostructures for tuning immune response, Sci. Rep., 5(16728):1-15 (2015).

Manders et al., Dynamics of threedimensional replication patterns during the S-phase, analysed by double labelling of DNA and confocal microscopy, J. Cell Sci., 103:857-862 (1992).

Manders et al., Measurement of co-localization of objects in dual-colour confocal images, J. Microsc., 169:375-382 (1993).

(56) References Cited

OTHER PUBLICATIONS

Mangsbo et al., Enhanced Tumor Eradication by Combining CTLA-4 or PD-1 Blockage with CpG Therapy, Journal of Immunotherapy, 33(3)1225-235 (2010).

Manson et al., Polyethylene glycol functionalized gold nanoparticles: the influence of capping density on stability in various media, Gold Bulletin, 44(2):99-105 (2011).

Marinakos et al., Gold nanoparticles as templates for the synthesis of hollow nanometer-sized conductive polymer capsules, Adv. Mater., 11(1):34-37 (1999).

Marinakos et al., Template synthesis of one-dimensional Au, Au-poly(pyrrole), and poly(pyrrole) nanoparticle arrays, Chem. Mater., 10(5):1214-19 (1998).

Marston et al., Emerging viral diseases: confronting threats with new technologies, Science Translation Medicine, 6(253):253ps 10 (Sep. 2014).

Martin et al., Ein neuer Zugang zu 2'-O-Alkylribonucleosiden und Eigenschaften deren Oligonucleotide, Helv. Chim. Acta, 78(2):486-504 (1995).

Martin et al., Ein neur Zugang zu 2'-O-alkylribonucleosiden and Eigenschaften deren oligonucleotide, Hely. Chim. Acta., 78:486-504 (1995).

Martin P., Ein neuer Zugang zu 2'-O-Alkylribonucleosiden und Eigenschaften deren Oligonucleotide, Helvetica, 78(2):486-504 (Mar. 1995).

Massart, Preparation of aqueous magnetic liquids in alkaline and acidic media, IEEE Transactions on Magnetics, 17(2):1247-1248 (1981).

Massich et al., Regulating Immune Response Using Polyvalent Nucleic Acid-Gold Nanoparticle Conjugates, Molecular Pharmaceutics, 6(6):1934-1940 (2009).

Matijevic et al., Fine Particles Part II: Formation Mechanisms and Applications, MRS Bulletin, 16-47 (1990).

Maurer et al., CpG-DNA Aided Cross-Presentation of Soluble Antigens by Dendritic Cells, Eur. J. Immunol., 32(8):2356-2364 (2002).

Mcallister et al., Polymeric nanogels produced via inverse microemulsion polymerization as potential gene and antisense delivery agents, J. Am. Chem. Soc., 124:15198-15207 (2002).

McCray et al., Lethal infection of K18-hACE2 mice infected with severe acute respiratory syndrome coronavirus, Journal of Virology, 81(2):813-821 (Jan. 2007).

Mckenna et al., Whole-organism lineage tracing by combinatorial and cumulative genome editing, Science, 353(6298):aaf7907 (2016).

McMillan et al., Modulating Nanoparticle Superlattice Structure Using Proteins with Tunable Bond Distributions, J. Am. Chem. Soc., 139(5): 1754-1757 (2017).

Meckes et al., Enhancing the Stability and Immunomodulatory Activity of Liposomal Spherical Nucleic Acids through Lipid-Tail DNA Modifications, Small, 14:1702909 (2018).

Mesmaeker et al., Backbone modifications in oligonucleotides and peptide nucleic acid systems, Current Opinion in Structural Biology, 5(3):343-355 (1995).

Ming et al., Bioconjugates for targeted delivery of therapeutic oligonucleotides, Adv. Drug. Deliv. Rev., 87:81-89 (2015).

Mirkin et al., A DNA-based method for rationally assembling nanoparticles into macroscopic materials, Nature, 382 (6592):607-609 (1996).

Mirkin, Structure-Function Relationships in the Development of Immunotherapeutic Agents, 14th US-Japan Symposium on Drug Delivery Systems, Maui, HI (2017).

Miyazaki et al., Impaired cytokine response in myeloid dendritic cells in chronic hepatitis C virus infection regardless of enhanced expression of Toll-like receptors and retinoic acid inducible gene-I, Journal of Medical virology, 80(6):980-988 (Jun. 2008).

Mohamed et al., Effect of toll-like receptor 7 and 9 targeted therapy to prevent the development of hepatocellular carcinoma, Liver Int., 35(3):1063-1076 (2015).

Mohamed et al., TLR9 mediates *S. aureus* killing inside osteoblasts via induction of oxidative stress, BMC Microbiology, 16(article 230):8 (2016).

Moreau et al., Evaluation of K18- hACE2 Mice as a Model of SARS-CoV-2 Infection, The American Journal of Tropical Medicine and Hygiene, 103(3):1215-1219 (Sep. 2020).

Morens et al., Emerging infectious diseases: threats to human health and global stability, PLOS Pathogens, 9(7):e1003467(1-3) (Jul. 2013).

Mueller et al., Rapid and Persistent Delivery of Antigen by Lymph Node Targeting PRINT Nanoparticle Vaccine Carrier to Promote Humoral Immunity, Mol. Pharm., 12(5):1356-1365 (2015).

Murad et al., CPG-7909 (PF-3512676, ProMune®): toll-like receptor-9 agonist in cancer therapy, Expert Opinion on Biological Therapy, 7(8):1257-1266 (2007).

Muranski et al., Adoptive immunotherapy of cancer using CD4+T cells, Current Opinion in Immunology, 21(2):200-208 (2009).

Nagase, Substrate specificity of MMPs, in matrix metalloproteinase inhibitors in cancer therapy, Springer, 39-66 (2001).

Naidoo et al., Toxicities of the anti-PD-1 and anti-PD-L1 immune checkpoint antibodies, Annals of Oncology, 26(12):2375-2391 (2015).

Nam et al., Bio-bar-code-based DNA detection with PCR-like sensitivity, J. Am. Chem. Soc., 126:5932-5933 (2004).

Nembrini et al., Nanoparticle Conjugation of Antigen Enhances Cytotoxic TCell Responses in Pulmonary Vaccination, Proc. Natl. Acad. Sci., 108(44):E989-E997 (2011).

Nguyen et al., Enzyme-responsive nanoparticles for targeted accumulation and prolonged retention in heart tissue after myocardial infarction, Advanced Materials, 27(37):5547-5552 (2015).

Nielsen et al., Sequence-selective recognition of DNA by strand displacement with a thymine-substituted polyamide, Science, 254:1497-1500 (1991).

Nikolov et al., Bias-dependent admittance in hybrid bilayer membranes, Langmuir, 22(17):7156-7158 (2006).

Nordly et al., Immunity by formulation design: Induction of high CD8+ T-cell responses by poly(I:C) incorporated into the CAF01 adjuvant via a double emulsion method, Journal of Controlled Release, 150(3):307-317 (Mar. 2011).

Olshavsky et al., Organometallic synthesis of gallium-arsenide crystallites, exhibiting quantum confinement, J. Am. Chem. Soc., 112(25):9438-9439 (1990).

Olson et al., Activatable cell penetrating peptides linked to nanoparticles as dual probes for in vivo fluorescence and MR imaging of proteases, Proceedings of the National Academy of Sciences, 107(9):4311-4316 (2010).

Otsuka et al., PEGylated nanoparticles for biological and pharmaceutical applications, Adv. Drug Delivery. Rev., 64:246-255 (2012).

Ozpolat et al., Nanomedicine based approaches for the delivery of siRNA in cancer, J. Intern. Med., 267(1):44-53 (2010).

Palm et al., Remembrance of Things Past: Long-Term B Cell Memory After Infection and Vaccination, Frontiers in Immunology, 10(1787):1-13 (Jul. 2019).

Park et al., DNA-programmable nanoparticle crystallization, Nature, 451:553-556 (2008).

Patel et al., Naturally-occurring cholesterol analogues in lipid nanoparticles induce polymorphic shape and enhance intracellular delivery of mRNA, Nat. Comm., 11:983 (2020).

Patel et al., Scavenger receptors mediate cellular uptake of polyvalent oligonucleotide-functionalized gold nanoparticles, Bioconjugate Chem., 21(12):2250-2256 (2010).

Patnaik et al., Phase 1 study of pembrolizumab (pembro; MK-3475) plus ipilimumab (IPI) as second-line therapy for advanced non-small cell lung cancer (NSCLC): Keynote-021 cohort D, Journal of Clinical Oncology 33(15):8011-8011 (2015).

Paunovska et al., A Direct Comparison of in Vitro and in Vivo Nucleic Acid Delivery Mediated by Hundreds of Nanoparticles Reveals a Weak Correlation, Nano Lett., 18(3):2148-2157 (2018).

Peter et al., Characterization of suppressive oligodeoxynucleotides that inhibit Toll-like receptor-9-mediated activation of innate immunity, Immunology, 123(1):118-128 (2008).

Pfeiffer et al., Bivalent Cholesterol-Based Coupling of Oligonucleotides to Lipid Membrane Assemblies, J. Am. Chem. Soc., 126:10224-10225 (2004).

(56)     References Cited

OTHER PUBLICATIONS

Pfeiffer et al., Quantification of oligonucleotide modifications of small unilamellar lipid vesicles, Anal. Chem., 78:7493-7498 (2006).

Prigodich et al., Multiplexed nanoflares: mRNA detection in live cells, Anal. Chem., 84:2062-6 (2012).

Prigodich et al., Nano-flares for mRNA regulation and detection, ACS Nano, 3(8):2147-2152 (2009).

Prigodich et al., Selective Enhancement of Nucleases by Polyvalent DNA-Functionalized Gold Nanoparticles, Journal of the American Chemical Society, 133(7):2120-2123 (Jan. 2011).

Prigodich et al., Tailoring DNA structure to increase target hybridization kinetics on surfaces, J. Am. Chem. Soc., 132:10638-41 (2010).

Qin et al., Development of Spherical Nucleic Acids for Prostate Cancer Immunotherapy, Frontiers in Immunology, 11(1333):1-12 (Jul. 2020).

Radovic-Moreno et al., Immunomodulatory spherical nucleic acids, PNAS U.S.A., 112(13):3892-3897 (Mar. 2015).

Rakoff-Nahoum et al., Toll-like receptors and cancer, Nature, 9(1):57-63 (Dec. 2009).

Reed et al., Key roles of adjuvants in modern vaccines, Nature Medicine, 19(12):1597-1608 (Dec. 2013).

Rehli., Of mice and men: species variations of Toll-like receptor expression, Trends in Immunology, 23(8):375-378 (Aug. 2002).

Ries et al., Efficient liposome fusion mediated by lipid-nucleic acid conjugates, Org. Biomol. Chem., 15(42):8936-8945 (2017).

Rincon-Restrepo et al., Vaccine nanocarriers: Coupling intracellular pathways and cellular biodistribution to control CD4 vs CD8 T cell responses, Biomaterials, 132:48-58 (2017).

Rivest et al., Novel Liposomal Formulation for Targeted Gene Delivery, Pharmaceutical Research, 24(1):981-990 (Mar. 2007).

Robson et al., Advantages and Limitations of Current Imaging Techniques for Characterizing Liposome Morphology, Frontiers in Pharmacology, 9:Article 80 (2018).

Rosi et al., Oligonucleotide-Modified Gold Nanoparticles for Intracellular Gene Regulation, Science, 312(5776):1027-1030 (2006).

Rosi et al., Nanostructures in biodiagnostics, Chem. Rev., 105(4):1547-1562 (2005).

Rostovtsev et al., A stepwise huisgen cycloaddition process: copper(I)-catalyzed regioselective "Ligation" of azides and terminal alkynest, Angewandte chemie, 114(14): 2708-2711 (2002).

Sago et al., Nanoparticles That Deliver RNA to Bone Marrow Identified by in Vivo Directed Evolution, J. Am. Chem. Soc., 140(49):17095-17105 (2018).

Sahin et al., MRNA-Based Therapeutics-Developing a New Class of Drugs, Nature Reviews Drug Discovery, 13:759-780 (2014).

Salem et al., Defining the Antigen-Specific T-Cell Response to Vaccination and Poly(I:C)/TLR3 Signaling Evidence of Enhanced Primary and Memory CD8 T-Cell Responses and Antitumor Immunity, Journal of Immunotherapy, 28(3):220-228 (May 2005).

Sambrook et al., Molecular Cloning: A Laboratory Manual (2nd ed. 1989).

Samrat et al., Prospect of SARS-CoV-2 spike protein: Potential role in vaccine and therapeutic development, Virus Research, 288(1):198141(1-17) (Oct. 2020).

Sanghvi et al., Antisense research and applications, CRC Press, Boca Raton, 276-278 (1993).

Sanghvi, Chapter 15, Antisense research and applications, Crooke, S.T. and Lebleu, B. ea., CRC Press, 289-302 (1993).

Santiago-Raber et al., Critical role of TLR7 in the acceleration of systemic lupus erythematosus in TLR9-deficient mice, Journal of autoimmunity, 34(4):339-348 (Jun. 2010).

Sarkar et al., Selection of adjuvants for vaccines targeting specific pathogens, Expert Review of Vaccines , 18(5):505-521 (Apr. 2019).

Schach et al., Reversible Activation of a Cell-Penetrating Peptide in a Membrane Environment, Journal of the American Chemical Society, 137(38):12199-12202 (Sep. 2015).

Schroeder et al., Structure and function of immunoglobulins, The Journal of Allergy and Clinical Immunology, 125(2):S41-S52 (Feb. 2010).

Schulz et al., Toll-like receptor 3 promotes cross-priming to virus-infected cells, Nature, 433(1):887-892 (Feb. 2005).

Schwartz, A cell culture model forT lymphocyte clonal anergy, Science, 248:1349-1356 (1990).

Seferos et al., Locked nucleic acid-nanoparticle conjugates, ChemBioChem, 8:1230-1232 (2007).

Seferos et al., Nano-flares: probes for transfection and mRNA detection in living cells, J. Am. Chem. Soc., 129 (50):15477-15479 (2007).

Seferos et al., Polyvalent DNA nanoparticle conjugates stabilize nucleic acids, Nano Lett., 9(1 ):308-311 (2009).

Semple et al., Rational Design of Cationic Lipids for SiRNA Delivery, Nat. Biotechnol., 28(2):172-176 (2010).

Senior et al., Stability of small unilamellar liposomes in serum and clearance from the circulation: the effect of the phospholipid and cholesterol components, Life Sci., 30:2123-2136 (1982).

Silvas et al., Contribution of SARS-CoV-2 Accessory Proteins to Viral Pathogenicity in K18 Human ACE2 Transgenic Mice, Journal of Virology, 95(17):e00402-21(1-14) (Aug. 2021).

Siutter et al., Conjugation of Ovalbumin to Trimethyl Chitosan Improves Immunogenicity of the Antigen, J. Control. Release, 143(2):207-214 (2010).

Skakuj et al., Conjugation Chemistry-Dependent T-Cell Activation with Spherical Nucleic Acids, Journal of the American Chemical Society, 140(4):1227-1230 (2018).

Slack et al., Rotaxane probes for protease detection by 129 Xe hyperCEST NMR, chemical communications, 53(6):1076-1079 (2017).

Slaymaker et al., Rationally engineered Cas9 nucleases with improved specificity, Science, 351(6268):84-88 (Jan. 2016).

Smargon et al., Cas13b Is a Type VI-B CRISPR-Associated RNA-Guided RNase Differentially Regulated by Accessory Proteins Csx27 and Csx28, Molecular Cell, 65(4):618-630 (Feb. 2017).

Sokolova et al., The use of calcium phosphate nanoparticles encapsulating Toll-like receptor ligands and the antigen hemagglutinin to induce dendritic cell maturation and T cell activation, Biomaterials, 31:5627-5633 (2010).

Sprangers et al., Liposomal Spherical Nucleic Acids for Regulating Long Noncoding RNAs in the Nucleus, Small, 13(10):1602753 (2017).

Staben et al., Targeted Drug Delivery through the Traceless Release of Tertiary and Heteroaryl Amines from Antibody-Drug Conjugates, Nat. Chem., 8:1112-1119 (2016).

Stengel et al., Determinants for Membrane Fusion Induced by Cholesterol-Modified DNA Zippers, J. Phvs. Chem. B., 112:8264-74 (2008).

Stengel et al., DNA-Induced Programmable Fusion of Phospholipid Vesicles, J. Am. Chem. Soc., 129:9584-5 (2007).

Strandskog et al., Double-stranded RNA-and CpG DNA-induced immune responses in Atlantic salmon: comparison and synergies, Vaccine, 26(36):4704-4715 (Aug. 2008).

Strecker et el., Engineering of CRISPR-Cas12b for human genome editing, Nature Communications, 10(212):1-8 (Jan. 2019).

Sulkowski et al., The influence of temperature, cholesterol content and pH on liposome stability, J. Mol. Struct., 744-747:737-747 (2005).

Suma et al., Modulated Fragmentation of Proapoptotic Peptide Nanoparticles Regulates Cytotoxicity, J. Am. Chem. Soc., 139(11):4009-4018 (2017).

Swain et al., Expanding roles for CD4+ T cells in immunity to viruses, Nature Reviews Immunology, 12:136-148 (2012).

Switaj et al., CpG Immunostimulatory Oligodeoxynucleotide 1826 Enhances Antitumor Effect of Interleukin 12 Gene-Modified Tumor Vaccine in a Melanoma Model in Mice, Clinical Cancer Research, 10:4165-4175 (2004).

Takemori et al., Chapter 14—B Cell Memory and Plasma Cell Development, Molecular Biology of B Cells (Second Edition), 227-249 (Oct. 2014).

Tan et al., Blurring the Role of Oligonucleotides: Spherical Nucleic Acids as a Drug Delivery Vehicle, J. Am. Chem. Soc., 138(34):10834-10837 (2016).

Thomas, The Interaction of HgCl2 with Sodium Thymonucleate, J. Am. Chem. Soc., 76(23):6032-6034 (1954).

(56)          References Cited

OTHER PUBLICATIONS

Tincer et al., Immunostimulatory activity of polysccharidepoly (I:C) nanoparticles, Biomaterial., 32(18):4275-4282 (2011).

Titta et al., Nanoparticle Conjugation of CpG Enhances Adjuvancy for Cellular Immunity and Memory Recall at Low Dose, Proc. Natl. Acad. Sci., 110(49):19902-19907 (2013).

Tiwari et al., Drug delivery systems: An updated review, International journal of pharmaceutical investigation, 2(1):2-11 (2012).

Tondelli et al., Highly efficient cellular uptake of c-myb antisense oligonucleotides through specifically designed polymeric nanospheres, Nucl. Acids Res., 26(23):5425-5431 (1998).

Tregoning et al., Adjuvanted influenza vaccines, Human Vaccines & Immunotherapeutics , 14(3):550-564 (Mar. 2018).

Tzeng et al., Temporally programmed CD8a+ DC activation enhances combination cancer immunotherapy, Cell reports, 17(10):2503-2511 (2016).

Uchida et al., Gallium arsenide nanocrystals prepared in quinoline, J. Phys. Chem., 95:5382 (1992).

UniProt Consortium, UniProt: the universal protein knowledgebase in 2021, Nucleic Acids Research, 49(D1):D480-D489 (Jan. 2021).

Van Der Vlies et al., Synthesis of Pyridyl Disulfide-Functionalized Nanoparticles for Conjugating Thiol-Containing Small Molecules, Peptides, and Proteins, Bioconjug. Chem., 21(4):653-662 (2010).

Vance et al., The design of polyvalent scaffolds for targeted delivery, Advanced Drug Delivery Reviews, 61(11):931-939 (Sep. 2009).

Veiga et al., Targeted lipid nanoparticles for RNA therapeutics and immunomodulation in leukocytes, Advanced Drug Delivery Reviews, 159:364-376 (2020).

Veiseh et al., Optical and MRI multifunctional nanoprobe for targeting gliomas, Nano Lett., 5(6):1003-1008 (2005).

Versluis et al., In situ modification of plain liposomes with lipidated coiled coil forming peptides induces membrane fusion, J. Am. Chem. Soc., 135:8057-8062 (2013).

Verthelyi et al., CpG-ODN—Safety Considerations, Microbial DNA and Host Immunity, 385-396 (2002).

Vollmer et al., Characterization of three CpG oligodeoxynucleotide classes with distinct immunostimulatory activities, Eur. J. Immunol., 34:251-62 (2004).

Wang et al (Matrix metalloproteinase 2-responsive micelle for siRNA delivery. Biomaterials 35 (2014) 7622-7634) and Fahmy et al (US 2015/0064265). (Year: 2014).

Wang et al., Altering DNA-Programmable Colloidal Crystallization Paths by Modulating Particle Repulsion, Nano Letters, 17:5126-32 (2017).

Wang et al., Delivery of oligonucleotides with lipid nanoparticles, Adv. Drug Deliv. Rev., 87:68-80 (2015).

Wang et al., Excessive Neutrophils and Neutrophil Extracellular Traps in COVID-19, Frontiers in Immunology, 11 (2063):1-13 (Aug. 2020).

Wang et al., Nanometer-sized semiconductor clusters: materials synthesis, quantum size effects, and photophysical properties, J. Phys. Chem., 95:525-532 (1991).

Wang et al., Rational vaccinology with spherical nucleic acids, PNAS U.S.A., 10473-481 (2019).

Wang et al., The Functional Effects of Physical Interactions among Toll-like Receptors 7, 8, and 9, The Journal of Biological Chemistry, 281(49): 37427-37434 (2006).

Weber et al., Nivolumab versus chemotherapy in patients with advanced melanoma who progressed after anti-CTLA-4 treatment (CheckMate 037): a randomised, controlled, open-label, phase 3 trial, The Lancet Oncology, 16:375-384 (2015).

Weeranta et al., CpG DNA induces stronger immune responses with less toxicity than other adjuvants, Vaccine, 18(17):1755-1762 (2000).

Wei et al., Next-generation influenza vaccines: opportunities and challenges, Nature Reviews Drug Discovery, 19(4):239-252 (February 202).

Wei et al., Polyvalent Immunostimulatory Nanoagents with Self-Assembled CpG Oligonucleotide-Conjugated Gold Nanoparticles, Angewandte Chemie International Edition, 51(5):1202-1206 (2012).

Weller, Colloidal semiconductor Q-particles: Chemistry in the transition region between solid state and molecules, Angew. Chem. Int. Ed. Engl., 32(1):41-53 (1993).

Welters et al., Induction of Tumor-Specific CD4+ and CD8+ T-Cell Immunity in Cervical Cancer Patients by a Human Papillomavirus Type 16 E6 and E7 Long Peptides Vaccine, Clin. Cancer Res., 14(1):178-187 (2008).

West et al., Recognition and signaling by toll-like receptors, Annu. Rev. Cell Dev. Biol., 22:409-37 (2006).

Whitehead et al., Knocking down barriers: advances in siRNA delivery, Nat. Rev. Drug. Discov., 8:129-138 (2009).

Willis et al., Liposome-Anchored Vascular Endothelial Growth Factor Aptamers, Bioconjugate Chem. 9 573-582 (1998).

Wilson et al., pH-Responsive Nanoparticle Vaccines for Dual-Delivery of Antigens and Immunostimulatory Oligonucleotides, ACS Nano, 7(5):3912-3925 (2013).

Winkler et al., SARS-CoV-2 infection of human ACE2-transgenic mice causes severe lung inflammation and impaired function, Nature Immunology, 21(11):1327-1335 (Nov. 2020).

Wong et al., Traditional and new influenza vaccines, Clinical Microbiology Reviews, 26(3):476-492 (Jul. 2013).

Wu et al., DNA aptamer-micelle as an efficient detection/delivery vehicle toward cancer cells, Proc. Natl. Acad. Sci. SA., 107(1):5-10 (2010).

Wu et al., The relationship between CD27 negative and positive B cell populations in human peripheral blood, Frontiers in Immunology, 2(B1):1-12 (Dec. 2011).

Xing et al., Selective delivery of an anticancer drug with aptamer-functionalized liposomes to breast cancer cells in vitro and in vivo, J. Mater. Chem. B., 1:5288-5297 (2013).

Xu et al., Asymmetric functionalization of gold nanoparticles with oligonucleotides, J. Am. Chem. Soc., 128:9286-9287.

Xu et al., Rendering Protein-Based Particles Transiently Insoluble for Therapeutic Applications, J. Am. Chem. Soc., 134(21):8774-8777 (2012).

Yamane et al., On the Complexing of Desoxyribonucleic Acid (DNA) by Mercuric Ion1, J. Am. Chem. Soc., 83(12):2599-2607 (1961).

Yamankurt et al., Exploration of the nanomedicine-design space with high-throughput screening and machine learning, Nat. Biomed. Eng., 3(4):318-327 (2019).

Yin et al., Supramolecular self-assembled nanoparticles mediate oral delivery of therapeutic TNF-? siRNA against systemic inflammation, Anaew. Chem. Int. Ed. Enal., 125(22):5757-5761 (2013).

Young et al., Hollow spherical nucleic acids for intracellular gene regulation based upon biocompatible silica shells, Nano Lett., 12(7):3867-3871 (2012).

Zaks et al., Efficient Immunization and Cross-Priming by Vaccine Adjuvants Containing TLR3 or TLR9 Agonists Complexed to Cationic Liposomes, The Journal of Immunology, 176(12):7335-7345 (Jun. 2006).

Zalatan et al., Engineering complex synthetic transcriptional programs with CRISPR RNA scaffolds, Cell, 160(1-2):339-350 (Jan. 2015).

Zent et al., Phase I clinical trial of CpG oligonucleotide 7909 (PF-03512676) in patients with previously treated chronic lymphocytic leukemia, Leukemia & Lymphoma, 53(2):211-217 (2012).

Zhang et al., A general approach to DNA-programmable atom equivalents, Nat. Mater., 12(8)741-746 (2013).

Zhang et al., An extremely stable and orthogonal DNA base pair with a simplified three-carbon backbone, J. Am. Chem. Soc., 127(1):74-75 (2005).

Zhang et al., Antibody-linked spherical nucleic acids for cellular targeting, J. Am. Chem. Soc., 134:16488-91 (2012).

Zhang et al., Informational Liposomes: Complexes Derived from Cholesteryl-conjugated Oligonucleotides and Liposomes, Tetrahedron Letters, 37(35):6243-6246 (1996).

Zhang et al., PowerBLAST: a new network BLAST application for interactive or automated sequence analysis and annotation, Genome Res., 7(6):649-656 (1997).

Zhang et al., Structure-activity relationships of cationic shell-crosslinked knedel-like nanoparticles: shell composition and transfection efficiency/cytotoxicity, Biomaterials, 31:1805-1813 (2010).

(56) References Cited

OTHER PUBLICATIONS

Zheng et al., A spherical nucleic acid platform based on self-assembled DNA biopolymer for high-performance cancer therapy, ACS Nano, 7(8):6545-6554 (2013).

Zheng et al., Aptamer nano-flares for molecular detection in living cells, Nano Lett., 9(9):3258-3261 (2009).

Zheng et al., COVID-19 treatments and pathogenesis including anosmia in K18-hACE2 mice, Nature, 589 (7843):603-607 (Jan. 2021).

Zheng et al., Topical delivery of siRNA-based spherical nucleic acid nanoparticle conjugates for gene regulation, Proceedings of the National Academy of Sciences, 109(30):11975-11980 (2012).

Zhu et al., Matrix metalloprotease 2-responsive multifunctional liposomal nanocarrier for enhanced tumor targeting, ACS Nano., 6(4):3491-3498 (2012).

Zhu et al., Toll-like receptor ligands synergize through distinct dendritic cell pathways to induce T cell responses: Implications for vaccines, PNAS U.S.A., 105(42):16260-16265 (Oct. 2008).

Zhu et al., Using 3 TLR ligands as a combination adjuvant induces qualitative changes in T cell responses needed for antiviral protection in mice, J. Clin. Invest., 120(2):607-616 (Jan. 2010).

Zimmermann et al., A novel silver(i)-mediated DNA base pair, J. Am. Chem. Soc., 124(46):13684-13685 (2002).

Zuris et al., Cationic lipid-mediated delivery of proteins enables efficient protein-based genome editing in vitro and in vivo, Nature Biotechnology, 33(1):73-80 (Jan. 2015).

* cited by examiner

**p<0.0001, p<0.01
ns = non-significant

Low dose = 500 nM; High Dose = 2000 nM

Figure 4:
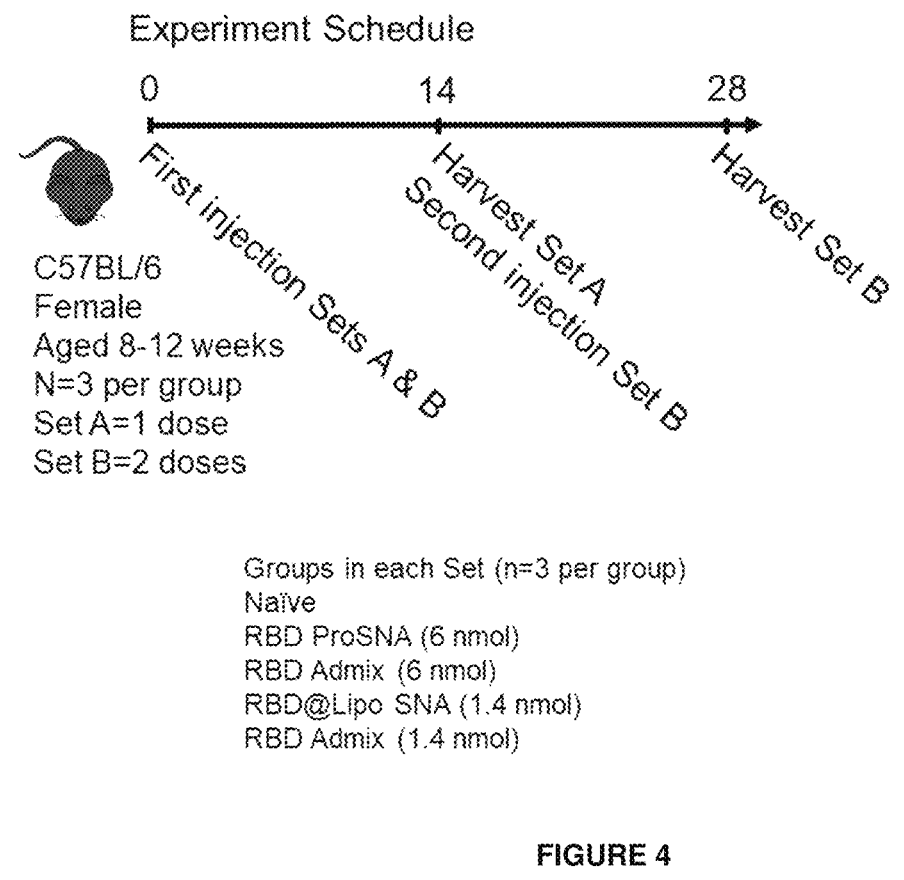

Experiment Schedule

C57BL/6
Female
Aged 8-12 weeks
N=3 per group
Set A=1 dose
Set B=2 doses

Groups in each Set (n=3 per group)
Naïve
RBD ProSNA (6 nmol)
RBD Admix (6 nmol)
RBD@Lipo SNA (1.4 nmol)
RBD Admix (1.4 nmol)

ANTIVIRAL VACCINES USING SPHERICAL NUCLEIC ACIDS

This application claims the priority benefit under 35 U.S.C. § 119(e) of U.S. Provisional Patent Application No. 63/160,600, filed Mar. 12, 2021 and U.S. Provisional Patent Application No. 63/250,908, filed Sep. 30, 2021, which are incorporated herein by reference in their entirety.

STATEMENT OF GOVERNMENT INTEREST

This invention was made with government support under grant number FA8650-15-2-5518 awarded by the Air Force Research Laboratory (AFRL), grant number FA9550-17-1-0348 awarded by the Department of Defense, Department of the Air Force, Air Force Office of Scientific Research (AFOSR), and grant numbers CA199091, CA208783, and CA221747 awarded by the National Institutes of Health (NIH). The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 2021-003R_Seqlisting.txt; Size 61,641 bytes; Created: Mar. 1, 2022.

BACKGROUND

The rapid and global spread of COVID-19 has emphatically revealed the need for new preventative vaccination technologies. The need for the rapid development and deployment of vaccines, to protect the uninfected and thereby curb the spread of infection, has highlighted shortcomings in vaccinology: challenges in both designing and manufacturing maximally protective vaccine formulations.

SUMMARY

Antiviral vaccines potently activate and prime the immune system against infectious diseases, stimulating targeted prophylactic responses so that one is prepared for the actual infection. Using an adjuvant (immune system activator) and an antigen (immune system target), these vaccines drive the immune system to seek out and kill viruses. Previously, strategies included simple mixtures of adjuvant and antigen including recombinant proteins or inactivated viral particles, or delivery of mRNA sequences which code for the antigen. These techniques suffered from rapid degradation, low cellular uptake, and lack of vaccine structural control. The present disclosure provides spherical nucleic acid (SNA) structures that comprise a dense shell of oligonucleotides radially conjugated to a nanoparticle core. The SNA structure addresses the aforementioned shortcomings by improving cellular delivery, inhibiting degradation by biological milieu, and enabling fine-tuned structural control, which has been linked to improved immune responses.

Exemplary applications of the subject matter of the disclosure include, but are not limited to vaccine design, treating infectious disease, and nanomedicine. Advantages of the subject matter of the disclosure include, but are not limited to, structural control of vaccine leading to controlled presentation of components to cells, the presentation enhances serum stability, platform technology with modularity for changing the viral target, and enhanced immune responses.

Accordingly, in some aspects the disclosure provides a spherical nucleic acid (SNA) comprising: (a) a nanoparticle core; (b) a shell of oligonucleotides attached to the external surface of the nanoparticle core, the shell of oligonucleotides comprising one or more immunostimulatory oligonucleotides; and (c) a viral antigen encapsulated in the nanoparticle core, wherein the viral antigen is receptor binding domain (RBD) (SEQ ID NO: 4), S1 subunit of Spike (SEQ ID NO: 5), SARS-CoV-2 Spike (SEQ ID NO: 2), a variant of any of the foregoing, or a combination thereof. In some aspects, the disclosure provides a spherical nucleic acid (SNA) comprising (a) a nanoparticle core; (b) a shell of oligonucleotides attached to the external surface of the nanoparticle core, the shell of oligonucleotides comprising one or more immunostimulatory oligonucleotides; and (c) a viral antigen encapsulated in the nanoparticle core. In some embodiments, the viral antigen is receptor binding domain (RBD) (SEQ ID NO: 4), S1 subunit of Spike (SEQ ID NO: 5), SARS-CoV-2 Spike (SEQ ID NO: 2), a variant of any of the foregoing, or a combination thereof. In various embodiments, the viral antigen comprises or consists of a sequence that is at least 80% identical to receptor binding domain (RBD) (SEQ ID NO: 4), S1 subunit of Spike (SEQ ID NO: 5), SARS-CoV-2 Spike (SEQ ID NO: 2), SARS-CoV-2 surface glycoprotein (SEQ ID NO: 14), SARS-CoV-2 RBD (SEQ ID NO: 15), SARS-CoV-2 Omicron variant RBD (SEQ ID NO: 16), RBD (SEQ ID NO: 17), or a combination thereof. In some embodiments, at least about 0.5 milligram (mg) of the viral antigen is encapsulated in the nanoparticle core per micromole (μmol) of oligonucleotides in the shell of oligonucleotides. In some embodiments, about 0.5 mg to about 10 mg of the viral antigen is encapsulated in the nanoparticle core per micromole (μmol) of oligonucleotides in the shell of oligonucleotides. In some embodiments, about 1 mg to about 10 mg of the viral antigen is encapsulated in the nanoparticle core per micromole (μmol) of oligonucleotides in the shell of oligonucleotides. In various embodiments, the viral antigen is a full length protein, one or more fragments of the full length protein, a peptide, or a combination thereof. In some embodiments, the nanoparticle core is a liposomal core or a lipid nanoparticle core. In some embodiments, the lipid nanoparticle core comprises an ionizable lipid, a phospholipid, a sterol, and a lipid-polyethylene glycol (lipid-PEG) conjugate. In further embodiments, each oligonucleotide in the shell of oligonucleotides is covalently attached to the exterior of the lipid nanoparticle core through the lipid-PEG conjugate. In some embodiments, the liposomal core comprises a plurality of lipid groups. In further embodiments, the plurality of lipid groups comprises a lipid selected from the group consisting of the phosphatidylcholine, phosphatidylglycerol, and phosphatidylethanolamine families of lipids. In some embodiments, the lipid is 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1,2-dihexadecanoyl-sn-glycero-3-phosphoethanolamine (DPPE), monophosphoryl Lipid A (MPLA), or a combination thereof. In some embodiments, at least one oligonucleotide in the shell of oligonucleotides is attached to the exterior of the liposomal or lipid nanoparticle core through a lipid anchor group. In further embodiments, the lipid anchor group is attached to the 5' end or the 3' end of the at least one oligonucleotide. In still further embodiments, the lipid anchor group is tocopherol or cholesterol. In some embodiments, at least one oligonucleotide in the shell of oligonucleotides is modified on its 5' end and/or 3' end with dibenzocyclooctyl (DBCO). In some embodiments, at least one oligonucleotide in the shell of oligonucleotides is modified on its 5' end and/or 3' end with a thiol. In some embodiments, the thiol is for conjugation to a maleimide functionalized lipid. In some embodiments, the shell of oligonucleotides comprises DNA, RNA, or a combination thereof. In further embodiments, the shell of oligonucleotides comprises DNA oligonucleotides and RNA oligonucleotides. In further embodiments, the shell of oligonucleotides comprises single-stranded DNA, double-stranded DNA, single-stranded RNA, double-stranded RNA, or a combination thereof. In some embodiments, the nanoparticle core comprises DNA, RNA, or a combination thereof encapsulated therein. In further embodiments, the nanoparticle core comprises DNA oligonucleotides and RNA oligonucleotides. In some embodiments, the nanoparticle core comprises single-stranded DNA, double-stranded DNA, single-stranded RNA, double-stranded RNA, or a combination thereof encapsulated therein. In further embodiments, at least one oligonucleotide in the shell of oligonucleotides is a modified oligonucleotide. In some embodiments, the shell of oligonucleotides comprises about 2 to about 200 oligonucleotides. In some embodiments, the shell of oligonucleotides comprises about 2 to about 100 oligonucleotides. In some embodiments, the shell of oligonucleotides comprises about 150 oligonucleotides. In some embodiments, the shell of oligonucleotides comprises about 200 oligonucleotides. In further embodiments, the shell of oligonucleotides comprises about 10 to about 80 oligonucleotides. In some embodiments, the shell of oligonucleotides comprises about 75 oligonucleotides. In some embodiments, the ratio of oligonucleotides in the shell of oligonucleotides to the viral antigen encapsulated in the nanoparticle core is about 10:1 to about 70:1 (number of oligonucleotides in the shell of oligonucleotides to the number of viral antigen molecules encapsulated in the nanoparticle core). In some embodiments, the ratio of oligonucleotides in the shell of oligonucleotides to the viral antigen encapsulated in the nanoparticle core is about 10:1 to about 50:1. In further embodiments, the ratio of oligonucleotides in the shell of oligonucleotides to the viral antigen encapsulated in the nanoparticle core is about 16:1. In some embodiments, the ratio of oligonucleotides in the shell of oligonucleotides to the viral antigen encapsulated in the nanoparticle core is about 32:1. In some embodiments, the ratio of oligonucleotides in the shell of oligonucleotides to the viral antigen encapsulated in the nanoparticle core is about 43:1. In further embodiments, each oligonucleotide in the shell of oligonucleotides is about 5 to about 1000 nucleotides in length. In some embodiments, each oligonucleotide in the shell of oligonucleotides is about 10 to about 50 nucleotides in length. In some embodiments, each oligonucleotide in the shell of oligonucleotides is about 20 to about 30 nucleotides in length. In further embodiments, diameter of the SNA is about 1 nanometer (nm) to about 500 nm. In further embodiments, diameter of the SNA is less than or equal to about 80 nanometers. In still further embodiments, diameter of the SNA is less than or equal to about 50 nanometers. In some embodiments, the shell of oligonucleotides comprises a targeting oligonucleotide, an inhibitory oligonucleotide, or a combination thereof. In further embodiments, the inhibitory oligonucleotide is an antisense oligonucleotide, small interfering RNA (siRNA), an aptamer, a short hairpin RNA (shRNA), a DNAzyme, or an aptazyme. In some embodiments, each oligonucleotide in the shell of oligonucleotides is an immunostimulatory oligonucleotide. In further embodiments, the immunostimulatory oligonucleotide is a CpG-motif containing oligonucleotide, a double-stranded DNA oligonucleotide, or a single-stranded RNA oligonucleotide. In still further embodiments, each of the immunostimulatory oligonucleotides is a toll-like receptor (TLR) agonist. In yet additional embodiments, the TLR is toll-like receptor 1 (TLR1), toll-like receptor 2 (TLR2), toll-like receptor 3 (TLR3), toll-like receptor 4 (TLR4), toll-like receptor 5 (TLR5), toll-like receptor 6 (TLR6), toll-like receptor 7 (TLR7), toll-like receptor 8 (TLR8), toll-like receptor 9 (TLR9), toll-like receptor 10 (TLR10), toll-like receptor 11 (TLR11), toll-like receptor 12 (TLR12), toll-like receptor 13 (TLR13), or a combination thereof. In some embodiments, the TLR is toll-like receptor 3 (TLR3), toll-like receptor 4 (TLR4), toll-like receptor 7 (TLR7), toll-like receptor 8 (TLR8), toll-like receptor 9 (TLR9), or a combination thereof. In some embodiments, the TLR is TLR9.

In some aspects the disclosure provides a pharmaceutical formulation comprising a SNA of the disclosure and a pharmaceutically acceptable carrier or diluent.

In further aspects, the disclosure provides an antigenic composition comprising a SNA of the disclosure in a pharmaceutically acceptable carrier, diluent, stabilizer, preservative, or adjuvant, or a pharmaceutical formulation of the disclosure, wherein the antigenic composition is capable of generating an immune response including antibody generation or a protective immune response in a mammalian subject. In some embodiments, the immune response includes an antibody response. In further embodiments, the antibody response is a neutralizing antibody response or a protective antibody response.

In some aspects, the disclosure provides a method of producing an immune response to a viral antigen in a subject, comprising administering to the subject an effective amount of an antigenic composition of the disclosure, or a pharmaceutical formulation of the disclosure, thereby producing an immune response to the viral antigen in the subject. In some embodiments, the immune response includes an antibody response. In further embodiments, the antibody response is a total antigen-specific antibody response. In some embodiments, the antibody response is a neutralizing antibody response or a protective antibody response.

In some aspects, the disclosure provides a method of treating a viral infection in a subject in need thereof, comprising administering to the subject an effective amount of a SNA of the disclosure, a pharmaceutical formulation of the disclosure, or an antigenic composition of the disclosure, thereby treating the viral infection in the subject. In some embodiments, the administering is subcutaneous. In further embodiments, the administering is intravenous, intraperitoneal, intranasal, or intramuscular. In some embodiments, the administering comprises a first dose and a second dose of the antigenic composition. In some embodiments, the administering comprises at least one dose of the antigenic composition. In further embodiments, the administering comprises a first dose and a second dose of the pharmaceutical formulation. In some embodiments, the administering comprises at least one dose of the pharmaceutical formulation. In still further embodiments, the second dose is administered about or at least about 2 weeks after the first dose. In some embodiments, the administering results in an increase in the amount of total antigen-specific antibodies against the viral antigen that is produced in the subject relative to the amount of total antigen-specific antibodies against the viral antigen that is produced in a subject who was not administered the pharmaceutical formulation or the antigenic composition. In further embodiments, the administering results in an increase in the amount of neutralizing antibodies against the viral antigen that is produced in the subject relative to the amount of neutralizing antibodies against the viral antigen that is produced in a subject who was not administered the pharmaceutical formulation or the antigenic composition. In some embodiments, the increase is a 2-fold increase, a 5-fold increase, a 10-fold increase, a 50-fold increase, a 100-fold increase, a 200-fold increase, a 500-fold increase, a 700-fold increase, or a 1000-fold increase.

BRIEF DESCRIPTION OF THE FIGURES

FIG. 4 depicts the in vivo vaccination schedule of ProSNAs and Liposomal SNAs.

Sidak's or (D) Dunnett's multiple comparisons test. n=3-4 per group. *p<0.05; **p<0.01; ns=non-significant; other p values are shown.

Figure 11:
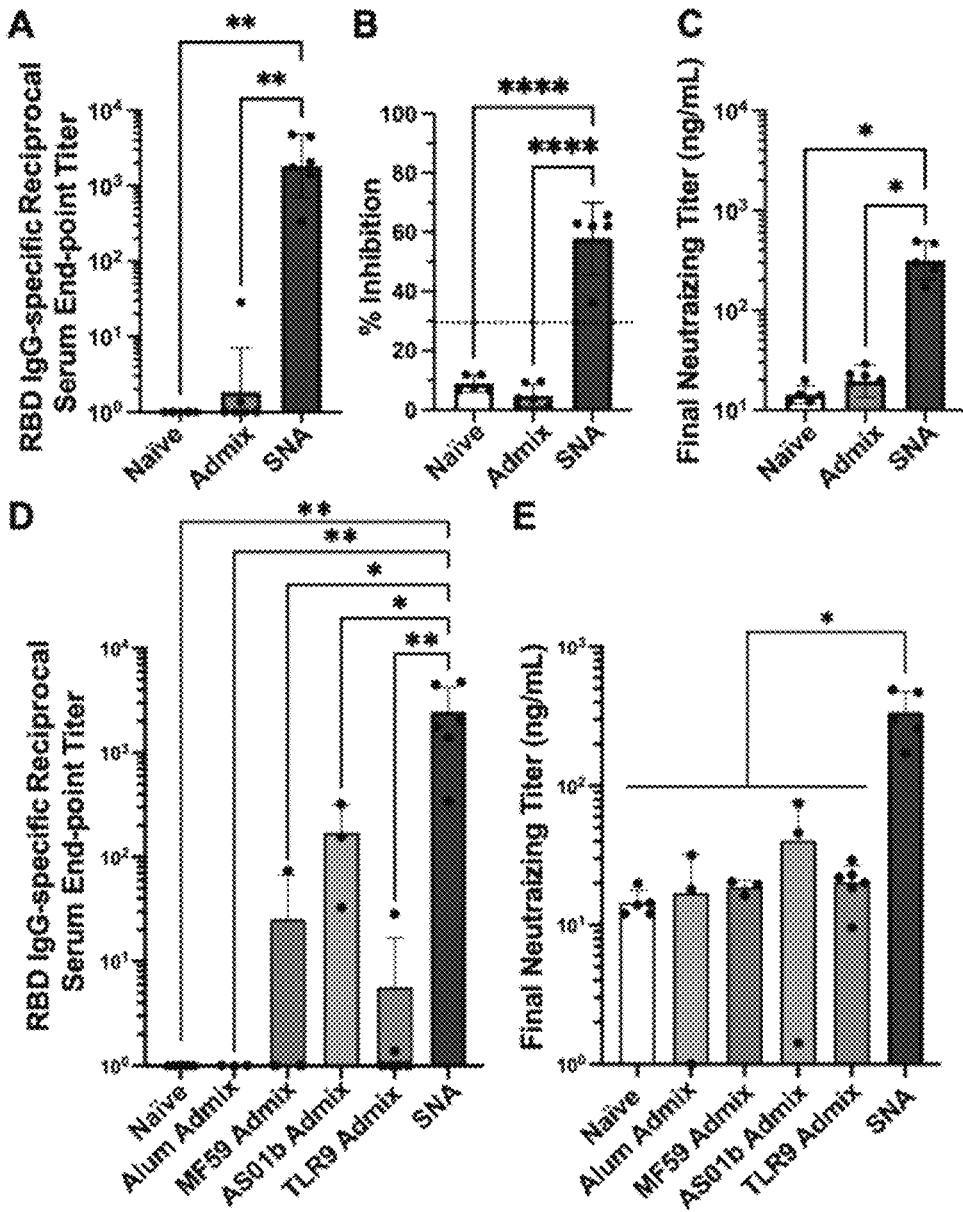

FIG. 11 shows that the SNA structure induced higher levels of antigen-specific binding and neutralizing titers in vivo. (A) Samples were quantified via ELISA for the presence of RBD-specific IgG binding antibodies. Reciprocal serum end-point titers were calculated through fitting absorbance at 450 nm values to a 4PL Sigmoidal curve. (B) Sera were employed in a pseudovirus inhibition study and were assessed for the inhibition percentage at a 1:10 sera dilution, or (C) were fit to a standard curve to calculate a final neutralizing titer. Dashed line in (B) represents threshold cutoff value for positive inhibition according to manufacturer's protocol. (D) RBD-specific IgG binding antibody measurement of SNA compared with simple mixture immunizations formulated using commercial adjuvants. (E) Final neutralizing titer calculated in a pseudovirus inhibition study and fit to a standard curve. All graphs show mean and SD, n=3-6 per group. Mice were injected with 1.4 nmol by RBD protein and one of the following adjuvants: 44 nmol by CpG DNA (SNA and TLR9 admix groups), 40 µg by Al³⁺ (Alum admix), 25 µL by AddaVax (MF59 admix), 4.2 µg by QS21 and MPLA4 (AS01b admix). Dosing can be found in greater detail in "In Vivo Immunization in Mice" section of Example 2. For panels A, B, D, analysis was done using an ordinary one-way ANOVA followed by a Tukey's multiple comparisons test. For panels C, E, analysis was done using a Brown-Forsythe ANOVA followed by a Dunnett's multiple comparisons test. n=3-4 per group. *p<0.05; p<0.01; *p<0.001; ****p<0.0001.

Figure 12:
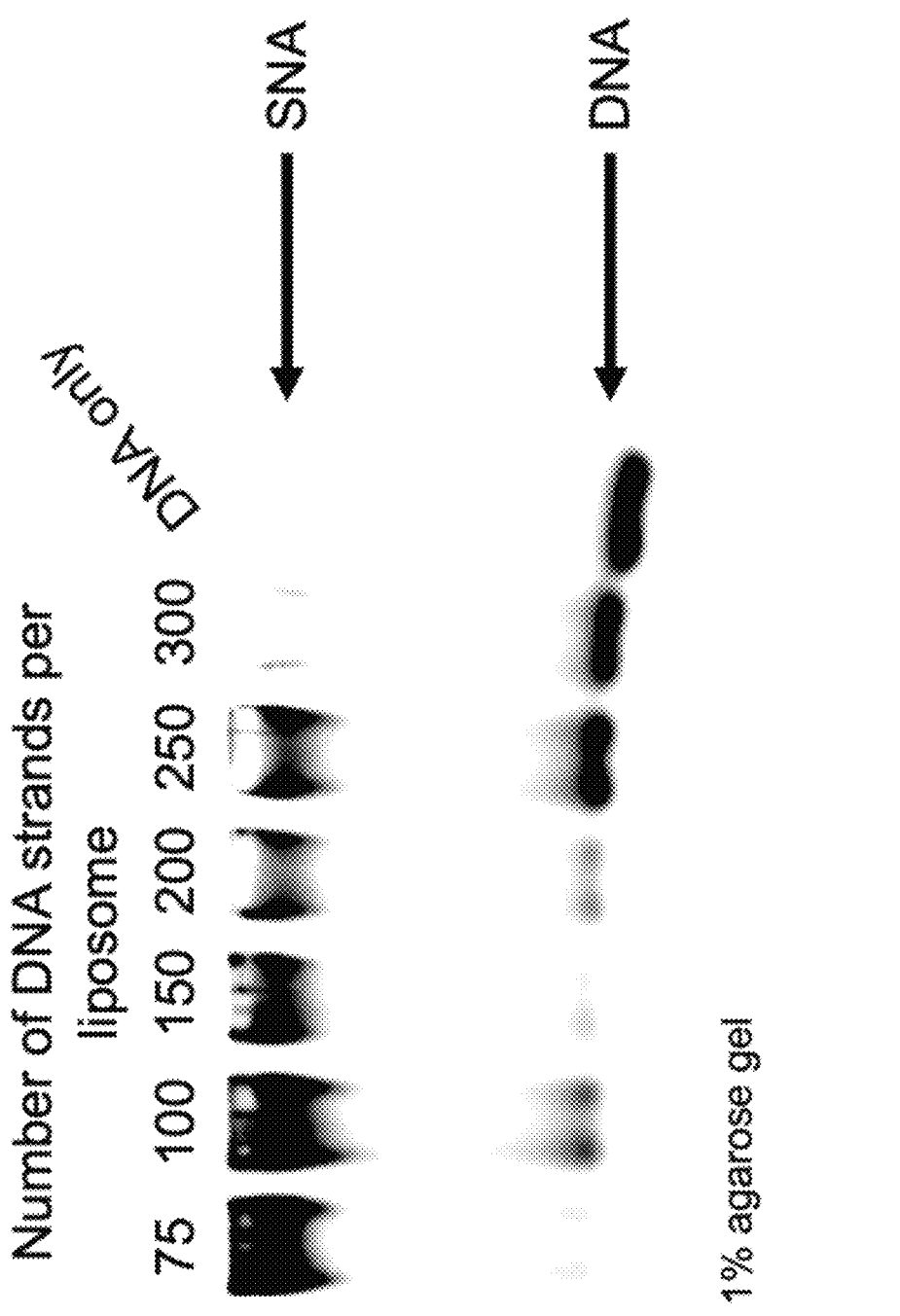

FIG. 12 shows a determination of maximum loading of DNA per liposome before dissociation. The last detectable SNA band that also has a low intensity DNA band, indicating low levels of dissociation, is present at a stoichiometry of 200 DNA strands per liposome.

Figure 13:
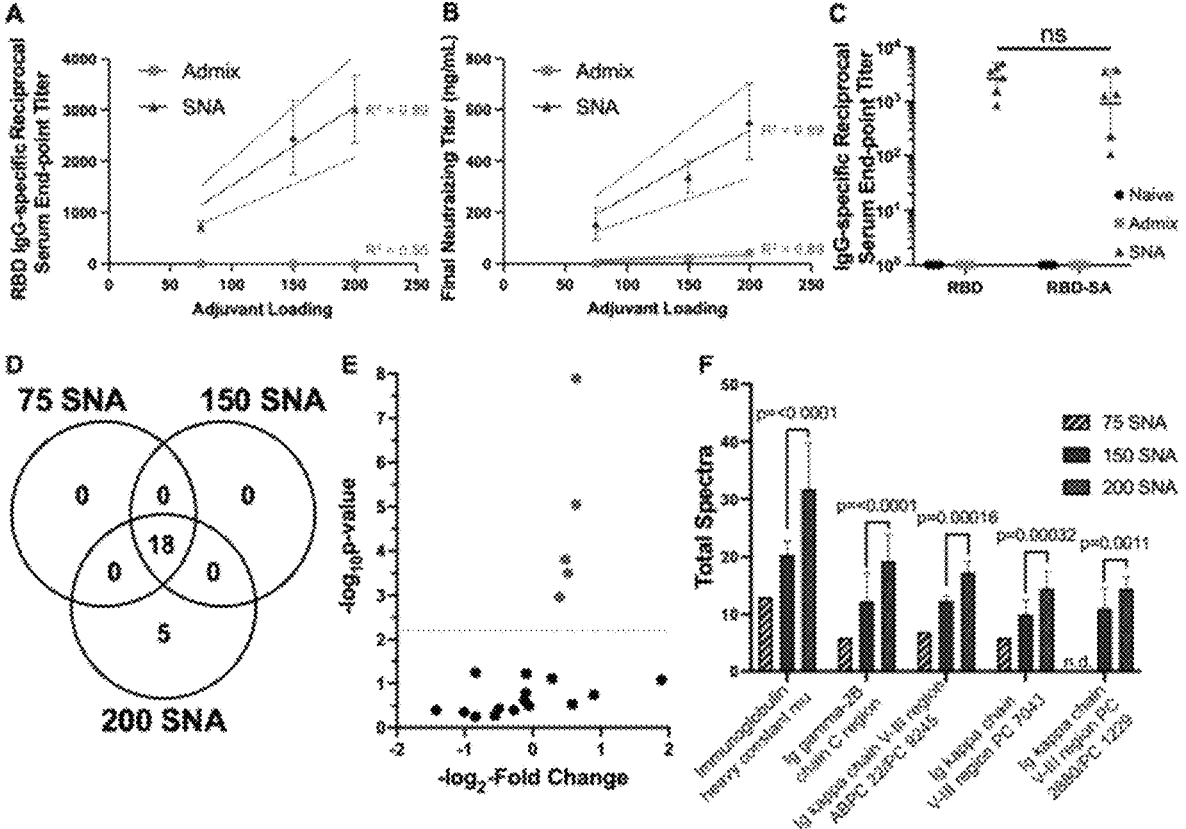

FIG. 13 shows that SNA vaccines formulated with different loadings of adjuvant DNA as the shell demonstrate linear correlations in resulting binding and neutralizing antibody production as a result of differential protein expression. (A) RBD-specific IgG binding antibodies shown as the reciprocal serum end-point titer were plotted against adjuvant loading for the 3 different SNA groups. (B) The pseudovirus inhibition assay demonstrated the same positive linear relationship between adjuvant loading and the calculated final neutralizing titer. Graphs show mean and SEM for n=3-6 per group. (C) Antibodies generated by the different vaccines were assessed for their ability to bind the B.1.351 variant of the RBD protein (RBD-SA). Graph shows mean and SD for n=3-6 per group. Analysis performed doing a two-way ANOVA followed by Sidak's multiple comparisons test. ns=non-significant change in reciprocal serum end-point titer for SNA-raised antibodies. (D) Quantitative profile of immunoglobulins between the 3 SNA groups with different loadings of adjuvant DNA on shell. (E) Volcano plot showing relative fold change and significance of different Igs when comparing the 200 SNA against the 150 SNA group. Red line indicates significance threshold. (F) The five identified upregulated proteins were plotted as a function of total spectra with significance between 200 SNA versus 150 SNA shown. N.d.=not detected. Significance threshold=p<0.0063. Mice were injected with the following: SNA 200 and admix equivalent were dosed at 1.4 nmol by RBD protein, 60 nmol by CpG DNA. SNA 150 and admix equivalent was dosed at 1.4 nmol by RBD protein, 44 nmol by CpG DNA. SNA 75 and admix equivalent was dosed at 1.4 nmol by RBD protein, 22 nmol by CpG DNA. Dosing can be found in greater detail in "In Vivo Immunization in Mice" section of Example 2.

Figure 14:
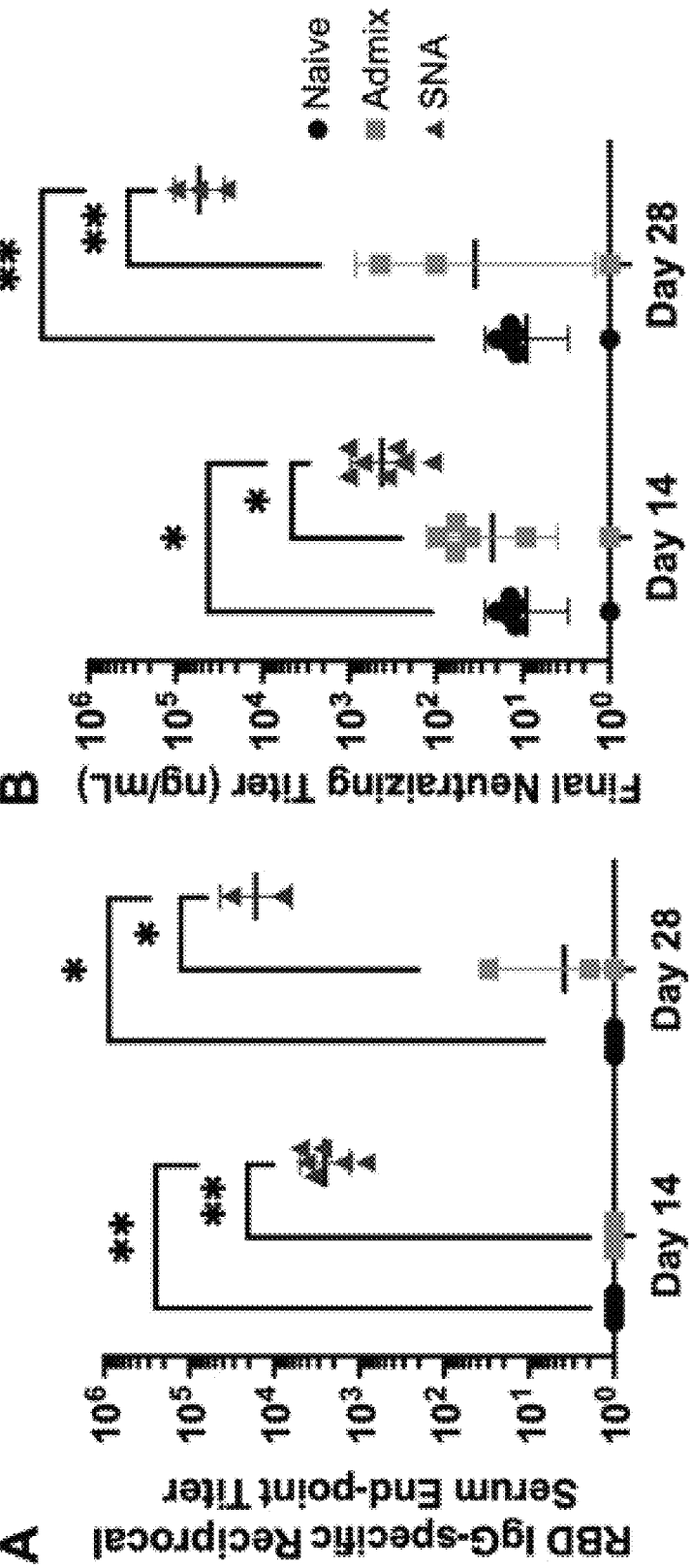

FIG. 14 shows prime-boost vaccination with two administrations enhances antibody production for all treatments, while SNA immunization is highest. Levels of (A) binding and (B) neutralizing antibodies on either day 14 (prime only on d0, sera collection on d14) or on day 28 (prime on d0, boost on d14, sera collection on d28). Graphs show mean and SD for n=3-6 per group. Analysis was done using a two-way ANOVA followed by a Tukey's multiple comparisons test. Only significant comparisons shown. *p<0.05; **p<0.01.

Figure 15:
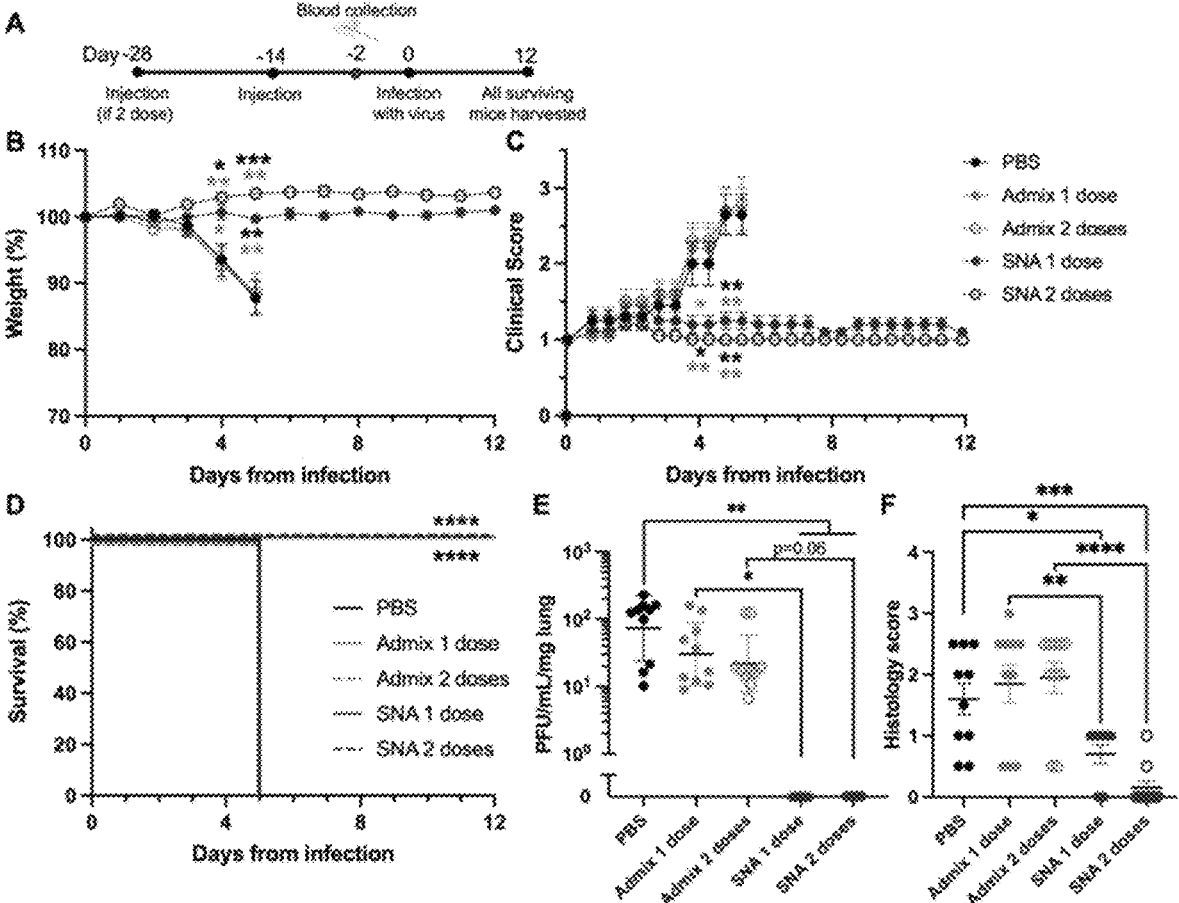

FIG. 15 shows results of experiments testing vaccine effectiveness using k18-hACE2 transgenic mice in a live viral SARS-CoV-2 challenge study. (A) Female and male mice (n=10 total per group, 5 of each gender) were treated with vaccine or control groups and infected with virus as per the schedule. (B) Vaccination with SNA of either 1 or 2 doses prevented any body weight loss, (C) improved clinical scores, and (D) prevented any mortality as compared to vehicle-mice (PBS) or admix mice treated with 1 or 2 doses when infected with SARS-CoV-2. On date of death, lungs were harvested and assessed for (E) viral load and (F) histopathology. (E) No detectable virus was observed for SNA mice treated with 1 or 2 doses. (F) Scores of neutrophil infiltration are lower in mice treated with SNA vaccine compared to mice treated with Admix vaccine or untreated. Comparisons made between PBS and all other groups, and Admix 1 dose versus SNA 1 dose, and Admix 2 dose versus SNA 2 dose. For panels B,C, statistical significance is shown above the date at which the analysis was performed. Colors correspond to the group that the SNA was compared to. Only significant comparisons were shown, and comparisons were made between SNA and PBS or the admix group with the same corresponding number of doses. For panels B, C, E, analysis was done using a Brown-Forsythe ANOVA followed by a Dunnett's multiple comparisons test. Panel F analysis was done using an ordinary one-way ANOVA followed by Sidak's multiple comparisons test. Panel D was analyzed using a log-rank test. *p<0.05; p<0.01; *p<0.001; ****p<0.0001.

Figure 16:
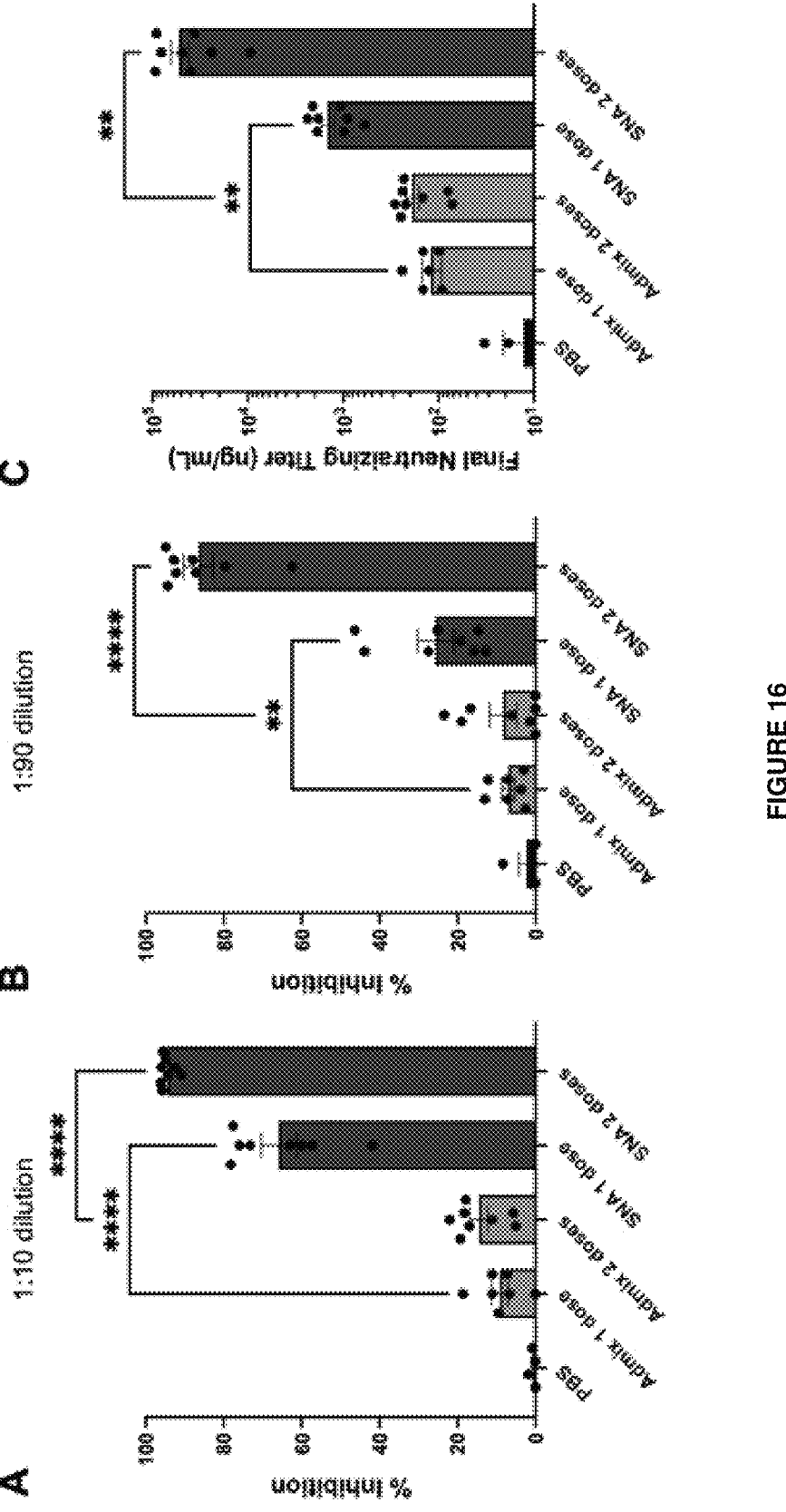

FIG. 16 shows results of experiments in which sera from k18-hACE2 transgenic mice were collected after immunization with different vaccines just prior to infection with virus to verify neutralizing antibody production. (A,B) Different dilutions of sera were assessed for antibody ability to inhibit RBD binding to ACE2 in a pseudovirus assay. SNA at either dose was significantly more effective at inhibition than admix. (C) Values from assay were fit to a standard curve to calculate a final neutralizing titer. p<0.01; **p<0.0001.

Figure 17:
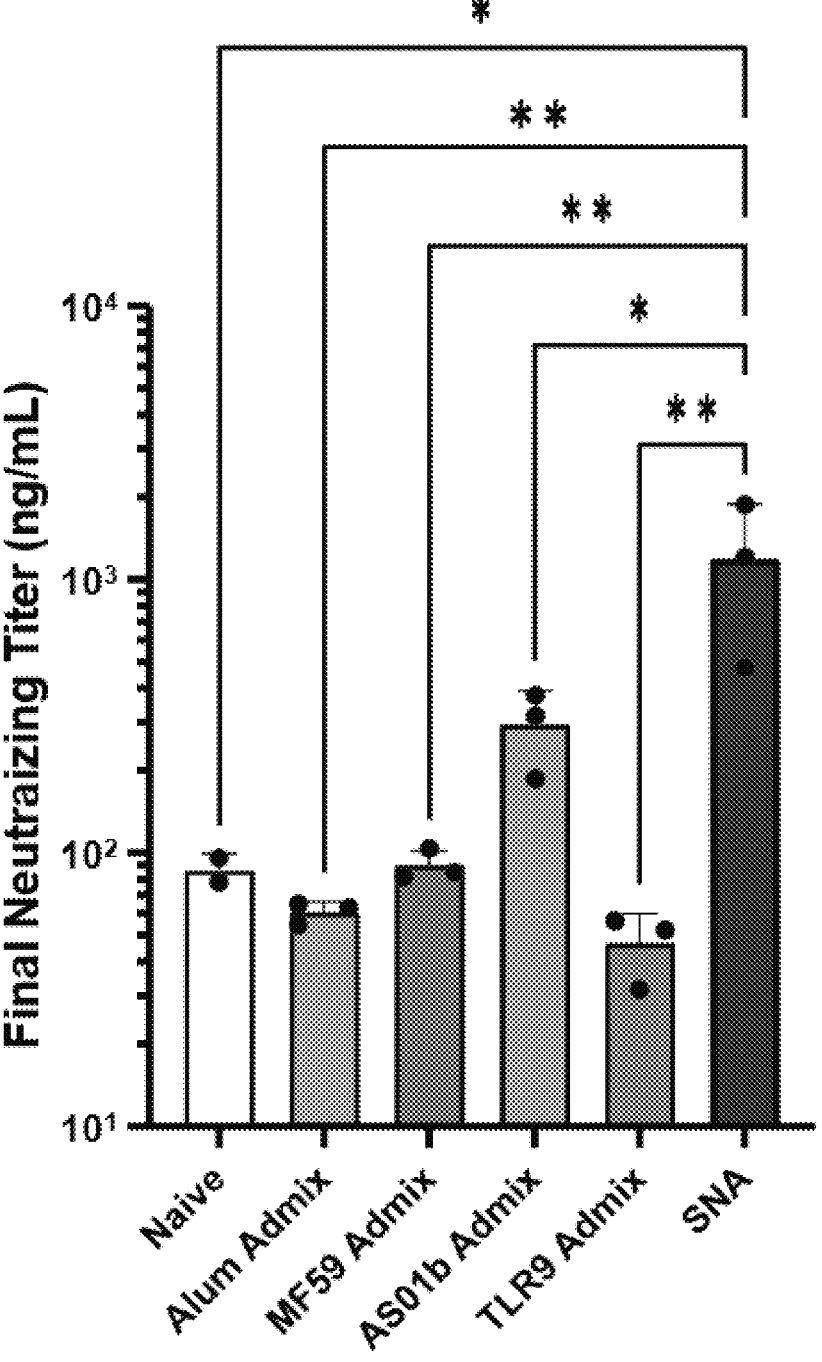

FIG. 17 shows the final neutralizing titer calculated in a pseudovirus inhibition study and fit to a standard curve using sera collected from C57BL/6 mice 21 days post a single prime injection. *p<0.05; **p<0.01.

Figure 18:
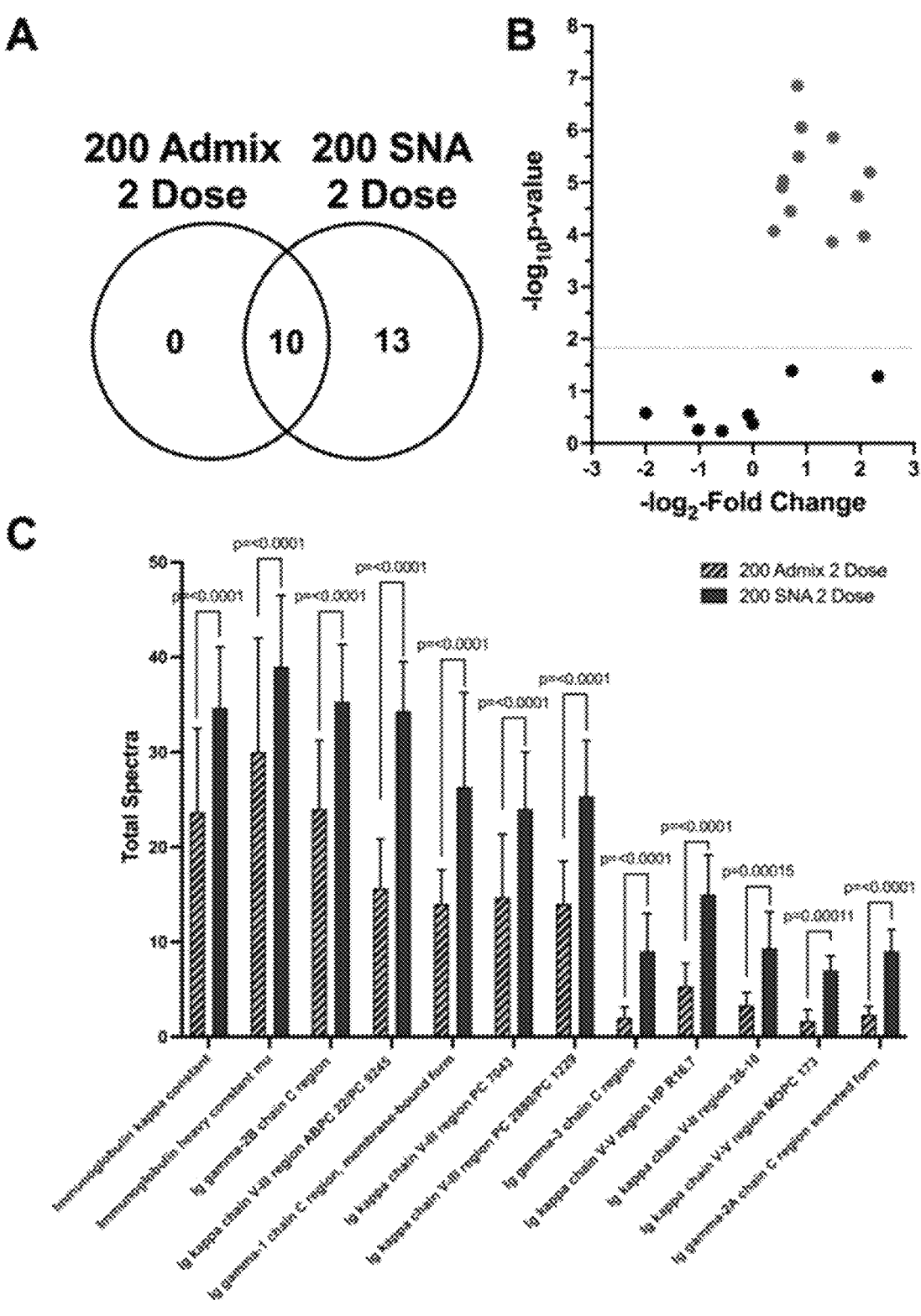

FIG. 18 shows (A) Quantitative profile of immunoglobulins between the 200 Admix 2 dose group and 200 SNA 2 dose group. (B) Volcano plot showing relative fold change and significance of different Igs when comparing the 200 Admix 2 dose against the 200 SNA 2 dose group. Red line indicates significance threshold. (C) The identified significant upregulated proteins were plotted as a function of total spectra with significance shown. Significance threshold=p<0.01585.

Figure 19:
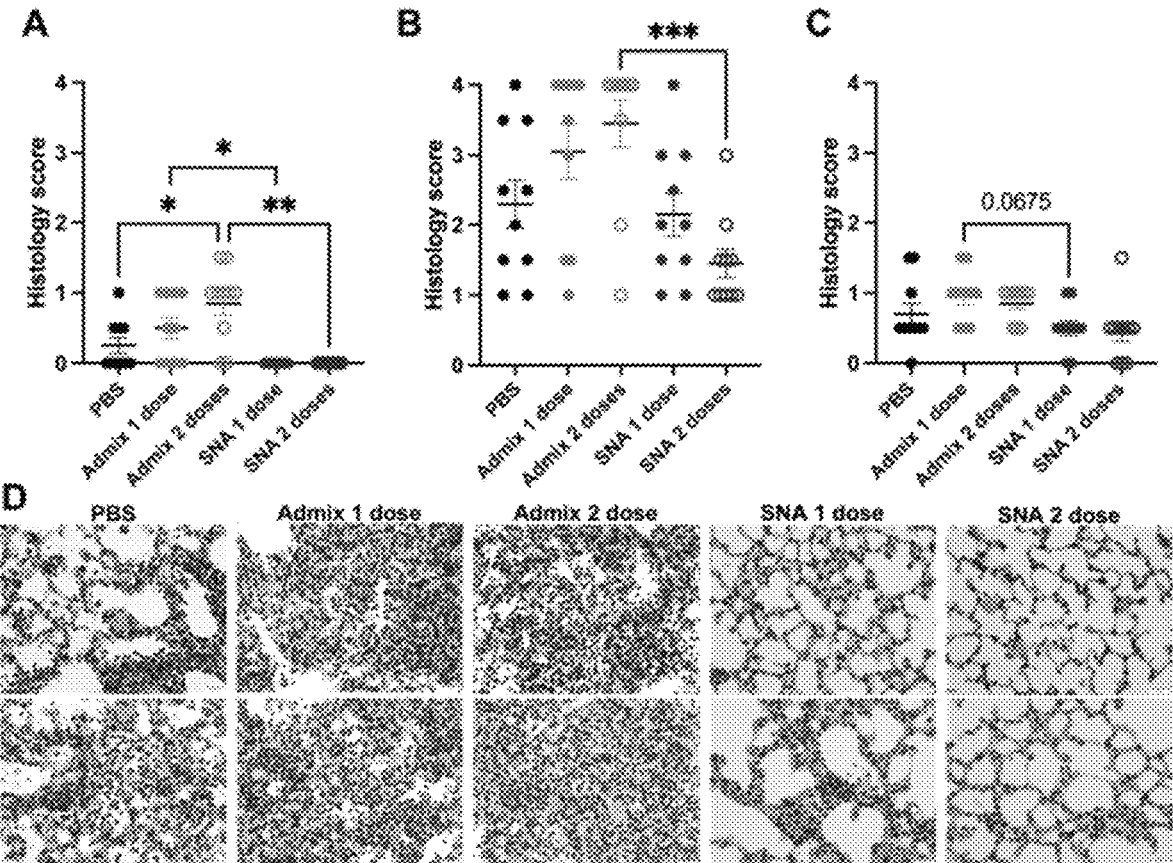

FIG. 19 shows lung histopathology analysis from k18-hACE2 transgenic mice immunized with vaccines and challenged with a lethal infection of SARS-CoV-2. Lungs were collected on date of death (day 5 for PBS and admix vaccine either dose, and day 12 for SNA vaccine either dose). Scoring of (A) necrosis, (B), mononuclear infiltrates, and (C) edema. (D) Representative images of lungs stained with hematoxylin and eosin. Two representative images shown per group (magnification: 400×). Scale bar=20 μm for all images. PBS group shows expansion of alveolar septae by inflammatory cells with solitary neutrophils in airspaces (red arrow, top image) and multiple foci of alveolar septal expansion by aggregates of mononuclear cells (blue arrows, bottom image). Admix 1 dose group shows dense inflammatory infiltrate including aggregates of neutrophils within airspaces (red arrow, top image) and diffuse expansion of alveolar septae by variably dense aggregates of mononuclear cells (blue arrows, bottom image). Admix 2 dose group shows dense inflammatory infiltrate including aggregates of neutrophils within airspaces (red arrow, top image) and diffuse mononuclear infiltrate consisting of variably sized lymphocytes with dense to open nuclear chromatin (blue arrows, bottom image) causing marked architectural distortion and expansion of alveolar septae. SNA 1 dose group shows rare, scattered neutrophils (red arrow, top image) sequestered in thin alveolar septae and foci of alveolar septal expansion by loose aggregates of mononuclear cells (blue arrows, bottom image). SNA 2 dose group shows thin alveolar septae with rare to absent neutrophils (top image) and focal expansion of alveolar septae by small loose aggregate of mononuclear cells (blue arrow, bottom image). *p<0.05; p<0.01; *p<0.001.

Figure 20:
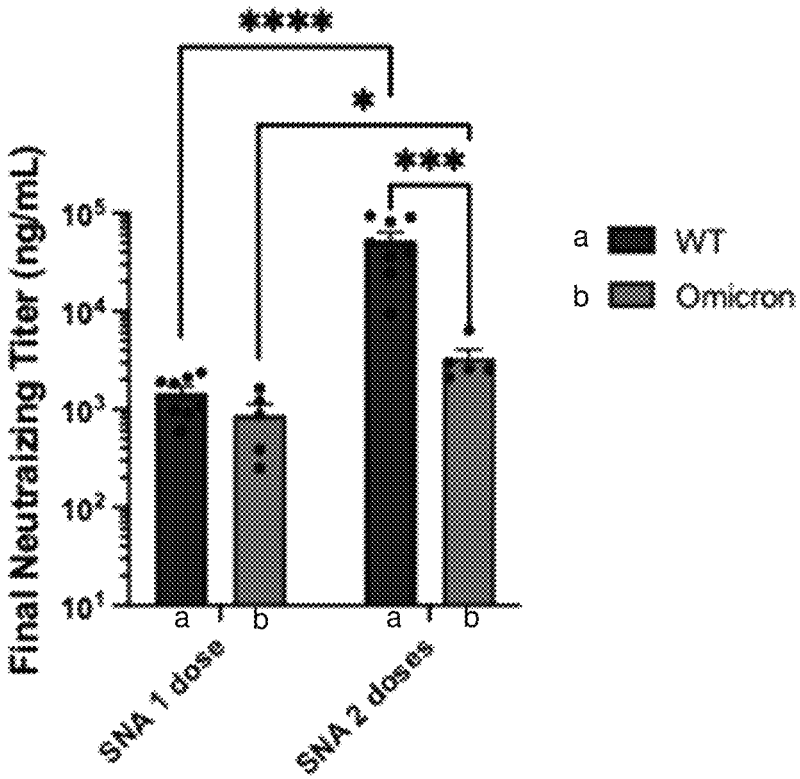

FIG. 20 shows the final neutralizing titer calculated in a pseudovirus inhibition study using either a wild-type (WT, blue) or Omicron (red) variant of the RBD protein and fit to a standard curve using sera collected from k18-hACE2 transgenic mice 12 days after a single prime injection (SNA 1 dose) and 12 days following a second boost injection (SNA 2 doses) following the same schedule as detailed in FIG. 15. *p<0.05; *p<0.001; **p<0.0001.

Figure 21:
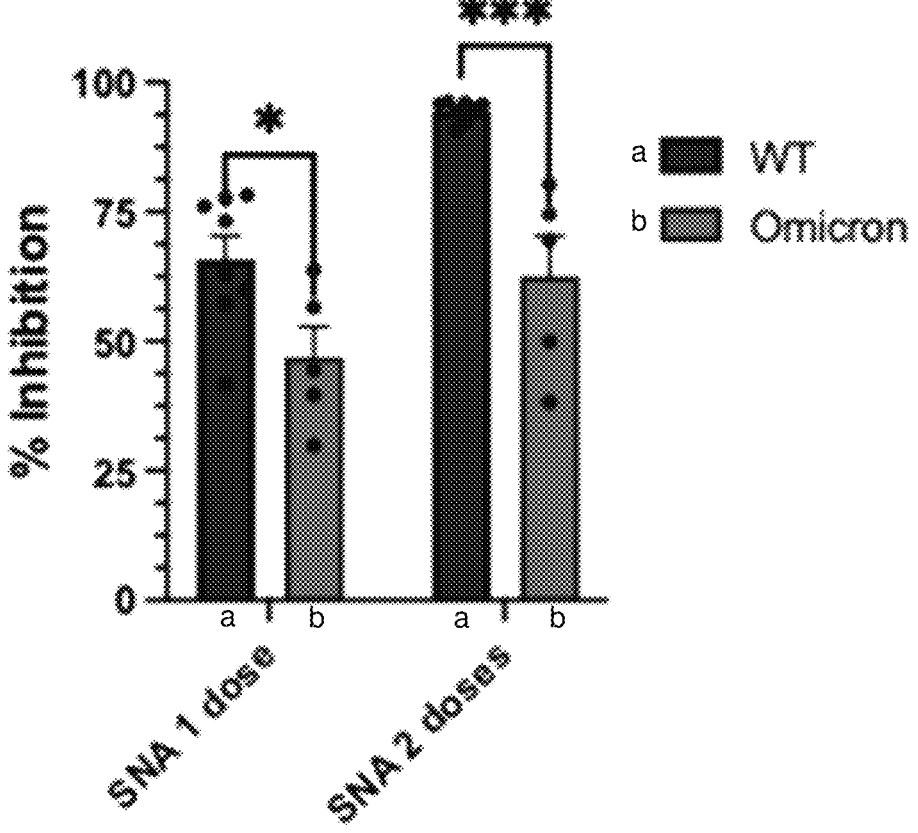

FIG. 21 shows the ability of sera collected from k18-hACE2 transgenic mice in the same experiment as FIG. 20 to have antibody ability to inhibit RBD binding to ACE2 in a pseudovirus assay. *p<0.05; ***p<0.001.

DETAILED DESCRIPTION

With respect to COVID-19 vaccination, there are currently over 90 COVID-19 vaccine candidates in clinical development worldwide. The vaccine target of the majority of these is the coronavirus' spike (S) protein, a heavily glycosylated trimeric class I fusion protein that coats the outside of the virus and is responsible for host cell entry. The S protein of SARS-CoV-2 shares high structural homology with SARS-CoV-1 and contains several subunits vital for viral entry into host cells through the angiotensin converting enzyme 2 (ACE2) receptor, including the S1 domain, the S2 domain, and the receptor binding domain (RBD). Thus, the S protein and its subunits, as well as accessible peptide sequences within these domains, are attractive vaccine antigen targets.

Accordingly, the present disclosure provides Spherical Nucleic Acids (SNAs), structures having a nanoparticle core densely functionalized with a radial arrangement of oligonucleotides, that can be utilized as antiviral vaccines. In this scenario, the core (e.g., a liposome or a lipid nanoparticle) comprises the viral immunogenic moiety and the oligonucleotide shell comprises oligonucleotides that serve as the immune system activator (e.g., adjuvant).

Terminology

All language such as "from," "to," "up to," "at least," "greater than," "less than," and the like include the number recited and refer to ranges which can subsequently be broken down into sub-ranges.

A range includes each individual member. Thus, for example, a group having 1-3 members refers to groups having 1, 2, or 3 members. Similarly, a group having 6 members refers to groups having 1, 2, 3, 4, or 6 members, and so forth.

As used in this specification and the appended claims, the articles "a" and "an" refer to one or to more than one (for example, to at least one) of the grammatical object of the article.

"About" and "approximately" shall generally mean an acceptable degree of error for the quantity measured given the nature or precision of the measurements. Exemplary degrees of error are within 20-25 percent (%), for example, within 20 percent, 10 percent, 5 percent, 4 percent, 3 percent, 2 percent, or 1 percent of the stated value or range of values.

The terms "polynucleotide" and "oligonucleotide" are interchangeable as used herein.

A "subject" is a vertebrate organism. The subject can be a non-human mammal (e.g., a mouse, a rat, or a non-human primate), or the subject can be a human subject.

The terms "administering", "administer", "administration", and the like, as used herein, refer to any mode of transferring, delivering, introducing, or transporting a SNA to a subject in need of treatment with such an agent. Such modes include, but are not limited to, oral, topical, intravenous, intraarterial, intraperitoneal, intramuscular, intratumoral, intradermal, intranasal, and subcutaneous administration.

As used herein, "treating" and "treatment" refers to any reduction in the severity and/or onset of symptoms associated with a viral infection. Accordingly, "treating" and "treatment" includes therapeutic and prophylactic measures. One of ordinary skill in the art will appreciate that any degree of protection from, or amelioration of, a viral infection is beneficial to a subject, such as a human patient. The quality of life of a patient is improved by reducing to any degree the severity of symptoms in a subject and/or delaying the appearance of symptoms.

As used herein, a "targeting oligonucleotide" is an oligonucleotide that directs a SNA to a particular tissue and/or to a particular cell type. In some embodiments, a targeting oligonucleotide is an aptamer. Thus, in some embodiments, a SNA of the disclosure comprises an aptamer attached to the exterior of the nanoparticle core, wherein the aptamer is designed to bind one or more receptors on the surface of a certain cell type.

As used herein, an "immunostimulatory oligonucleotide" is an oligonucleotide that can stimulate (e.g., induce or enhance) an immune response. Typical examples of immunostimulatory oligonucleotides are CpG-motif containing oligonucleotides, single-stranded RNA oligonucleotides, double-stranded RNA oligonucleotides, and double-stranded DNA oligonucleotides. A "CpG-motif" is a cytosine-guanine dinucleotide sequence. In any of the aspects or embodiments of the disclosure, the immunostimulatory oligonucleotide is a toll-like receptor (TLR) agonist (e.g., a toll-like receptor 9 (TLR9) agonist).

The term "inhibitory oligonucleotide" refers to an oligonucleotide that reduces the production or expression of proteins, such as by interfering with translating mRNA into proteins in a ribosome or that are sufficiently complementary to either a gene or an mRNA encoding one or more of targeted proteins, that specifically bind to (hybridize with) the one or more targeted genes or mRNA thereby reducing expression or biological activity of the target protein. Inhibitory oligonucleotides include, without limitation, isolated or synthetic short hairpin RNA (shRNA or DNA), an antisense oligonucleotide (e.g., antisense RNA or DNA, chimeric antisense DNA or RNA), miRNA and miRNA mimics, small interfering RNA (siRNA), DNA or RNA inhibitors of innate immune receptors, an aptamer, a DNAzyme, or an aptazyme.

An "antigenic composition" is a composition of matter suitable for administration to a human or animal subject (e.g., in an experimental or clinical setting) that is capable of eliciting a specific immune response, e.g., against an antigen, such as a viral antigen. In the context of this disclosure, the term antigenic composition will be understood to encompass compositions that are intended for administration to a subject or population of subjects for the purpose of eliciting a protective or palliative immune response against an antigen, such as a viral antigen.

The term "dose" as used herein refers to a measured portion of any of the SNAs of the disclosure (e.g., a SNA, antigenic composition, pharmaceutical formulation as described herein) taken by (administered to or received by) a subject at any one time.

An "immune response" is a response of a cell of the immune system, such as a B cell, T cell, or monocyte, to a stimulus, such as a SNA comprising a viral antigen as described herein. An immune response can be a B cell response, which results in the production of specific antibodies, such as antigen specific neutralizing antibodies. An immune response can also be a T cell response, such as a CD4+ response or a CD8+ response. B cell and T cell responses are aspects of a "cellular" immune response. An immune response can also be a "humoral" immune response, which is mediated by antibodies. In some cases, the response is specific for a particular antigen (that is, an "antigen-specific response"). A "protective immune response" is an immune response that inhibits a detrimental function or activity of an antigen, or decreases symptoms (including death) that result from the antigen. Protective in this context does not necessarily require that the subject is completely protected against infection. A protective response is achieved when the subject is protected from developing symptoms of disease, or when the subject experiences a lower severity of symptoms of disease. A protective immune response can be measured, for example, by immune assays using a serum sample from an immunized subject and testing the ability of serum antibodies for inhibition of pseudoviral binding, such as: pseudovirus neutralization assay (or surrogate virus neutralization test), ELISA-neutralization assay, antibody dependent cell-mediated cytotoxicity assay (ADCC), complement-dependent cytotoxicity (CDC), antibody dependent cell-mediated phagocytosis (ADCP), enzyme-linked immunospot (ELISpot). In addition, vaccine efficacy can be tested by measuring B or T cell activation after immunization, using flow cytometry (FACS) analysis or ELISpot assay. The protective immune response can be tested by measuring resistance to antigen challenge in vivo in an animal model. In humans, a protective immune response can be demonstrated in a population study, comparing measurements of symptoms, morbidity, mortality, etc. in treated subjects compared to untreated controls. Exposure of a subject to an immunogenic stimulus, such as a SNA comprising a viral antigen as described herein, elicits a primary immune response specific for the stimulus, that is, the exposure "primes" the immune response. A subsequent exposure, e.g., by immunization, to the stimulus can increase or "boost" the magnitude (or duration, or both) of the specific immune response. Thus, "boosting" a preexisting immune response by administering, e.g., an antigenic composition of the disclosure increases the magnitude of an antigen-specific response, (e.g., by increasing the breadth of produced antibodies (i.e., in the case of administering a booster that primes the immune system against a variant), by increasing antibody titer and/or affinity, by increasing the frequency of antigen specific B or T cells, by inducing maturation effector function, or a combination thereof). The "maturity and memory" of B and T cells may also be measured as an indicator of an immune response.

"Adjuvant" refers to a substance which, when added to a composition comprising an antigen, nonspecifically enhances or potentiates an immune response to the antigen in the recipient upon exposure. In any of the aspects or embodiments of the disclosure, the SNAs provided herein comprise immunostimulatory oligonucleotides (for example and without limitation, a toll-like receptor (TLR) agonist) as adjuvants and encapsulate viral antigens. Additional adjuvants contemplated for use according to the disclosure include aluminum (e.g., aluminum hydroxide), lipid-based adjuvant AS01B, alum, MF59, in addition to TLR agonists as described herein (e.g., CpG DNA, TLR7's imiquimod, TLR8's Motolimod, TLR4's MPLA4, TLR3's Poly (I:C), or a combination thereof).

An "effective amount" or a "sufficient amount" of a substance is that amount necessary to effect beneficial or desired results, including clinical results, and, as such, an "effective amount" depends upon the context in which it is being applied. In the context of administering a SNA of the disclosure, for example, an effective amount contains sufficient antigen to elicit an immune response. An effective amount can be administered in one or more doses as described further herein. Efficacy can be shown in an experimental or clinical trial, for example, by comparing results achieved with a substance of interest compared to an experimental control.

All references, patents, and patent applications disclosed herein are incorporated by reference with respect to the subject matter for which each is cited, which in some cases may encompass the entirety of the document.

Spherical Nucleic Acids (SNAs)

As described herein, spherical nucleic acids (SNAs) are a unique class of nanomaterials comprising a spherical or substantially spherical nanoparticle core functionalized with a highly oriented oligonucleotide shell. SNAs are highly modular and chemically well-defined architectures produced by chemical synthesis and programmed assembly, allowing for their rapid modification to incorporate novel viral antigens. This rational vaccinology approach is in stark contrast to the classical approach of vaccination with attenuated viruses and enables the generation of superior protective immune responses, as well as methods to rapidly produce vaccines at scale. More specifically, in some aspects the disclosure provides a spherical nucleic acid (SNA) comprising (a) a nanoparticle core; (b) a shell of oligonucleotides attached to the external surface of the nanoparticle core, the shell of oligonucleotides comprising one or more immunostimulatory oligonucleotides; and (c) a viral antigen encapsulated in the nanoparticle core. In various embodiments, the viral antigen is a full length protein, one or more fragments of the full length protein, a peptide, or a combination thereof. In further aspects, the disclosure provides a spherical nucleic acid (SNA) comprising (a) a nanoparticle core; (b) a shell of oligonucleotides attached to the external surface of the nanoparticle core, the shell of oligonucleotides comprising one or more immunostimulatory oligonucleotides; and (c) a viral antigen encapsulated in the nanoparticle core, wherein the viral antigen is receptor binding domain (RBD) (SEQ ID NO: 4), 51 subunit of Spike (SEQ ID NO: 5), SARS-CoV-2 Spike (SEQ ID NO: 2), a variant of any of the foregoing, or a combination thereof. In still further aspects, the disclosure provides a spherical nucleic acid (SNA) consisting of (a) a nanoparticle core; (b) a shell of immunostimulatory oligonucleotides attached to the external surface of the nanoparticle core; and (c) a viral antigen encapsulated in the nanoparticle core, wherein the viral antigen is receptor binding domain (RBD) (SEQ ID NO: 4), 51 subunit of Spike (SEQ ID NO: 5), SARS-CoV-2 Spike (SEQ ID NO: 2), a variant of any of the foregoing, or a combination thereof. In further aspects, the disclosure provides a spherical nucleic acid (SNA) comprising (a) a nanoparticle core; (b) a shell of oligonucleotides attached to the external surface of the nanoparticle core, the shell of oligonucleotides comprising one or more immunostimulatory oligonucleotides; and (c) a viral antigen encapsulated in the nanoparticle core, wherein the viral antigen comprises or consists of a sequence that is at least 80%, at least 85%, at least 90%, at least 95%, at least 99%, or 100% identical to receptor binding domain (RBD) (SEQ ID NO: 4), 51 subunit of Spike (SEQ ID NO: 5), SARS-CoV-2 Spike (SEQ ID NO: 2), SARS-CoV-2 surface glycoprotein (SEQ ID NO: 14), SARS-CoV-2 RBD (SEQ ID NO: 15), SARS-CoV-2 Omicron variant RBD (SEQ ID NO: 16), RBD (SEQ ID NO: 17), or a combination thereof. In still further aspects, the disclosure provides a spherical nucleic acid (SNA) consisting of (a) a nanoparticle core; (b) a shell of immunostimulatory oligonucleotides attached to the external surface of the nanoparticle core; and (c) a viral antigen encapsulated in the nanoparticle core, wherein the viral antigen comprises or consists of a sequence that is at least 80%, at least 85%, at least 90%, at least 95%, at least 99%, or 100% identical to receptor binding domain (RBD) (SEQ ID NO: 4), 51 subunit of Spike (SEQ ID NO: 5), SARS-CoV-2 Spike (SEQ ID NO: 2), SARS-CoV-2 surface glycoprotein (SEQ ID NO: 14), SARS-CoV-2 RBD (SEQ ID NO: 15), SARS-CoV-2 Omicron variant RBD (SEQ ID NO: 16), RBD (SEQ ID NO: 17), or a combination thereof.

The nanoparticle core is, in various embodiments, a liposomal core or a lipid nanoparticle core. Thus, the disclosure provides liposomal SNAs (LSNAs) and lipid nanoparticle SNAs (LNP-SNAs). The SNA architecture provides many chemical handles for the rapid synthesis and evaluation of modular and programmable antiviral vaccines. In turn, this enables one to tune several important antiviral vaccine design parameters, including spatial arrangement, presentation, and stoichiometric ratio of adjuvant and antigen [Bachmann et al., Nature Reviews Immunology 2010, 10 (11), 787-796]. Moreover, the inclusion of viral peptide subunits, whole proteins, and/or protein digests can be rapidly evaluated in the SNA format, allowing for the rapid development of new vaccines to counter the threat of antigenic shift and evolution in viral pathogens.

The composition of the shell of oligonucleotides is also highly modular, and can variously comprise DNA oligonucleotides, RNA oligonucleotides, modified forms thereof, or a combination thereof. The DNA oligonucleotides may be single-stranded, double-stranded, or a combination thereof. The RNA oligonucleotides may be single-stranded, double-stranded, or a combination thereof. The spherical architecture of the polynucleotide shell confers unique advantages over traditional nucleic acid delivery methods, including entry into nearly all cells independent of transfection agents and resistance to nuclease degradation. Furthermore, SNAs can penetrate biological barriers, including the blood-brain (see, e.g., U.S. Patent Application Publication No. 2015/0031745, incorporated by reference herein in its entirety) and blood-tumor barriers as well as the epidermis (see, e.g., U.S. Patent Application Publication No. 2010/0233270, incorporated by reference herein in its entirety).

In some aspects, a SNA of the disclosure comprises a nanoparticle core, a shell of oligonucleotides comprising DNA oligonucleotides and RNA oligonucleotides, and one or more viral antigens encapsulated in the nanoparticle core, wherein the viral antigens comprise a full length protein, one or more fragments of the full length protein, a peptide, or a combination thereof. In some embodiments, the shell of oligonucleotides comprises or consists of one or more immunostimulatory oligonucleotides. In further embodiments, the one or more immunostimulatory oligonucleotides is a toll-like receptor (TLR) agonist. In some embodiments, the TLR agonist is toll-like receptor 3 (TLR3) agonist, toll-like receptor 4 (TLR4) agonist, toll-like receptor 7 (TLR7) agonist, toll-like receptor 8 (TLR8) agonist, toll-like receptor 9 (TLR9) agonist, or a combination thereof. In still further embodiments the TLR agonist is a toll-like receptor 9 (TLR9) agonist. In some embodiments, the TLR9 agonist is CpG 7909 (5'-TCG TCG TTT TGT CGT TTT GTC GTT-3': SEQ ID NO: 7), CpG 1018 (5'-TGA CTG TGA ACG TTC GAG ATG A-3': SEQ ID NO: 8), CpG 1826 (murine TLR9 agonist)(5'-TCC ATG ACG TTC CTG ACG TT-3': SEQ ID NO: 9), or a combination thereof.

In general, nanoparticles can range in size from about 10 nm to about 150 nm in diameter, about 10 nm to about 140 nm in diameter, about 10 nm to about 130 nm in diameter, about 10 nm to about 120 nm in diameter, about 10 nm to about 110 nm in diameter, about 10 nm to about 100 nm in diameter, about 10 nm to about 90 nm in diameter, about 10 nm to about 80 nm in diameter, about 10 nm to about 70 nm in diameter, about 10 nm to about 60 nm in diameter, about 10 nm to about 50 nm in diameter, about 10 nm to about 40 nm in diameter, about 10 nm to about 30 nm in diameter, or about 10 nm to about 20 nm in diameter. In other aspects, the disclosure provides a plurality of nanoparticles, each nanoparticle having a substantially spherical geometry comprising a shell of oligonucleotides attached thereto, wherein one or more of the oligonucleotide in the shell is an immunostimulatory oligonucleotide (e.g., a Toll-Like Receptor (TLR) agonist), and wherein a viral antigen is encapsulated within the nanoparticle core. In these aspects, the size of the plurality of nanoparticles is from about 10 nm to about 150 nm (mean diameter), about 10 nm to about 140 nm in mean diameter, about 10 nm to about 130 nm in mean diameter, about 10 nm to about 120 nm in mean diameter, about 10 nm to about 110 nm in mean diameter, about 10 nm to about 100 nm in mean diameter, about 10 nm to about 90 nm in mean diameter, about 10 nm to about 80 nm in mean diameter, about 10 nm to about 70 nm in mean diameter, about 10 nm to about 60 nm in mean diameter, about 10 nm to about 50 nm in mean diameter, about 10 nm to about 40 nm in mean diameter, about 10 nm to about 30 nm in mean diameter, or about 10 nm to about 20 nm in mean diameter. In some embodiments, the diameter (or mean diameter for a plurality of nanoparticles) of the nanoparticles is from about 10 nm to about 150 nm, from about 30 to about 100 nm, or from about 40 to about 80 nm. In some embodiments, the size of the nanoparticles used in a method varies as required by their particular use or application. The variation of size is advantageously used to optimize, for example, the amount of surface area to which oligonucleotides can be attached. In further embodiments, a plurality of SNAs (e.g., LSNAs or LNP-SNAs) is produced and the SNAs in the plurality have a mean diameter of less than or equal to about 150 nanometers (e.g., about 10 nanometers to about 150 nanometers), or less than or equal to about 100 nanometers (e.g., about 10 nanometers to about 100 nanometers, or less than or equal to about 80 nanometers (e.g., about 10 nanometers to about 80 nanometers). In further embodiments, the nanoparticles in the plurality created by a method of the disclosure have a diameter or mean diameter of less than or equal to about 20 nanometers, or less than or equal to about 25 nanometers, or less than or equal to about 30 nanometers, or less than or equal to about 35 nanometers, or less than or equal to about 40 nanometers, or less than or equal to about 45 nanometers, or less than or equal to about 50 nanometers, or less than or equal to about 55 nanometers, or less than or equal to about 60 nanometers, or less than or equal to about 65 nanometers, or less than or equal to about 70 nanometers, or less than or equal to about 75 nanometers, or less than or equal to about 80 nanometers, or less than or equal to about 85 nanometers, or less than or equal to about 90 nanometers, or less than or equal to about 95 nanometers, or less than or equal to about 100 nanometers, or less than or equal to about 100 nanometers, or less than or equal to about 120 nanometers, or less than or equal to about 130 nanometers, or less than or equal to about 140 nanometers, or less than or equal to about 150 nanometers. It will be understood that the foregoing diameters of nanoparticles can apply to the diameter of the nanoparticle itself or to the diameter of the SNA (i.e., nanoparticle and oligonucleotides associated therewith).

Liposomal Spherical Nucleic Acids (LSNAs)

Liposomes are spherical, self-closed structures in a varying size range comprising one or several hydrophobic lipid bilayers with a hydrophilic core. The diameter of these lipid based carriers range from 0.15-1 micrometers, which is significantly higher than an effective therapeutic range of 20-100 nanometers. Liposomes termed small unilamellar vesicles (SUVs), can be synthesized in the 20-50 nanometer size range, but encounter challenges such as instability and aggregation leading to inter-particle fusion. This inter-particle fusion limits the use of SUVs in therapeutics. Liposomal spherical nucleic acids (LSNAs) comprise a liposomal core, a shell of oligonucleotides attached to the external surface of the liposomal core, the shell of oligonucleotides comprising one or more immunostimulatory oligonucleotides; and a viral antigen encapsulated in the liposomal core. Viral antigens contemplated for use according to the disclosure are further described herein below.

Liposomal particles, for example as disclosed in International Patent Application No. PCT/US2014/068429 (incorporated by reference herein in its entirety) are therefore provided by the disclosure. Liposomal particles of the disclosure have at least a substantially spherical geometry, an internal side and an external side, and comprise a plurality of lipid groups. In various embodiments, the plurality of lipid groups comprises a lipid selected from the group consisting of the phosphatidylcholine, phosphatidylglycerol, and phosphatidylethanolamine families of lipids. Lipids contemplated by the disclosure include, without limitation, 1,2-dioleoyl-sn-glycero-3-phosphocholine (DOPC), 1,2- dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1,2-dihexadecanoyl-sn-glycero-3-phosphoethanolamine (DPPE), 1,2-dioleoyl-sn-glycero-3-phospho-(1'-rac-glycerol) (DOPG), 1,2-distearoyl-sn-glycero-3-phosphoethanolamine (DSPE), cardiolipin, lipid A, monophosphoryl Lipid A (MPLA), or a combination thereof. In various embodiments, at least one oligonucleotide in the shell of oligonucleotides is attached to the exterior of the liposomal core through a lipid anchor group. In further embodiments, the lipid anchor group is attached to the 5' end or the 3' end of the at least one oligonucleotide. In still further embodiments, the lipid anchor group is tocopherol or cholesterol. Thus, in various embodiments, at least one of the oligonucleotides in the shell of oligonucleotides is an oligonucleotide-lipid conjugate containing a lipid anchor group, wherein said lipid anchor group is adsorbed into the lipid bilayer. In some embodiments, all of the oligonucleotides in the shell of oligonucleotides is an oligonucleotide-lipid conjugate containing a lipid anchor group, wherein said lipid anchor group is adsorbed into the lipid bilayer. In various embodiments, 10%, 20%, 30%, 40%, 50%, 60%, 70%, 80%, 90% or 100% of the oligonucleotides in the shell of oligonucleotides is attached (e.g., adsorbed) to the exterior of the liposomal core through a lipid anchor group. The lipid anchor group comprises, in various embodiments, tocopherol, palmitoyl, dipalmitoyl, stearyl, distearyl, or cholesterol. Methods of making oligonucleotides comprising a lipid anchor are disclosed herein. By way of example, first an oligonucleotide and phosphoramidite-modified-tocopherol are provided, and the oligonucleotide is then exposed to the phosphoramidite-modified-tocopherol to create the tocopherol modified oligonucleotide. While not meant to be limiting, any chemistry known to one of skill in the art can be used to attach the lipid anchor to the oligonucleotide, including amide linking or click chemistry.

With respect to the surface density of oligonucleotides on the surface of a LSNA of the disclosure, it is contemplated that a LSNA as described herein comprises from about 1 to about 400 oligonucleotides on its surface. In various embodiments, a LSNA comprises from about 10 to about 100, or from 10 to about 90, or from about 10 to about 80, or from about 10 to about 70, or from about 10 to about 60, or from about 10 to about 50, or from about 10 to about 40, or from about 10 to about 30, or from about 10 to about 20, or from about 50 to about 100, or from about 60 to about 100, or from about 70 to about 100, or from about 80 to about 100, or from about 90 to about 100, or from about 75 to about 200, or from about 75 to about 150, or from about 100 to about 200, or from about 150 to about 200 oligonucleotides on its surface. In further embodiments, a LSNA comprises or consists of about, at least about, or less than about 5, 10, 20, 30, 40, 50, 60, 70, 75, 80, 90, 100, 150, 160, 170, 180, 190, 200, 250, 300, 350, or 400 oligonucleotides on its surface. In some embodiments, a LSNA comprises or consists of 70 oligonucleotides on its surface. In some embodiments, a LSNA comprises or consists of 75 oligonucleotides on its surface. Additional surface densities for SNAs are described herein below.

Methods of making a LSNA are generally known (see, e.g., Wang, S.; Qin, L.; Yamankurt, G.; Skakuj, K.; Huang, Z.; Chen, P.-C.; Dominguez, D.; Lee, A.; Zhang, B.; Mirkin, C. A. Rational Vaccinology with Spherical Nucleic Acids. Proc. Natl. Acad. Sci. 2019, 116 (21), 10473-10481, incorporated by reference herein in its entirety).

Lipid Nanoparticle Spherical Nucleic Acids (LNP-SNAs)

Lipid nanoparticle spherical nucleic acids (LNP-SNAs) are comprised of a lipid nanoparticle core decorated with a shell of oligonucleotides. The lipid nanoparticle core comprises a viral antigen, an ionizable lipid, a phospholipid, a sterol, and a lipid-polyethylene glycol (lipid-PEG) conjugate. Viral antigens contemplated for use according to the disclosure are further described herein below. The shell of oligonucleotides is attached to the external surface of the lipid nanoparticle core, and in any of the aspects or embodiments of the disclosure comprises one or more immunostimulatory oligonucleotides. The spherical architecture of the oligonucleotide shell confers unique advantages over traditional nucleic acid delivery methods, including entry into nearly all cells independent of transfection agents, resistance to nuclease degradation, sequence-based function, targeting, and diagnostics.

In some embodiments, the ionizable lipid is dilinoleylmethyl-4-dimethylaminobutyrate (DLin-MC3-DMA), 2,2-Dilinoleyl-4-dimethylaminoethyl-[1,3]-dioxolane (DLin-KC2-DMA), C12-200, 1,2-dioleoyl-3-dimethylammonium-propane (DODAP), similar lipid/lipidoid structures, or a combination thereof. In some embodiments, the phospholipid is 1,2-distearoyl-sn-glycero-3-phosphocholine (DSPC), 1,2-Dihexadecanoyl phosphatidylcholine (DPPC), 1,2-dioleoyl-sn-glycero-3-phosphocholine (DOPC), 1,2-dioleoyl-sn-glycero-3-phosphoethanolamine (DOPE), monophosphoryl Lipid A (MPLA), or a combination thereof. In further embodiments, the sterol is 3β-Hydroxy-cholest-5-ene (Cholesterol), 9,10-Secocholesta-5,7,10(19)-trien-3β-ol (Vitamin D3), 9,10-Secoergosta-5,7,10(19),22-tetraen-3β-ol (Vitamin D2), Calcipotriol, 24-Ethyl-5,22-cholestadien-3β-ol (Stigmasterol), 22,23-Dihydrostigmasterol (β-Sitosterol), 3,28-Dihydroxy-lupeol (Betulin), Lupeol, Ursolic acid, Oleanolic acid, 24α-Methylcholesterol (Campesterol), 24-Ethylcholesta-5,24(28)E-dien-3β-ol (Fucosterol), 24-Methylcholesta-5,22-dien-3β-ol (Brassicasterol), 24-Methylcholesta-5,7,22-trien-3β-ol (Ergosterol), 9,11-Dehydroergosterol, Daucosterol, or any of the foregoing sterols modified with one or more amino acids. In some embodiments, the lipid-polyethylene glycol (lipid-PEG) conjugate comprises 2000 Dalton (Da) polyethylene glycol. In further embodiments, the lipid-polyethylene glycol (lipid-PEG) conjugate is lipid-PEG-maleimide. In still further embodiments, the lipid-PEG-maleimide is 1,2-dipalmitoryl-sn-glycero-3-phosphoethanolamine (DPPE) conjugated to 2000 Da polyethylene glycol maleimide, 1,2-dimyristoyl-sn-glycero-3-phosphoethanolamine (DMPE) conjugated to 2000 Da polyethylene glycol maleimide, or a combination thereof.

In any of the aspects or embodiments of the disclosure an oligonucleotide is attached to the exterior of a lipid nanoparticle core via a covalent attachment of the oligonucleotide to a lipid-polyethylene glycol (lipid-PEG) conjugate. In various embodiments, 10%, 20%, 30%, 40%, 50%, 60%, 70%, 80%, 90% or 100% of the oligonucleotides in the shell of oligonucleotides are covalently attached to the exterior of the lipid nanoparticle core through the lipid-PEG conjugate. In various embodiments, one or more oligonucleotides in the oligonucleotide shell is attached (e.g., adsorbed) to the exterior of the lipid nanoparticle core through a lipid anchor group as described herein. In various embodiments, 10%, 20%, 30%, 40%, 50%, 60%, 70%, 80%, 90% or 100% of the oligonucleotides in the shell of oligonucleotides is attached (e.g., adsorbed) to the exterior of the lipid nanoparticle core through a lipid anchor group as described herein. The lipid anchor group is, in various embodiments, attached to the 5'- or 3'-end of the oligonucleotide. In various embodiments, the lipid anchor group is tocopherol, palmitoyl, dipalmitoyl, stearyl, distearyl, or cholesterol.

Viral Antigens

As described herein, a spherical nucleic acid (SNA) of the disclosure comprises (a) a nanoparticle core; (b) a shell of oligonucleotides attached to the external surface of the nanoparticle core, the shell of oligonucleotides comprising one or more immunostimulatory oligonucleotides; and (c) a viral antigen encapsulated in the nanoparticle core. In various embodiments, the viral antigen is a full length viral antigen protein, a variant of a full length viral antigen protein, a peptide derived from the viral antigen, one or more fragments of a full length viral antigen protein, or a combination thereof. The viral antigen is, in various embodiments, an antigen derived from a coronavirus (e.g., SARS-CoV-2). In various embodiments, the viral antigen is derived from an influenza virus, a herpes virus (e.g., herpes zoster), a human papilloma virus (HPV), a human immunodeficiency virus (HIV), measles, mumps, and Rubella (MMR), or a combination thereof. More specifically, in various embodiments, the viral antigen that is encapsulated in the nanoparticle core of a SNA is receptor binding domain (RBD) (SEQ ID NO: 4, SEQ ID NO: 15, SEQ ID NO: 17, or a combination thereof), 51 subunit of Spike (SEQ ID NO: 5), SARS-CoV-2 Spike (SEQ ID NO: 2), a variant or fragment of any of the foregoing, a peptide derived from any of the foregoing, or a combination thereof. In further embodiments, the viral antigen is SARS-CoV-2 surface glycoprotein (SEQ ID NO: 14) or a variant thereof. In some embodiments, the viral antigen is SARS-CoV-2 Omicron variant RBD (SEQ ID NO: 16) or a variant thereof. In some embodiments, the viral antigen is SEQ ID NO: 10 or a variant or fragment thereof. In still further embodiments, the viral antigen is or is derived from SARS-CoV-2 envelope protein, SARS-CoV-2 nucleocapsid protein, SARS-CoV-2 membrane protein, a variant or fragment of any of the foregoing, or a combination thereof. In some embodiments, a mRNA that encodes for any of the viral antigens of the disclosure is encapsulated in the nanoparticle core, either alone or in combination with one or more protein viral antigens of the disclosure. As used herein, a "variant" refers to a genetic variant that comprises one or more mutations relative to a wild type amino acid sequence. Thus, in any of the aspects or embodiments of the disclosure, a nucleotide or amino acid sequence of a viral antigen the disclosure comprises or consists of a sequence that is at least 80%, at least 85%, at least 90%, at least 95%, at least 99%, or 100% identical to a reference or wild type sequence. In any of the aspects or embodiments of the disclosure, the viral antigen comprises or consists of a nucleotide or an amino acid sequence that is at least 80%, at least 85%, at least 90%, at least 95%, at least 99%, or 100% identical to a reference or wild type sequence. In various embodiments, the viral antigen that is encapsulated in the nanoparticle core of a SNA comprises or consists of a sequence that is at least 80%, at least 85%, at least 90%, at least 95%, at least 99%, or 100% identical to receptor binding domain (RBD) (SEQ ID NO: 4), 51 subunit of Spike (SEQ ID NO: 5), SARS-CoV-2 Spike (SEQ ID NO: 2), SARS-CoV-2 surface glycoprotein (SEQ ID NO: 14), SARS-CoV-2 RBD (SEQ ID NO: 15), SARS-CoV-2 Omicron variant RBD (SEQ ID NO: 16), RBD (SEQ ID NO: 17), or a combination thereof.

TABLE 1

Examples of viral antigens for use according to the disclosure.

| Viral Antigen | Sequence | SEQ ID NO: |
|---|---|---|
| SARS-CoV-2 Spike | Protein | 2 |
| receptor binding domain (RBD) | Protein | 4 |
| S1 subunit of Spike | Protein | 5 |
| Peptide derived from S2 domain | Protein | 6 |
| SARS-CoV-2 surface glycoprotein | Protein | 14 |
| SARS-CoV-2 RBD | Protein | 15 |
| SARS-CoV-2 Omicron variant RBD | Protein | 16 |
| RBD | Protein | 17 |

The DNA sequence of SARS-CoV-2 Spike is shown in SEQ ID NO: 1, and the DNA sequence of the receptor binding domain (RBD) is shown in SEQ ID NO: 3.

In various embodiments, the viral antigen that is encapsulated in the nanoparticle core is a full length protein, a peptide, one or more fragments of a full length protein, a variant thereof, or a combination thereof. Thus, in some embodiments, the viral antigen is SEQ ID NO: 2, a peptide derived from SEQ ID NO: 2, one or more fragments of SEQ ID NO: 2, a variant of SEQ ID NO: 2, or a combination thereof. In further embodiments, the viral antigen is SEQ ID NO: 4, a peptide derived from SEQ ID NO: 4, one or more fragments of SEQ ID NO: 4, a variant of SEQ ID NO: 4, or a combination thereof. In further embodiments, the viral antigen is SEQ ID NO: 5, a peptide derived from SEQ ID NO: 5, one or more fragments of SEQ ID NO: 5, a variant of SEQ ID NO: 5, or a combination thereof. In further embodiments, the viral antigen is SEQ ID NO: 6, a peptide derived from SEQ ID NO: 6, one or more fragments of SEQ ID NO: 6, a variant of SEQ ID NO: 6, or a combination thereof. In further embodiments, the viral antigen is SEQ ID NO: 14, a peptide derived from SEQ ID NO: 14, one or more fragments of SEQ ID NO: 14, a variant of SEQ ID NO: 14, or a combination thereof. In further embodiments, the viral antigen is SEQ ID NO: 15, a peptide derived from SEQ ID NO: 15, one or more fragments of SEQ ID NO: 15, a variant of SEQ ID NO: 15, or a combination thereof. In further embodiments, the viral antigen is SEQ ID NO: 16, a peptide derived from SEQ ID NO: 16, one or more fragments of SEQ ID NO: 16, a variant of SEQ ID NO: 16, or a combination thereof. In further embodiments, the viral antigen is SEQ ID NO: 17, a peptide derived from SEQ ID NO: 17, one or more fragments of SEQ ID NO: 17, a variant of SEQ ID NO: 17, or a combination thereof. As described herein, combinations of viral antigens (and/or peptides, fragments, or variants thereof) are also contemplated for encapsulation in a nanoparticle core of the disclosure. In some embodiments, the peptide is KRSFIEDLLFNKV (SEQ ID NO: 6), which is a minimally shielded sequence of the S2 domain implicated as a potential COVID-19 epitope located in the fusion protein (FP) region of the spike protein's second cleavage site (S2'). In further embodiments, the viral antigen is a variant of a full length protein, a peptide, one or more fragments of a full length protein, or a combination thereof. As used herein a "fragment" of a protein is meant to refer to any portion of a protein smaller than the full-length protein or protein expression product. Fragments of a protein are produced, for example and without limitation, via digestion of a protein.

As used herein, "protein" is used interchangeably with "polypeptide" and refers to one or more polymers of amino acid residues. In various embodiments of the disclosure, a nanoparticle core comprises or consists of a single protein (i.e., a single polymer of amino acids), a multimeric protein, a peptide, or a synthetic fusion protein of two or more proteins. Synthetic fusion proteins include, without limitation, an expressed fusion protein (expressed from a single gene) and post-expression fusions where proteins are conjugated together chemically. The term "peptide" typically refers to a short (e.g., about 2-50 amino acids in length) polymer of amino acids.

In some embodiments, a combination of viral antigens is encapsulated in the nanoparticle core of a SNA of the disclosure. Thus, in some embodiments a peptide and a full length protein are encapsulated in the nanoparticle core of a SNA of the disclosure.

Regarding the amount of viral antigen that is encapsulated in the nanoparticle core of a SNA, the disclosure contemplates that at least about 0.25 milligram (mg) of the viral antigen is encapsulated in the nanoparticle core per micromole (μmol) of oligonucleotides in the shell of oligonucleotides that is attached to the external surface of the nanoparticle core. In some embodiments, about 0.5 mg of the viral antigen is encapsulated in the nanoparticle core per micromole (μmol) of oligonucleotides in the shell of oligonucleotides. In some embodiments, about 0.25 mg to about 10 mg of the viral antigen is encapsulated in the nanoparticle core per micromole (μmol) of oligonucleotides in the shell of oligonucleotides. In some embodiments, about 0.5 mg to about 10 mg of the viral antigen is encapsulated in the nanoparticle core per micromole (μmol) of oligonucleotides in the shell of oligonucleotides. In further embodiments, about 1 mg to about 10 mg of the viral antigen is encapsulated in the nanoparticle core per micromole (μmol) of oligonucleotides in the shell of oligonucleotides. In still further embodiments, about, at least about, or less than about 0.25 mg, 0.3 mg, 0.4 mg, 0.5 mg, 0.6 mg, 0.7 mg, 0.8 mg, 0.9 mg, 1 mg, 1.1 mg, 1.2 mg, 1.3 mg. 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, or more of the viral antigen is encapsulated in the nanoparticle core per micromole (μmol) of oligonucleotides in the shell of oligonucleotides. In further embodiments, about 1 mg to about 10 mg, about 1 mg to about 9 mg, about 1 mg to about 8 mg, about 1 mg to about 7 mg, about 1 mg to about 6 mg, about 1 mg to about 5 mg, about 1 mg to about 4 mg, about 1 mg to about 3 mg, about 1 mg to about 2 mg, about 0.25 mg to about 10 mg, about 0.25 mg to about 9 mg, about 0.25 mg to about 8 mg, about 0.25 mg to about 7 mg, about 0.25 mg to about 6 mg, about 0.25 mg to about 5 mg, about 0.25 mg to about 4 mg, about 0.25 mg to about 3 mg, about 0.25 mg to about 2 mg, about 0.25 mg to about 0.5 mg, about 0.5 mg to about 10 mg, about 0.5 mg to about 9 mg, about 0.5 mg to about 8 mg, about 0.5 mg to about 7 mg, about 0.5 mg to about 6 mg, about 0.5 mg to about 5 mg, about 0.5 mg to about 4 mg, about 0.5 mg to about 3 mg, about 0.5 mg to about 2 mg, or about 0.5 mg to about 1 mg of the viral antigen is encapsulated in the nanoparticle core per micromole (μmol) of oligonucleotides in the shell of oligonucleotides.

The amount of viral antigen that is encapsulated in the nanoparticle core of a SNA may also be described as a ratio of adjuvant (e.g., immunostimulatory oligonucleotides in the shell of oligonucleotides) to viral antigen. For example, the ratio can be given as the number of immunostimulatory oligonucleotides in the shell of oligonucleotides to the number of viral antigen molecules (e.g., protein viral antigen molecules) encapsulated in the nanoparticle core In various embodiments, the ratio of adjuvant (e.g., immunostimulatory oligonucleotides in the shell of oligonucleotides) to viral antigen is about 5:1 to about 70:1. In further embodiments, the ratio of adjuvant (e.g., immunostimulatory oligonucleotides in the shell of oligonucleotides) to viral antigen is, is about, is at least about, or is less than about 5:1, 10:1, 15:1, 16:1, 20:1, 25:1, 30:1, 32:1, 35:1, 40:1, 43:1, 45:1, 50:1, 55:1, 60:1, 65:1, or 70:1. In some embodiments, the shell of oligonucleotides comprises one or more oligonucleotides (e.g., a targeting oligonucleotide and/or an inhibitory oligonucleotide) in addition to the immunostimulatory oligonucleotides. In such embodiments, the ratio is calculated as the number of oligonucleotides in the shell of oligonucleotides to the number of viral antigens encapsulated in the nanoparticle core.

Oligonucleotides

The disclosure provides spherical nucleic acids (e.g., LSNAS, LNP-SNAs) comprising a nanoparticle core, a viral antigen encapsulated in the nanoparticle core, and a shell of oligonucleotides attached to the exterior of the nanoparticle core, the shell of oligonucleotides comprising one or more immunostimulatory oligonucleotides. In various embodiments, the shell of oligonucleotides comprises an inhibitory oligonucleotide, a targeting oligonucleotide, or a combination thereof. Oligonucleotides contemplated for use according to the disclosure include those attached to a nanoparticle core through any means (e.g., covalent or non-covalent attachment). Oligonucleotides of the disclosure include, in various embodiments, DNA oligonucleotides, RNA oligonucleotides, modified forms thereof, or a combination thereof. In any aspects or embodiments described herein, an oligonucleotide is single-stranded, double-stranded, or partially double-stranded. In any aspects or embodiments of the disclosure, an oligonucleotide comprises a detectable marker.

As described herein, modified forms of oligonucleotides are also contemplated by the disclosure which include those having at least one modified internucleotide linkage. In some embodiments, the oligonucleotide is all or in part a peptide nucleic acid. Other modified internucleoside linkages include at least one phosphorothioate linkage. Still other modified oligonucleotides include those comprising one or more universal bases. "Universal base" refers to molecules capable of substituting for binding to any one of A, C, G, T and U in nucleic acids by forming hydrogen bonds without significant structure destabilization. The oligonucleotide incorporated with the universal base analogues is able to function, e.g., as a probe in hybridization. Examples of universal bases include but are not limited to 5'-nitroindole-2'-deoxyriboside, 3-nitropyrrole, inosine and hypoxanthine.

The term "nucleotide" or its plural as used herein is interchangeable with modified forms as discussed herein and otherwise known in the art. The term "nucleobase" or its plural as used herein is interchangeable with modified forms as discussed herein and otherwise known in the art. Nucleotides or nucleobases comprise the naturally occurring nucleobases A, G, C, T, and U. Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, oligonucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide".

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899;

5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216, 141; 5,235,033; 5,264,562; 5,264,564; 5,405,938; 5,434, 257; 5,466,677; 5,470,967; 5,489,677; 5,541,307; 5,561, 225; 5,596,086; 5,602,240; 5,610,289; 5,602,240; 5,608, 046; 5,610,289; 5,618,704; 5,623,070; 5,663,312; 5,633, 360; 5,677,437; 5,792,608; 5,646,269 and 5,677,439, the disclosures of which are incorporated herein by reference in their entireties.

In still further embodiments, oligonucleotide mimetics wherein both one or more sugar and/or one or more internucleotide linkage of the nucleotide units are replaced with "non-naturally occurring" groups. The bases of the oligonucleotide are maintained for hybridization. In some aspects, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

In still further embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N ($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligonucleotide consists of 2 to 4, desirably 3, groups/atoms selected from —$CH_2$—, —O—, S, $NR^H$—, >C=O, >C=$NR^H$, >C=S, —Si(R")$_2$—, —SO—, —S(O)$_2$—, —P(O)$_2$—, —PO($BH_3$)—, —P(O,S)—, —P(S)$_2$—, —PO(R")—, —PO(O$CH_3$)—, and —PO (NHR$^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C (=$NR^H$)—$NR^H$—, —$NR^H$—CO—$CH_2$—$NR^H$—O— CO—O—, —O—CO—$CH_2$—O—, —O—$CH_2$—CO— O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$— $NR^H$—O—, —$CH_2$—O—N=(including $R^5$ when used as a linkage to a succeeding monomer), $—CH_2—O—NR^H—$, $—CO—NR^H—CH_2—$, $—CH_2—NR^H—O—$, $—CH_2—NR^H—CO—$, $—O—NR^H—CH_2—$, $—O—NR^H$, $—O—CH_2—S—$, $—S—CH_2—O—$, $—CH_2—CH_2—S—$, $—O—CH_2—CH_2—S—$, $—S—CH_2—CH=$(including $R^5$ when used as a linkage to a succeeding monomer), $—S—CH_2—CH_2—$, $—S—CH_2—CH_2—O—$, $—S—CH_2—CH_2—S—$, $—CH_2—S—CH_2—$, $—CH_2—SO—CH_2—$, $—CH_2—SO_2—CH_2—$, $—O—SO—O—$, $—O—S(O)_2—O—$, $—O—S(O)_2—CH_2—$, $—O—S(O)_2—NR^H$, $—NR^H—S(O)_2—CH_2—$; $—O—S(O)_2—CH_2—$, $—O—P(O)_2—O—$, $—O—P(O,S)—O—$, $—O—P(S)_2—O—$, $—S—P(O)_2—O—$, $—S—P(O,S)—O—$, $—S—P(S)_2—O—$, $—O—P(O)_2—S—$, $—O—P(O,S)—S—$, $—O—P(S)_2—S—$, $—S—P(O)_2—S—$, $—S—P(O,S)—S—$, $—S—P(S)_2—S—$, $—O—PO(R'')—O—$, $—O—PO(OCH_3)—O—$, $—O—PO(O\ CH_2CH_3)—O—$, $—O—PP(O\ CH_2CH_2S—R)—O—$, $—O—PO(BH_3)—O—$, $—O—PO(NHR^N)—O—$, $—O—P(O)_2—NR^H\ H—$, $—NR^H—P(O)_2—O—$, $—O—P(O,NR^H)—O—$, $—CH_2—P(O)_2—O—$, $—O—P(O)_2—CH_2—$, and $—O—Si(R'')_2—O—$; among which $—CH_2—CO—NR^H—$, $—CH_2—NR^H—O—$, $—S—CH_2—O—$, $—O—P(O)_2—O—O—P(—O,S)—O—$, $—O—P(S)_2—O—$, $—NR^H\ P(O)_2—O—$, $—O—P(O,NR^H)—O—$, $—O—PO(R'')—O—$, $—O—PO(CH_3)—O—$, and $—O—PO(NHR^N)—O—$, where $R^H$ is selected form hydrogen and $C_{1-4}$-alkyl, and R'' is selected from $C_{1-6}$-alkyl and phenyl, are contemplated. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443.

Still other modified forms of oligonucleotides are described in detail in U.S. patent application No. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_n$ $ON[(CH_2)_nCH_3]_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, or an RNA cleaving group. In one aspect, a modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. Other modifications include 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Still other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In some aspects, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene ($—CH_2—)_n$ group bridging the 2' oxygen atom and the 4' carbon atom wherein n is 1 or 2. LNAs and preparation thereof are described in WO 98/39352 and WO 99/14226.

Modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5, 4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing binding affinity and include 5-substituted pyrimidines, 6-azapyrimidines and N-2, N-6 and 0-6 substituted purines, including 2-amino-propyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711;

5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucle-otides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kos-turko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

In various aspects, an oligonucleotide of the disclosure, or a modified form thereof, is generally about 5 nucleotides to about 4000 nucleotides in length. More specifically, an oligonucleotide of the disclosure is about 5 to about 4000 nucleotides in length, about 5 to about 3000 nucleotides in length, about 5 to about 2000 nucleotides in length, about 5 to about 1000 nucleotides in length, about 5 to about 900 nucleotides in length, about 5 to about 800 nucleotides in length, about 5 to about 700 nucleotides in length, about 5 to about 600 nucleotides in length, about 5 to about 500 nucleotides in length about 5 to about 450 nucleotides in length, about 5 to about 400 nucleotides in length, about 5 to about 350 nucleotides in length, about 5 to about 300 nucleotides in length, about 5 to about 250 nucleotides in length, about 5 to about 200 nucleotides in length, about 5 to about 150 nucleotides in length, about 5 to about 100, about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, about 10 to about 4000 nucleotides in length, about 10 to about 3000 nucleotides in length, about 10 to about 2000 nucleotides in length, about 10 to about 1000 nucleotides in length, about 10 to about 900 nucleotides in length, about 10 to about 800 nucleotides in length, about 10 to about 700 nucleotides in length, about 10 to about 600 nucleotides in length, about 10 to about 500 nucleotides in length about 10 to about 450 nucleotides in length, about 10 to about 400 nucleotides in length, about 10 to about 350 nucleotides in length, about 10 to about 300 nucleotides in length, about 10 to about 250 nucleotides in length, about 10 to about 200 nucleotides in length, about 10 to about 150 nucleotides in length, about 10 to about 100 nucleotides in length, about 10 to about 90 nucleotides in length, about 10 to about 80 nucleotides in length, about 10 to about 70 nucleotides in length, about 10 to about 60 nucleotides in length, about 10 to about 50 nucleotides in length about 10 to about 45 nucleotides in length, about 10 to about 40 nucleotides in length, about 10 to about 35 nucleotides in length, about 10 to about 30 nucleotides in length, about 10 to about 25 nucleotides in length, about 10 to about 20 nucleotides in length, about 10 to about 15 nucleotides in length, about 18 to about 28 nucleotides in length, about 15 to about 26 nucleotides in length, and all oligonucleotides intermediate in length of the sizes specifically disclosed to the extent that the oligonucleotide is able to achieve the desired result. In further embodiments, an oligonucleotide of the disclosure is about 5 to about 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 40 nucleotides in length, about 5 to about 30 nucleotides in length, about 5 to about 20 nucleotides in length, about 5 to about 10 nucleotides in length, and all oligonucleotides intermediate in length of the sizes specifically disclosed to the extent that the oligonucleotide is able to achieve the desired result. Accordingly, in various embodiments, an oligonucleotide of the disclosure is or is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 300, 400, 500, 600, 700, 800, 900, 1000, 2000, 3000, 4000, or more nucleotides in length. In further embodiments, an oligonucleotide of the disclosure is less than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 1500, 2000, 2500, 3000, 4000, or more nucleotides in length. In various embodiments, the shell of oligonucle-otides attached to the exterior of the nanoparticle core of the SNA comprises a plurality of oligonucleotides that all have the same length/sequence, while in some embodiments, the plurality of oligonucleotides comprises one or more oligo-nucleotide that have a different length and/or sequence relative to at least one other oligonucleotide in the plurality. For example, and without limitation, in some embodiments the shell of oligonucleotides comprises a plurality of immu-nostimulatory oligonucleotides, wherein one immunostimu-latory oligonucleotide has a sequence that is different than at least one other immunostimulatory oligonucleotide in the plurality. In various embodiments, the nanoparticle core comprises one or more oligonucleotides encapsulated therein.

In some embodiments, an oligonucleotide in the shell of oligonucleotides is a targeting oligonucleotide, such as an aptamer. Accordingly, all features and aspects of oligonucle-otides described herein (e.g., length, type (DNA, RNA, modified forms thereof), optional presence of spacer) also apply to aptamers. Aptamers are oligonucleotide sequences that can be evolved to bind to various target analytes of interest. Aptamers may be single stranded, double stranded, or partially double stranded.

Spacers. In some aspects and embodiments, one or more oligonucleotides in the shell of oligonucleotides that is attached to the nanoparticle core of a SNA comprise a spacer. "Spacer" as used herein means a moiety that serves to increase distance between the nanoparticle core and the oligonucleotide, or to increase distance between individual oligonucleotides when attached to the nanoparticle core in multiple copies, or to improve the synthesis of the SNA.

Thus, spacers are contemplated being located between an oligonucleotide and the nanoparticle core.

In some aspects, the spacer when present is an organic moiety. In some aspects, the spacer is a polymer, including but not limited to a water-soluble polymer, a nucleic acid, a polypeptide, an oligosaccharide, a carbohydrate, a lipid, an ethylglycol, or a combination thereof. In any of the aspects or embodiments of the disclosure, the spacer is an oligo (ethylene glycol)-based spacer. In various embodiments, an oligonucleotide comprises 1, 2, 3, 4, 5, or more spacer (e.g., Spacer-18 (hexaethyleneglycol)) moieties. In further embodiments, the spacer is an alkane-based spacer (e.g., C12). In some embodiments, the spacer is an oligonucleotide spacer (e.g., T5). An oligonucleotide spacer may have any sequence that does not interfere with the ability of the oligonucleotides to become bound to the nanoparticle core or to a target. In certain aspects, the bases of the oligonucleotide spacer are all adenylic acids, all thymidylic acids, all cytidylic acids, all guanylic acids, all uridylic acids, or all some other modified base.

In various embodiments, the length of the spacer is or is equivalent to at least about 2 nucleotides, at least about 3 nucleotides, at least about 4 nucleotides, at least about 5 nucleotides, 5-10 nucleotides, 10 nucleotides, 10-30 nucleotides, or even greater than 30 nucleotides.

SNA surface density. Generally, a surface density of oligonucleotides that is at least about 0.5 pmol/cm$^2$ will be adequate to provide a stable SNA (e.g., LSNA or LNP-SNA). In further embodiments, a surface density of oligonucleotides that is at least about 1 pmol/cm$^2$, 1.5 pmol/cm$^2$, or 2 pmoles/cm$^2$ will be adequate to provide a stable SNA (e.g., LSNA or LNP-SNA). In some aspects, the surface density of a SNA of the disclosure is at least 15 pmoles/cm$^2$. Methods are also provided wherein the oligonucleotide is attached to the nanoparticle core of the SNA at a surface density of about 0.5 pmol/cm$^2$ to about 1000 pmol/cm$^2$, or about 2 pmol/cm$^2$ to about 200 pmol/cm$^2$, or about 10 pmol/cm$^2$ to about 100 pmol/cm$^2$. In some embodiments, the surface density is about 1.7 pmol/cm$^2$. In some embodiments, the surface density is about 2 pmol/cm$^2$. In further embodiments, the surface density is at least about 0.5 pmol/cm$^2$, at least about 0.6 pmol/cm$^2$, at least about 0.7 pmol/cm$^2$, at least about 0.8 pmol/cm$^2$, at least about 0.9 pmol/cm$^2$, at least about 1 pmol/mcg, at least about 1.5 pmol/cm$^2$, at least about 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

In further embodiments, the surface density is less than about 2 pmol/cm$^2$, less than about 3 pmol/cm$^2$, less than about 4 pmol/cm$^2$, less than about 5 pmol/cm$^2$, less than about 6 pmol/cm$^2$, less than about 7 pmol/cm$^2$, less than about 8 pmol/cm$^2$, less than about 9 pmol/cm$^2$, less than about 10 pmol/cm$^2$, less than about 15 pmol/cm$^2$, less than about 19 pmol/cm$^2$, less than about 20 pmol/cm$^2$, less than about 25 pmol/cm$^2$, less than about 30 pmol/cm$^2$, less than about 35 pmol/cm$^2$, less than about 40 pmol/cm$^2$, less than about 45 pmol/cm$^2$, less than about 50 pmol/cm$^2$, less than about 55 pmol/cm$^2$, less than about 60 pmol/cm$^2$, less than about 65 pmol/cm$^2$, less than about 70 pmol/cm$^2$, less than about 75 pmol/cm$^2$, less than about t 80 pmol/cm$^2$, less than about 85 pmol/cm$^2$, less than about 90 pmol/cm$^2$, less than about 95 pmol/cm$^2$, less than about 100 pmol/cm$^2$, less than about 125 pmol/cm$^2$, less than about 150 pmol/cm$^2$, less than about 175 pmol/cm$^2$, less than about 200 pmol/cm$^2$, less than about 250 pmol/cm$^2$, less than about 300 pmol/cm$^2$, less than about 350 pmol/cm$^2$, less than about 400 pmol/cm$^2$, less than about 450 pmol/cm$^2$, less than about 500 pmol/cm$^2$, less than about 550 pmol/cm$^2$, less than about 600 pmol/cm$^2$, less than about 650 pmol/cm$^2$, less than about 700 pmol/cm$^2$, less than about 750 pmol/cm$^2$, less than about 800 pmol/cm$^2$, less than about 850 pmol/cm$^2$, less than about 900 pmol/cm$^2$, less than about 950 pmol/cm$^2$, or less than about 1000 pmol/cm$^2$.

Alternatively, the density of oligonucleotide attached to the SNA is measured by the number of oligonucleotides attached to the SNA. With respect to the surface density of oligonucleotides attached to a SNA of the disclosure, it is contemplated that a SNA as described herein comprises or consists of about 1 to about 2,500, or about 1 to about 500 oligonucleotides on its surface. In various embodiments, a SNA comprises about 10 to about 500, or about 10 to about 300, or about 10 to about 200, or about 10 to about 190, or about 10 to about 180, or about 10 to about 170, or about 10 to about 160, or about 10 to about 150, or about 10 to about 140, or about 10 to about 130, or about 10 to about 120, or about 10 to about 110, or about 10 to about 100, or 10 to about 90, or about 10 to about 80, or about 10 to about 70, or about 10 to about 60, or about 10 to about 50, or about 10 to about 40, or about 10 to about 30, or about 10 to about 20, or about 75 to about 200, or about 75 to about 150, or about 100 to about 200, or about 150 to about 200 oligonucleotides in the shell of oligonucleotides attached to the nanoparticle core. In some embodiments, a SNA comprises about 80 to about 140 oligonucleotides in the shell of oligonucleotides attached to the nanoparticle core. In further embodiments, a SNA comprises at least about 5, 10, 20, 30, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 oligonucleotides in the shell of oligonucleotides attached to the nanoparticle core. In further embodiments, a SNA consists of 5, 10, 20, 30, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 oligonucleotides in the shell of oligonucleotides attached to the nanoparticle core. In still further embodiments, the shell of oligonucleotides attached to the nanoparticle core of the SNA comprises 2, 3, 4, 5, 6, 7, 8, 9, 10, 11, 12, 13, 14, 15, 16, 17, 18, 19, 20, 50, 60, 70, 75, 80, 90, 100, 150, 160, 170, 175, 180, 190, 200, or more oligonucleotides. In some embodiments, the shell of oligonucleotides attached to the nanoparticle core of the SNA consists of 2, 3, 4, 5, 6, 7, 8, 9, 10, 11, 12, 13, 14, 15, 16, 17, 18, 19, 20, 30, 40, 50, 60, 70, 75, 80, 90, 100, 150, 160, 170, 175, 180, 190, or 200 oligonucleotides.

Uses of SNAs in Immune Regulation

Toll-like receptors (TLRs) are a class of proteins, expressed in sentinel cells, that play a key role in regulation of innate immune system. The mammalian immune system uses two general strategies to combat infectious diseases. Pathogen exposure rapidly triggers an innate immune response that is characterized by the production of immunostimulatory cytokines, chemokines and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 8 and TLR 9 that respond to specific oligonucleotides are located inside special intracellular compartments, called endosomes. The mechanism of modulation of, for example and without limitation, TLR 8 and TLR 9 receptors, is based on DNA-protein interactions.

As described herein, synthetic immunostimulatory oligonucleotides that contain CpG motifs that are similar to those found in bacterial DNA stimulate a similar response of the TLR receptors. Thus, CpG oligonucleotides of the disclosure have the ability to function as TLR agonists. Other TLR agonists contemplated by the disclosure include, without limitation, single-stranded RNA and small molecules (e.g., R848 (Resiquimod)). Therefore, immunomodulatory (e.g., immunostimulatory) oligonucleotides have various potential therapeutic uses, including treatment of immune deficiency and cancer.

Accordingly, in some embodiments, methods of utilizing SNAs as described herein for modulating toll-like receptors are disclosed. The method up-regulates the Toll-like-receptor activity through the use of a TLR agonist. The method comprises contacting a cell having a toll-like receptor with a SNA of the disclosure, thereby modulating the activity and/or the expression of the toll-like receptor. The toll-like receptors modulated include one or more of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and/or toll-like receptor 13.

Methods of Inducing an Immune Response

The disclosure also includes methods for eliciting an immune response in a subject in need thereof, comprising administering to the subject an effective amount of a SNA (e.g., formulated as an antigenic composition) of the disclosure. As exemplified herein, antiviral SNAs of the disclosure activate human peripheral blood mononuclear cells and generate specific neutralizing antibodies against a pseudovirus. In various embodiments, administering SNAs of the disclosure (e.g., formulated as a composition, pharmaceutical formulation, or antigenic composition) to a subject results in an increase in the amount of neutralizing antibodies against the viral antigen that is produced in the subject relative to the amount of neutralizing antibodies against the viral antigen that is produced in a subject who was not administered the SNAs. In further embodiments, the increase is a 2-fold increase, a 5-fold increase, a 10-fold increase, a 50-fold increase, a 100-fold increase, a 200-fold increase, a 500-fold increase, a 700-fold increase, or a 1000-fold increase.

In further embodiments, antiviral SNAs of the disclosure activate human peripheral blood mononuclear cells and generate an antibody response against a virus. In some embodiments, the antibody response is a total antigen-specific antibody response. In further embodiments, administering SNAs of the disclosure (e.g., formulated as a composition, pharmaceutical formulation, or antigenic composition) to a subject results in an increase in the amount of total antigen-specific antibodies against the viral antigen that is produced in the subject relative to the amount of total antigen-specific antibodies against the viral antigen that is produced in a subject who was not administered the SNAs. In further embodiments, the increase is a 2-fold increase, a 5-fold increase, a 10-fold increase, a 50-fold increase, a 100-fold increase, a 200-fold increase, a 500-fold increase, a 700-fold increase, or a 1000-fold increase. A "total antigen-specific antibody response" is a measure of all of the antibodies (including neutralizing and non-neutralizing antibodies) that bind to a particular antigen.

The immune response raised by the methods of the present disclosure generally includes an antibody response, preferably a neutralizing antibody response, maturation and memory of T and B cells, antibody dependent cell-mediated cytotoxicity (ADCC), antibody cell-mediated phagocytosis (ADCP), complement dependent cytotoxicity (CDC), and T cell-mediated response such as CD4+, CD8+. The immune response generated by the SNA comprising a viral antigen as disclosed herein generates an immune response that recognizes, and preferably ameliorates and/or neutralizes, a viral infection as described herein. Methods for assessing antibody responses after administration of an antigenic composition (immunization or vaccination) are known in the art and/or described herein. In some embodiments, the immune response comprises a T cell-mediated response (e.g., peptide-specific response such as a proliferative response or a cytokine response). In preferred embodiments, the immune response comprises both a B cell and a T cell response. Antigenic compositions can be administered in a number of suitable ways, such as intramuscular injection, subcutaneous injection, intradermal administration and mucosal administration such as oral or intranasal. Additional modes of administration include but are not limited to intravenous, intraperitoneal, intranasal administration, intra-vaginal, intra-rectal, and oral administration. A combination of different routes of administration in the immunized subject, for example intramuscular and intranasal administration at the same time, is also contemplated by the disclosure.

Antigenic compositions may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >55 years old, >60 years old, preferably >65 years old), and the young (e.g., <6 years old, 1-5 years old, preferably less than 1 year old). Additional subjects for receiving the vaccines, SNAs, or compositions of the disclosure include naïve (versus previously infected) subjects, currently infected subjects, or immunocompromised subjects.

Administration can involve a single dose or a multiple dose schedule. In any of the aspects or embodiments, of the disclosure, administration comprises or consists of two doses. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, or a subcutaneous prime and a subcutaneous boost. Administration of more than one dose (typically two doses) is particularly useful in immunologically naive subjects or subjects of a hyporesponsive population (e.g., diabetics, or subjects with chronic kidney disease (e.g., dialysis patients)). In various embodiments, the second dose is administered about or at least about 2 weeks after the first dose. Multiple doses will typically be administered at least 1 week apart (e.g., about 2 weeks, about 3 weeks, about 4 weeks, about 6 weeks, about 8 weeks, about 10 weeks, about 12 weeks, or about 16 weeks). In some embodiments, multiple doses are administered from one, two, three, four or five months apart. Antigenic compositions of the present disclosure may be administered to patients at substantially the same time as (e.g., during the same medical consultation or visit to a healthcare professional) other vaccines.

In general, the amount of SNA comprising a viral antigen in each dose of the antigenic composition is selected as an amount effective to induce an immune response in the subject, without causing significant, adverse side effects in the subject.

Uses of SNAs in Gene Regulation

In some aspects of the disclosure, an oligonucleotide associated with a SNA of the disclosure (e.g., LNP-SNA, LSNA) inhibits the expression of a gene. Thus, in some embodiments, a SNA performs both an antiviral function and a gene inhibitory function. In such aspects, the shell of oligonucleotides that is attached to the external surface of the nanoparticle core comprises one or more immunostimulatory oligonucleotides and one or more inhibitory oligonucleotides designed to inhibit target gene expression.

Methods for inhibiting gene product expression provided herein include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a SNA. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of SNA and a specific oligonucleotide.

In various aspects, the methods include use of an oligonucleotide which is 100% complementary to the target polynucleotide, i.e., a perfect match, while in other aspects, the oligonucleotide is at least (meaning greater than or equal to) about 95% complementary to the polynucleotide over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the oligonucleotide to the extent that the oligonucleotide is able to achieve the desired degree of inhibition of a target gene product.

The percent complementarity is determined over the length of the oligonucleotide. For example, given an antisense compound in which 18 of 20 nucleotides of the inhibitory oligonucleotide are complementary to a 20 nucleotide region in a target polynucleotide of 100 nucleotides total length, the oligonucleotide would be 90 percent complementary. In this example, the remaining noncomplementary nucleotides may be clustered or interspersed with complementary nucleobases and need not be contiguous to each other or to complementary nucleotides. Percent complementarity of an inhibitory oligonucleotide with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

The oligonucleotide utilized in such methods is either RNA or DNA. The RNA can be an inhibitory oligonucleotide, such as an inhibitory RNA (RNAi) that performs a regulatory function, and in various embodiments is selected from the group consisting of a small inhibitory RNA (siRNA), a single-stranded RNA (ssRNA), and a ribozyme. Alternatively, the RNA is microRNA that performs a regulatory function. The DNA is, in some embodiments, an antisense-DNA. In some embodiments, the RNA is a piwi-interacting RNA (piRNA).

EXAMPLES

Example 1

This example describes results of in vitro and in vivo experiments testing two different SNA structures—protein-core SNAs (ProSNAs) and liposomal core SNAs—and their ability to function as vaccines. The shell of oligonucleotides of both the ProSNAs and the liposomal core SNAs was made up of CpG adjuvant DNA. RBD protein or 51 protein was encapsulated in the liposomal core SNAs, while RBD was used as the core of the ProSNAs.

Briefly, and by way of example, the antiviral SNA vaccines are synthesized as follows. For the liposome-core SNAs, lipid films consisting of an amphiphilic molecule, for example and without limitation DOPC (1,2-dioleoyl-sn-glycero-3-phosphocholine), DPPC (dipalmitoyl phosphatidylcholine), and/or monophosphoryl lipid A-4 (MPLA-4), are hydrated with phosphate buffered saline (PBS) containing dissolved viral antigens (in either peptide or protein form). These materials are then extruded to form small unilamellar vesicles (SUVs, also called liposomes) less than or equal to 80 nm in diameter, purified using tangential flow filtration (TFF) or dialysis, and characterized using dynamic light scattering (DLS), a bicinchoninic acid (BCA) or pierce assay (for protein or peptide quantification, respectively), and a phosphatidylcholine (PC) assay (for lipid quantification). Cholesterol-terminated DNA adjuvant is then mixed in a 75:1 molar ratio with liposomes to form SNAs. For protein-core SNAs, the surface lysine or cysteine residues of immunogenic proteins or protein domains are modified with a crosslinking molecule. The crosslinker is then conjugated to a functionalized DNA adjuvant. The resulting SNAs are purified using a combination of nickel affinity, anion exchange, and size exclusion chromatography. As shown below, the antiviral SNAs activated human peripheral blood mononuclear cells (PBMCs) and produced virus-specific antibodies.

Methods

Synthesis of Receptor Binding Domain Protein Spherical Nucleic Acids (RBD-ProSNA)

Reaction of Surface-Accessible Lysines with N-hydroxysuccinimide-PEG4-Azide (NHS-PEG4-azide) or (4-nitrophenyl 2-(2-pyridyldithio)ethyl carbonate (NDEC) Crosslinker. 500 equivalents of crosslinker (NHS-PEG4-azide or NDEC) were added to the Spike Receptor Binding Domain (RBD) protein in 1×PBS. The reaction was shaken (900 rpm) for two hours at 25° C. Unconjugated linker was removed by size exclusion chromatography. The number of modifications was assessed by MALDI-MS using sinapinic acid as a matrix.

Functionalization with DBCO-dT or Thiol Terminated CPG1826 Oligonucleotides. 500 equivalents of CPG1826 DNA (SEQ ID NO: 9) strands were first lyophilized overnight. Then linker modified RBD in 1×PBS was added to rehydrate the DNA. For Spike proteins modified with NHS-PEG4-azide, DBCO-dt terminated CPG1826 strands were reacted. For Spike proteins modified with NDEC, thiol terminated CPG1826 strands were reacted. The reaction was shaken (900 rpm) for 48 hours at 25° C. Unreacted DNA strands were removed by size exclusion chromatography. The number of DNA strands per protein was calculated based on a combination of UV-Vis spectroscopy and BCA assay.

Synthesis of Spike Protein Spherical Nucleic Acids (Spike-ProSNA)

Reaction of Surface-Accessible Lysines with N-hydroxysuccinimide-PEG4-Azide (NHS-PEG4-azide) or (4-nitrophenyl 2-(2-pyridyldithio)ethyl carbonate (NDEC) Crosslinker. 500 equivalents of crosslinker (NHS-PEG4-azide or NDEC) were added to the Spike protein in 1× PBS. The reaction was shaken (900 rpm) for two hours at 25° C. Unconjugated linker was removed by 10 rounds of centrifugation using a 100 kDa Amicon MWCO filter. The number of modifications was assessed by MALDI-MS using sinapinic acid as a matrix.

Functionalization with DBCO-dT or Thiol Terminated CPG1826 Oligonucleotides. 500 equivalents of CPG1826 DNA strands (SEQ ID NO: 9) were first lyophilized overnight. Then linker modified Spike protein in 1×PBS was added to rehydrate the DNA. For Spike proteins modified with NHS-PEG4-azide, DBCO-dt terminated CPG1826 strands were reacted. For Spike proteins modified with NDEC, thiol terminated CPG1826 strands were reacted. The reaction was shaken (900 rpm) for 48 hours at 25° C. Unreacted DNA strands were removed by successive rounds of centrifugation in a 100 kDa Amicon MWCO filter until the filtrate did not have a detectable absorbance at 260 nm. Typically, complete removal of DNA required 30-40 washing steps. The number of DNA strands per protein was calculated based on a combination of UV-Vis spectroscopy and BCA assay.

Synthesis of RBD Encapsulated Liposomal Spherical Nucleic Acids (RBD@Lipo SNA)

1 mL of a 7.16 mg/mL solution of RBD protein in PBS was added to a 50 mg film of DOPC liposomes. An additional 1.5 mL of PBS was added to the film and liposomes were subjected to approximately 20 freeze-thaw cycles, using liquid nitrogen and sonication in a 37° C. water bath, before being extruded to 80 nanometers (nm). The extruded liposomes were purified using tangential flow filtration with a pore size of 500 kDa (Spectrum) to remove any non-encapsulated protein. The liposomes were washed through at least three times with PBS. The amount of protein encapsulated within the liposomes was measured using a BCA assay after disruption of the liposome with 1% SDS. The liposome concentration was measured using a commercially available phosphatidyl choline (PC) assay. From these assays, the loading of protein per liposome was calculated. To form SNAs, 3' cholesterol-terminated CPG1826 DNA strands were added to the liposomes in a 75:1 concentration ratio (oligonucleotides:liposome) and incubated at 37° C. overnight before storage at 4° C.

Figure 1:
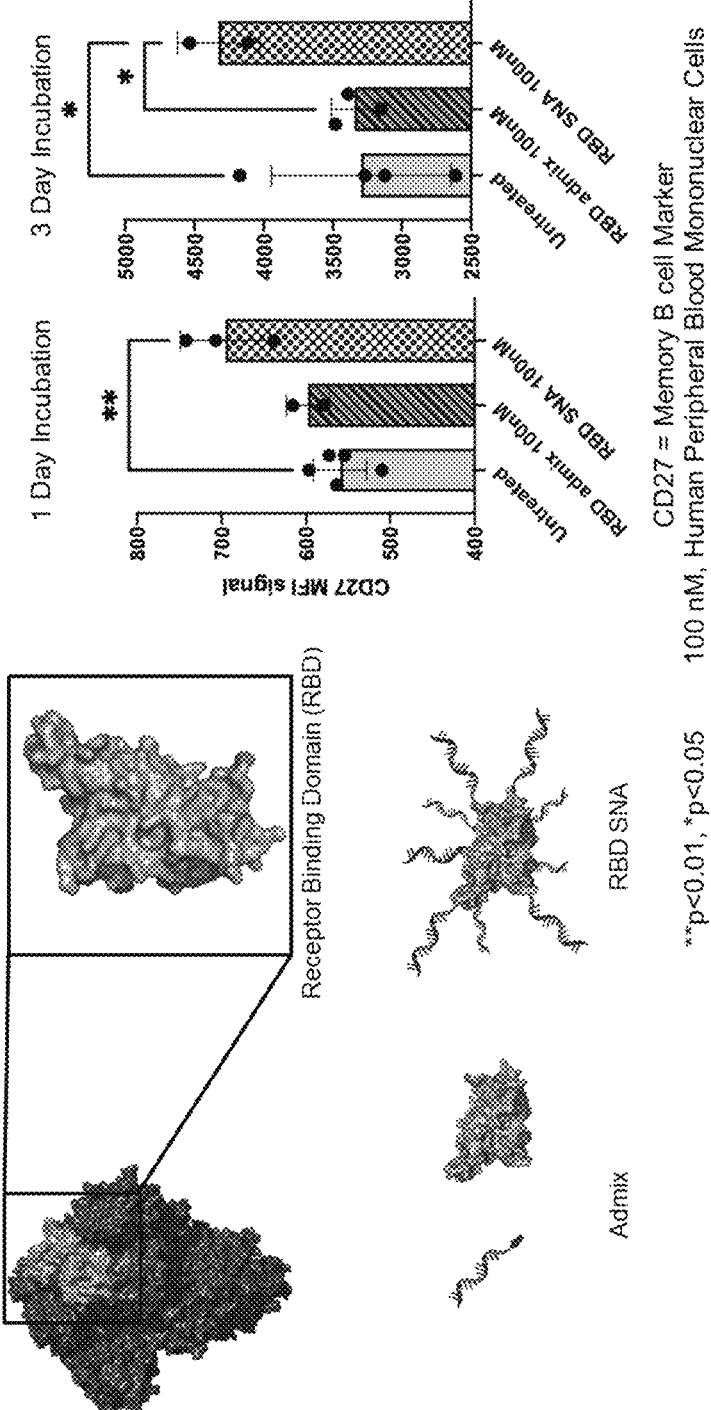
FIG. 1 shows that a protein-core SNA (ProSNA) vaccine was able to target Sars-CoV2-Spike protein and activate B cells in vitro.
Figure 2:
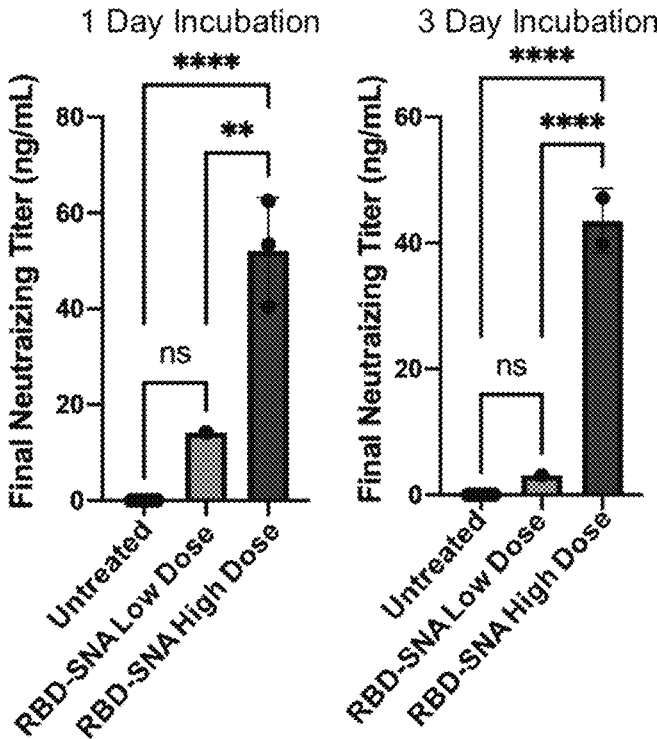
FIG. 2 shows that the high dose of the ProSNA was capable at both timepoints of raising neutralizing titers significantly different from an untreated hPBMC control.
Figure 3:
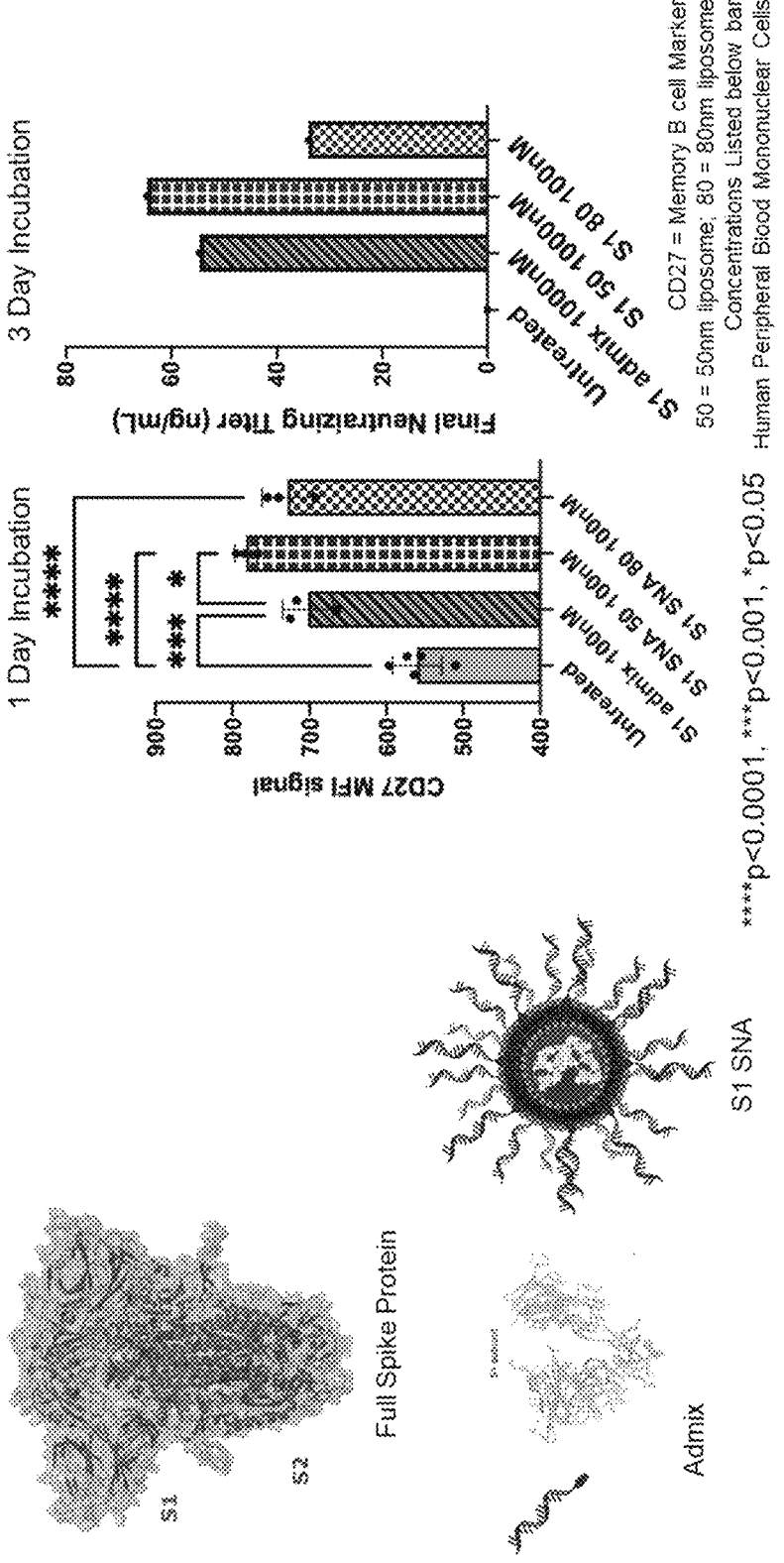
FIG. 3 shows that the liposomal SNA vaccine encapsulating S1 subunit activated B cells and Induced antibody production.

In Vitro Human Peripheral Blood Mononuclear Cell Activation with COVID-Specific SNAs Human peripheral blood mononuclear cells (hPBMCs) were purchased from Zenbio and thawed at the start of experiment. The cell suspension was added to 3 mL of RPMI media supplemented with 10% heat inactivated fetal bovine serum and 1% Penicillin-Streptomycin (RPMI+/+) and spun at 300×g for 10 minutes. Cells were counted and diluted to $2 \times 10^6$ cells/mL. 100 uL of this cell solution was added to each well of a 96 round bottom plate. Samples were diluted to 2× the desired concentration in RPMI+/+ media and 100 uL were added 1:1 to each well so that the final concentration is what is specified in FIGS. 1-3. After the desired time point (24 or 72 hours) the plate was spun at 1200 rpm for 5 minutes and approximately 180 uL of supernatant was collected and transferred to a 96 well plate for use in the Neutralizing Antibody Binding Assay, described below. 200 uL of PBS was added to the cells and they were transferred to microtiter flow tubes. Samples were washed with 600 uL PBS, spun at 1200 rpm for 5 min, aspirated, and stained with antibodies (Live marker, FITC; CD19, BUV661; HLA-DR, BB700; CD27, BV605) for 15 minutes at 4° C. Samples were washed with 600 uL of PBS, spun at 1200 rpm for 5 minutes, aspirated, and resuspended in 100 uL of fixation buffer.

In Vivo Activation with COVID-Specific SNAs

Mice were injected subcutaneously either once or twice (two weeks apart), and were harvested two weeks after the final injection. Each injection dose was either 6 nmol (for RBD ProSNA and corresponding RBD Admix) or 1.4 nmol (for RBD@Lipo SNA and the corresponding RBD Admix).

Retro-Orbital Blood Draw

Animals were anesthetized with isoflurane and once asleep a heparin lined pipette was inserted through the conjunctiva and into the orbital sinus by quickly rotating the tube. Approximately 100 uL of blood was drawn and stored at room temperature for at least 30 minutes to allow the blood to clot. The blood was then centrifuged at 1000×g for 10 minutes and the supernatant (serum) is carefully removed and transferred to a 96 well plate for use and future storage.

ELISA for RBD-Specific IgG Antibodies

A Biolegend Nunc™ MaxiSorp™ ELISA Uncoated Plate was coated. For this, 2.5 μg/mL of RBD protein was diluted in 1× Biolegend ELISA Coating Buffer (sold as 5×, diluted with sterile DiH20). 100 uL of this solution was put in each well on the plate to coat and the plate was placed for 2 hours at 37° C. After the 2 hours, the plate was washed once with 200 uL of 10% fetal bovine serum in PBS containing 0.1% Tween-20 (sterile filtered, referred to as PBS-T+10FBS). 200 uL of this sample solution were added to block for 2 hours at 37° C. Mouse sera were diluted to various dilutions in 5× ELISA dilution buffer (eBioscience Cat #: 00-4202-56) (dilutions included 50×, 100×, 500×, 1000×, 2500×, and/or 5000×). After the blocking step, the blocking solution was removed and 100 uL of diluted samples were added to each well. The plate was incubated for 1 hours at 37° C. After this hour, the plate was washed three times with PBS-T, and a secondary antibody (here, Goat anti-mouse IgG-HRP) was diluted 1:4000 in 5× ELISA dilution buffer, and 100 uL of this secondary antibody solution was added to each well. This was left for 1 hour at room temp. The plate was washed three times with PBS-T. 6 ml of TMB Reagent A was mixed with 6 ml TMB Reagent B (BioLegend TMB Substrate Reagent Set, Cat. No. 421101) immediately prior to addition, and 1004 was added to each well. The plate was left to incubate at room temperature for 3 minutes. To stop the color reaction, 100 μl of TMB Stop Solution was added, and absorbance at 450 nm was immediately read. Titers were defined as the reciprocal serum dilution at which the absorbance at 450 nm exceeded background by greater than 0.5 absorbance units.

Neutralizing Antibody Binding Assay (Genscript: Cat #: L00847)

Kit instructions were followed. Briefly, untreated supernatant (for in vitro samples) or Naïve sera (for in vivo samples) was diluted 1:10 with provided sample dilution buffer to make 1.35 mL of Negative matrix control Wash solution was diluted to 1× from 20× stock in sterile diH$_2$O. The provided standard monoclonal antibody (A02051) was diluted to a final working concentration of 300 ng/mL through a series of dilutions. From this, a standard curve was created. Samples (supernatant for in vitro, sera for in vivo) were diluted 1:10 in sample dilution buffer to get 105 uL total and from this solution, 1:3 serial dilutions were made down to 1:270. Positive and Negative controls provided by the kit were diluted 1:10 as per the protocol. A solution of HRP functionalized RBD (RBD-HRP) was made by diluting the provided protein 1:1000 with provided RBD Dilution buffer. 60 uL of samples and 120 uL of the standard curve were each added 1:1 with the mixed RBD-HRP solution and allowed to incubate at 37° C. for 30 minutes. 100 uL of these solutions were then added to the provided ELISA plate pre-coated with hACE2 and incubated at 37° C. for 15 minutes. The plates were washed 4 times with the diluted 1× wash solution before adding 100 uL of provided TMB solution to each well and allowing that to incubate at room temp in the dark for 15 minutes. 50 uL of Stop Solution was added to stop the reaction and absorbance at 450 nm was immediately read. The percentage of inhibition was calculated as %=(1–OD$_{450}$ post immune sera/OD$_{450}$ negative control)×100%

Results

In Vitro Studies Using Protein-Core SNAs (ProSNAs) and Liposomal SNAs

A protein-core SNA (ProSNA) composed of the Receptor binding domain as the core and CpG 7909 adjuvant DNA (SEQ ID NO: 7) as the shell were tested in vitro in human peripheral blood mononuclear cells (hPBMCs). After 1 and 3 days of incubation with hPBMCs at 100 nM concentration of either a simple mixture of RBD and CpG 7909 DNA (admix) or the ProSNA (RBD SNA), cells were collected and stained for CD27, a marker of B cell memory, which was quantified through median fluorescence intensity (MFI) by flow cytometry. RBD is the portion of the protein responsible for interacting with the ACE2 receptors on the lungs—it is therefore on the most exposed region of the spike protein. The CD27 costimulatory marker plays keys role in regulating B-cell activation and antibody synthesis—if B cells are activated then one should see an increase in CD27, which is also indirectly indicative of antibody production. The SNA significantly enhanced B cell memory marker expression after both 1 and 3 days of incubation. See FIG. 1. This experiment showed that the ProSNA vaccine was able to target Sars-CoV2-Spike protein and activate B cells.

Next, ProSNA composed of the receptor binding domain as the core and CpG 7909 adjuvant DNA as the shell were tested in vitro in human peripheral blood mononuclear cells (hPBMCs) at two doses (low, 500 nM and high, 2000 nM). Supernatant from the well was collected after 1 and 3 days and assessed in the Neutralizing Antibody Binding Assay with a standard curve to produce a final neutralizing titer. See FIG. 2, which showed that the high dose of the SNA was capable at both timepoints of raising neutralizing titers significantly different from an untreated hPBMC control.

Liposomal SNAs encapsulating the 51 subunit of the Spike protein in the core with CpG 7909 adjuvant DNA as the shell were tested in vitro in human peripheral blood mononuclear cells (hPBMCs). Two different size particles of the liposome core were assessed (50 nm and 80 nm) and they were compared to a simple mixture of 51 subunit and CpG 7909 DNA (admix). After 1 day of incubation with hPBMCs at 100 nM concentration, cells were collected and stained for CD27, a marker of B cell memory, which was quantified through median fluorescence intensity (MFI) by flow cytometry. The liposomal SNA significantly enhanced B cell memory marker expression after 1 day of incubation. This correlated to higher neutralizing antibody production, detected from the supernatant after 3 days of incubation and assessed in a pseudovirus inhibition study with to a standard curve. See FIG. 3.

In Vivo Studies Using Protein-Core SNAs (ProSNAs) and Liposomal SNAs

Mice were injected every two weeks for doses and were harvested two weeks after the final injection for both sets (FIG. 4). Blood was collected through retro orbital draw. Groups considered in each experiment are shown in FIG. 4. RBD ProSNA is the SNA with RBD as the protein core and RBD@Lipo SNA is a liposomal SNA with RBD protein encapsulated within it. Admixes were created to compare against each SNA condition as well as match the exact ratio of adjuvant to antigen in the corresponding SNA group.

Figure 5:
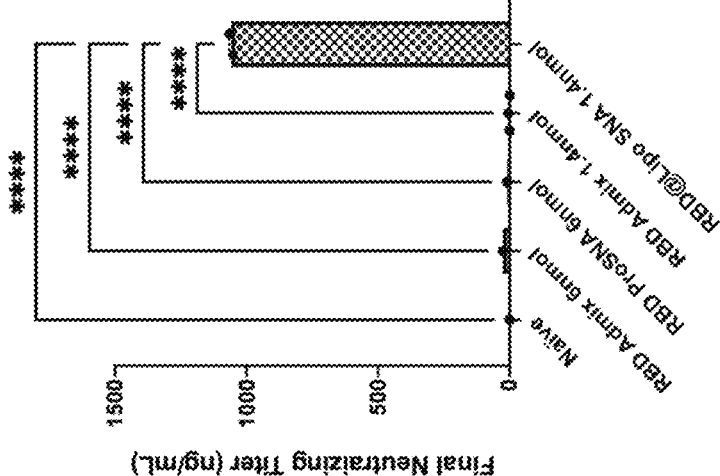
FIG. 5 shows that one dose of the liposomal SNA vaccine produced robust antibodies in sera.
Figure 5:
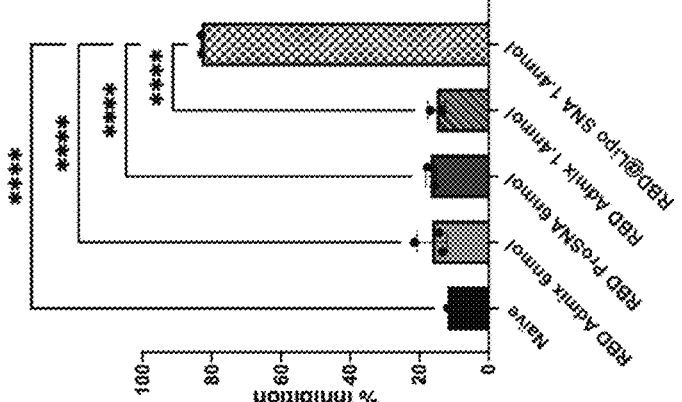
Figure 5:
Figure 5:
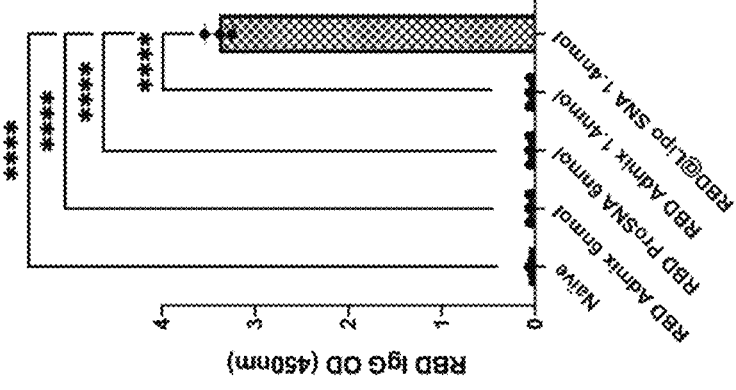

After collection of sera from blood following after one dose of each condition, samples were quantified via ELISA for the presence of any RBD-specific IgG antibodies. The absorbance at 450 nm (shown as optical density, OD) is shown for samples after the colorimetric detection of TMB substrate. At a 1:500 dilution of sera, the RBD@Lipo SNA (liposomal SNA with encapsulated RBD protein) was producing the highest amount of any RBD-specific IgG antibodies. See FIG. 5, left panel. Sera were then employed in the Neutralizing Antibody Binding Assay with a standard curve. See FIG. 5, middle panel. The percent of inhibition (30% cutoff value for positive inhibition effect according to Manufacturer's protocol) is shown for the 4 different treatments at a 1:10 dilution and is compared to Naïve mice which received no vaccination. The RBD@Lipo SNA is the only group that showed a significant ability to inhibit pseudoviral binding to the ACE2 receptor. See FIG. 5, right panel. This can be compared to a standard curve to obtain a final neutralizing titer, which showed similarly that only the RBD@Lipo SNA group effectively produced neutralizing antibodies in sera of mice after one injection.

Figure 6:
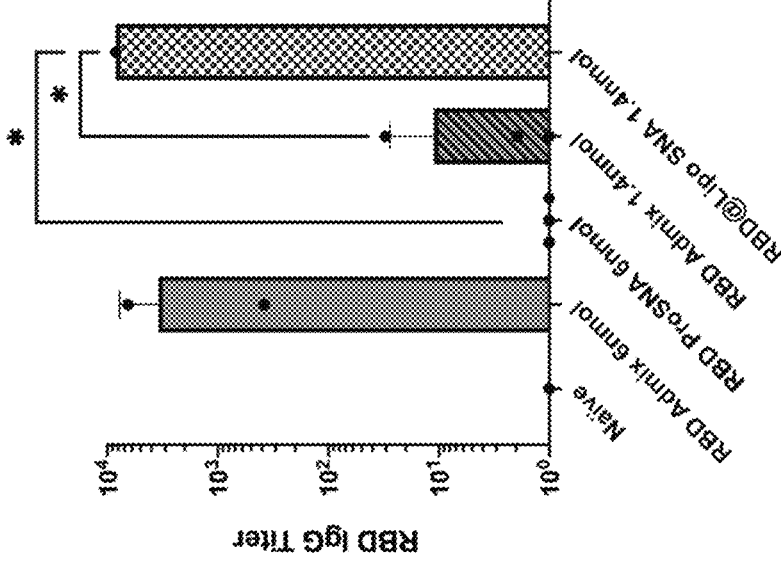
FIG. 6 shows that two doses of the liposomal SNA vaccine enhanced the total amount of RBD-specific antibodies.
Figure 6:
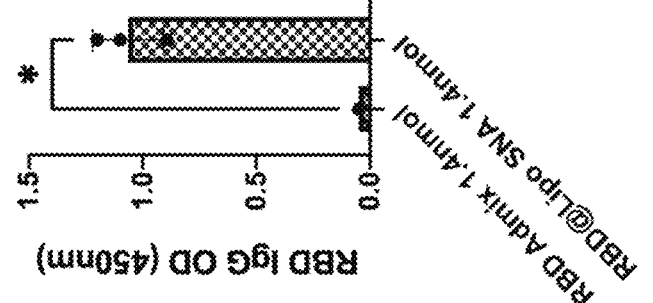
Figure 6:
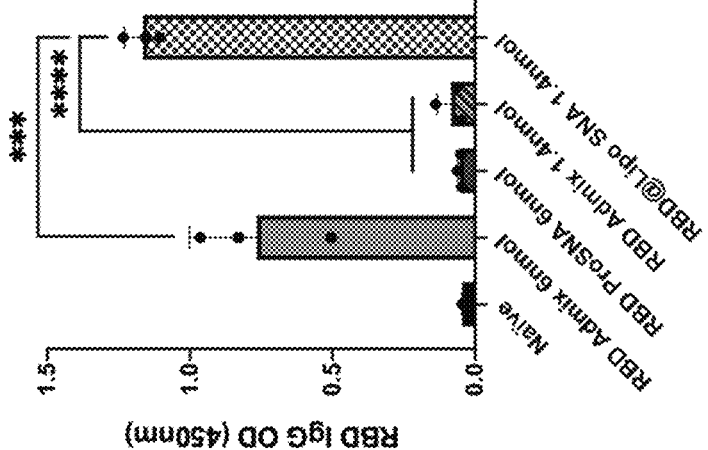

After collection of sera from blood after two doses of each condition, samples were quantified via ELISA for the presence of any RBD-specific IgG antibodies. See FIG. 6, left panel. The absorbance at 450 nm (shown as optical density, OD) is shown for samples after the colorimetric detection of TMB substrate. At a 1:1000 dilution of sera, the RBD@Lipo SNA (liposomal SNA with encapsulated RBD protein) was producing the highest amount of any RBD-specific IgG antibodies. There was some antibody production occurring for mice vaccinated with 6 nmol of RBD Admix, but the production was not as high as approximately one-quarter of the dose delivered via SNA formulation. See FIG. 6, middle panel. A 1:5000 dilution is shown for the RBD@Lipo SNA and corresponding 1.4 nmol admix. See FIG. 6, right panel. A series of dilutions were employed to plot the decrease of OD upon increasing dilution. These values were plotted on a dilution vs OD curve and a curve (Sigmoidal, 4PL, X is concentration) was fit to the graph using GraphPad Prism software. Titers were defined as the reciprocal serum dilution at which the absorbance at 450 nm exceeded background by greater than 0.7 absorbance units, and thus values were obtained by extrapolation to the fit curves.

Figure 7:
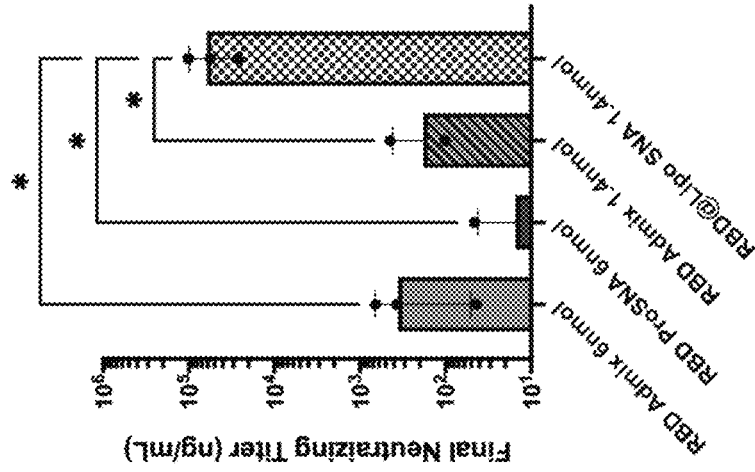
FIG. 7 shows that two doses of the liposomal SNA vaccine enhanced the amount of neutralizing antibodies.
Figure 7:
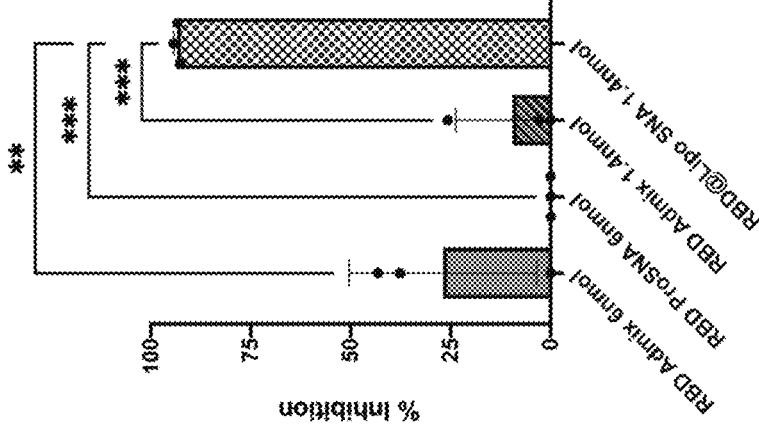
Figure 7:
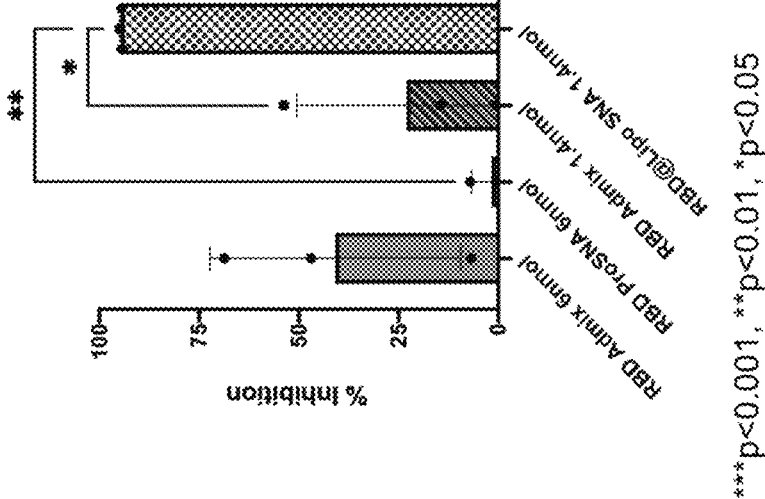

Sera were employed in the Neutralizing Antibody Binding Assay with a standard curve. See FIG. 7, left panel. The percent of inhibition (30% cutoff value for positive inhibition effect according to Manufacturer's protocol) is shown for the 4 different treatments at a 1:10 dilution. The RBD@Lipo SNA showed the most consistent and significant ability across the 3 mice to inhibit pseudoviral binding to the ACE2 receptor. See FIG. 7, middle panel. This ability was even more pronounced when the sera was diluted 1:30. In both cases, the neutralization ability held at about 93-95%. See FIG. 7, right panel. This inhibition ability was compared to a standard curve to obtain a final neutralizing titer, which showed similarly that while the admix groups were producing specific antibodies, these antibodies had approximately 2 orders of magnitude lower neutralization ability than those produced from the RBD@Lipo SNA vaccination group, which produced the most neutralizing antibodies in sera of mice after two injections.

Example 2

Despite recent efforts demonstrating that organization and presentation of vaccine components are just as important as composition in dictating vaccine efficacy, antiviral vaccines have long focused solely on the identification of the immunological target. This example describes a study aimed at exploring how vaccine component presentation in the context of spherical nucleic acids (SNAs) can be used to elicit and maximize an antiviral response. Using COVID-19 as a topical example of an infectious disease with an urgent need for rapid vaccine development, an antiviral SNA vaccine was designed, encapsulating the receptor binding domain (RBD) subunit into a liposome and decorating the core with a dense shell of CpG motif toll-like receptor 9 agonist oligonucleotides. This vaccine induced memory B cell formation in human cells and in vivo administration into mice generated robust binding and neutralizing antibody titers. Moreover, the SNA vaccine outperformed multiple simple mixtures incorporating clinically-employed adjuvants. Through modular changes to SNA structure, key relationships and proteomic insights were uncovered between adjuvant and antigen ratios, concepts potentially translatable across vaccine platforms and disease models. Importantly, when humanized ACE2 transgenic mice were challenged in vivo against a lethal live COVID virus, only mice that received the SNA vaccine had a 100% survival rate and cleared all remnants of virus from their lungs. This work underscored the potential for SNAs to be implemented as an easily adaptable and generalizable platform to fight infectious disease and demonstrated the importance of structure and presentation in the design of next generation antiviral vaccines.

Infectious diseases have long threatened humanity due to their ability to rapidly spread and mutate across populations, infecting many people (1). The rapid and global spread of SARS-CoV-2, the virus that causes COVID-19, emphatically revealed this and highlighted the importance of effective vaccination strategies to mitigate the spread and infectivity of viruses. Vaccination strategies are increasingly important as the potential for emerging infectious diseases still to come is considered (2, 3), where the ability to rapidly adapt vaccine platforms through advancement of previous knowledge can be a huge asset. In particular, protein-based subunit vaccines can reduce vaccine production costs, while diminishing vaccine side effects. However, the design of many recent vaccines has been random, with ultimate outcomes of vaccine performance difficult to correlate between candidates.(4)

An example of this is the influenza vaccine, which has relied on various simple mixtures of antigenic protein subunit target and adjuvant in solution to induce immune responses (5). As a result, influenza vaccine effectiveness has varied dramatically by year, with a low of 10% effectiveness in 2004-2005 and a high of 60% effectiveness in 2010-2011 (4, 6). This high variability is often attributed to the level of antigenic match between circulating viruses and vaccine strains. However, recent work has shown that the same antigen target can be more or less antigenic depending on the mode of presentation and delivery to the immune system (4, 7). By harnessing this concept, termed rational vaccinology, (8) efforts to correlate vaccine design with performance are greatly aided by providing structurally-informed and optimized vaccine platforms that can be readily and quickly adapted to new disease targets.

Rational vaccinology has been implemented successfully for vaccines against cancer, where nanoscale changes have dramatically altered immune activation and tumor reduction (8-10). The application of this approach toward infectious disease has yet to be fully realized, and the potential for it to dramatically impact the success of vaccine development remains untapped. As described herein, spherical nucleic acid (SNA) nanotechnology has been implemented as a tool to explore the impact of vaccine presentation when applied to infectious disease using COVID-19 as a case study. SNAs are comprised of a nanoparticle core surrounded by a dense radial arrangement of oligonucleotides (11-13). The SNA platform is modular and biocompatible, effective at entering cells rapidly and in high quantities through scavenger-receptor A mediated endocytosis, and resistant to nuclease degradation due to the dense arrangement of oligonucleotides (14, 15). Moreover, by using a DNA shell containing immunostimulatory oligonucleotides (e.g., CpG motif DNA), SNAs robustly activate the innate immune system through toll-like receptor (TLR) 9 (8, 16), and exhibit efficient lymph node drainage and high co-delivery of adjuvant and antigen to antigen-presenting cells (APCs) (8, 10). These properties have been harnessed herein to maximize humoral responses and generate antibodies effective at neutralization in pseudoviral assays, capable of withstanding mutations to still bind the target, and protective in mice against a lethal viral challenge. Overall, this example reports enhancement in immune response, leading to a 100% survival rate in a lethal viral challenge, which was achieved through utilization of the SNA's privileged architecture.

Materials and Methods

Study Design

Sample sizes in this study were empirically estimated by considering variations between animals in past work measuring immune responses with the SNA construct. It was ensured that the quantity of animals employed per group would be sufficient to provide necessary statistical power. All mice were randomly assigned to groups. Where possible, study was blinded such that sample analysis was not done by the same person who had injected the animals. The number of replicates per group is described in each figure legend.

Materials and Animals

Unless otherwise noted, all reagents were purchased commercially and used as received. Oligonucleotides were synthesized as described below. Proteins were obtained from Northwestern's Recombinant Protein Production core. Chemicals were purchased from suppliers listed in parentheses. C57BL/6 female mice, age 8-12 weeks old, and k18-hACE2 male and female mice (stock no. 034860), age 6-8 weeks old, were purchased from Jackson Laboratory. Mice were used in accordance with all national and local guidelines and regulations and protocols performed were approved by the institutional animal use committee at Northwestern University (IUCAC) and University of Chicago. Experiments with SARS-CoV-2 were performed in biosafety level 3 (BSL3) and animal BSL3 (ABSL3) containment in accordance with the institutional guidelines following experimental protocol review and approval by the Institutional Biosafety Committee (IBC) and the Institutional Animal Care and Use Committee (IACUC) at the University of Chicago.

strands were deprotected using a 1:1 solution of 37% ammonium hydroxide/40% methylamine (Sigma) at 55° C. for 35 minutes. The strands were then purified using a C4 column on reverse phase HPLC (Shimadzu), using a gradient of Buffer A (0.1M triethylammonium acetate (Sigma) and 3% acetonitrile (Sigma) in water) to pure acetonitrile over 45 minutes, and the peaks were collected as fractions. The dimethoxytrityl (DMT) group was removed from the product strands by incubation in 20% aqueous acetic acid (Sigma) at room temperature (RT) for 1 hour, followed by three washes with ethyl acetate (Sigma) to remove DMT. The final product was lyophilized and resuspended in deionized water ($diH_2O$). The concentration was measured using UV-vis absorption at 260 nm with extinction coefficients calculated through the IDT OligoAnalyzer online tool (listed in Table 2). The molecular weight of the sequences was measured by matrix-assisted laser desorption time of flight (MALDI-TOF) with a Bruker Rapiflex and compared to calculated molecular weight estimates via the IDT Oligo-Analyzer Tool.

TABLE 2

| | | | | |
|---|---|---|---|---|
| DNA Adjuvant Sequences used in this Example. | | | | |
| Name | Sequence (5' to 3')[3] | Backbone (PS = phosphorothioate) | Calc'd Mass g/mol | Extinction Coefficient L/(mole · cm)[1] |
| CpG 1826 | TCC ATG ACG TTC CTG ACG TT (Spacer18)₂ Cholesterol (SEQ ID NO: 11) | PS | 6364.1 | 181100 |
| CpG 1826 Cy5 Fluorophore-labeled[2] | TCC ATG ACG TTC CTG ACG TT Cy5 (Spacer18)₂ Cholesterol (SEQ ID NO: 12) | PS | 8405.6 | 191100 |
| CpG 7909 | TCG TCG TTT TGT CGT TTT GTC GTT (Spacer18)₂ Cholesterol (SEQ ID NO: 13) | PS | 7698.2 | 209400 |

[1]Calculated using IDT's OligoAnalyzer Tool: https://www.idtdna.com/calc/analyzer
[2]Cy5 = 1-[3-[(4-monomethoxytrityloxy)propyl]-1'-[3-[(2-cyanoethyl)-(N,N-diisopropylphosphoramidityl]propyl]-3,3,3',3'-tetramethylindodicarbocyanine chloride; Stock no. 10-5915 (Glen Research)
[3]Spacer18 = 18-O-Dimethoxytritylhexaethyleneglycol,1-[(2-cyanoethyl)-(N,N-diisopropyl)]-phosphoramidite; Stock no. 10-1918 (Glen Research)

Receptor Binding Domain (RBD) Protein Expression

Figure 8:
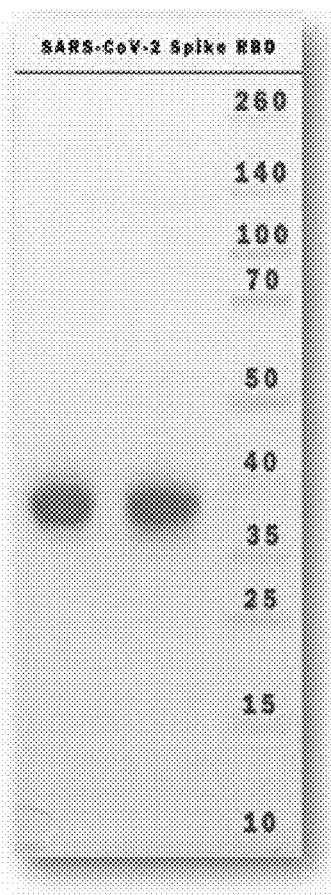
FIG. 8 shows SDS PAGE of SARS-CoV-2 Spike protein RBD. Protein was expressed in Expi293 and purified by Ni-affinity chromatography. Two different batches of sample are shown for demonstration of reproducible expression and purification. The molecular weight of the protein is 40,315.17 Da.

Proteins were expressed using standard protocols in Expi293 system (Thermo Fisher Scientific). First, a vector for the receptor-binding domain (RBD) from SARS-CoV-2 (a.a. 319-541 (RVQPTESIVR FPNITNLCPF GEVFNATRFA SVYAWNRKRI SNCVADYSVL YNSASFSTFK CYGVSPTKLN DLCFTNVYAD SFVIRGDEVR QIAPGQTGKI ADYNYKLPDD FTGCVIAWNS NNLDSKVGGN YNYLYRLFRK SNLKPFERDI STEIYQAGST PCNGVEGFNC YFPLQSYGFQ PTNGVGYQPY RVVVLSFELL HAPATVCGPK KSTNLVKNKC VNFHHHHHH; SEQ ID NO: 10)) was obtained from BEI Resources (NR-52309). The sequence was designed by fusing the RBD sequence with a C-terminal hexahistidine tag and is intended for pCAGGS mammalian expression under the AG promoter. Successful expression was confirmed by SDS-PAGE gel (FIG. 8).

Oligonucleotide Synthesis

Oligonucleotides (Table 2) were generated using an ABI-394 automated DNA synthesizer using standard phosphoramidite chemistry. 3'-cholesteryl-TEG CPG solid supports and phosphoramidites were obtained from Glen Research. Sequences were synthesized with a phosphorothioate backbone using 4,5-dicyanoimidazole as an activator and 3-((Dimethylamino-methylidene)amino)-3H-1,2,4-dithiazole-3-thione as the sulfurizing agent. Following synthesis, the Synthesis of RBD-Encapsulated Liposomal SNAs Dried lipid films of 50 mg of 1,2-dioleoyl-sn-glycero-3-phosphocholine (DOPC, Avanti Polar Lipids) were hydrated with 1 mL of RBD protein (approximately 7 mg/mL in Dulbecco's phosphate buffer saline, PBS) and 1.5 mL of PBS. Liposomes were formed following 20 freeze-thaw cycles (liquid nitrogen and sonication in a 3TC water bath), followed by extrusion to 80-nm. The liposomes were extruded using sequential high-pressure extrusion (Northern Lipids Inc.) using polycarbonate filters with pore sizes of 200, 100, and 80-nm; liposomes were passed through each pore size three times. Following extrusion, the liposomes were concentrated down to approximately 2-3 mL using tangential flow filtration (TFF) using a filter with a pore size of 500 kDa (Spectrum). To remove unencapsulated RBD, the solution was either passed through the TFF membrane an additional 2 times or was dialyzed overnight using a 1000 kDa molecular weight cut off membrane against 3.5 L of PBS, depending on time constraints. The liposome concentration was determined using a phosphatidylcholine (PC) assay kit (Sigma), assuming an 80 nm liposome contains 49,974 lipids per liposome based on the equation below.

$$N = 17.69 \times \left[ \left(\frac{d}{2}\right)^2 + \left(\frac{d}{2} - 5\right)^2 \right]$$

where d is the diameter of the liposome and N is the total number of lipids per liposome.

The amount of RBD encapsulated was measured using a BCA assay (Thermo-Fisher) after bursting liposomes with 1% SDS. The loading of protein per liposome was calculated by dividing the protein concentration over the liposome concentration.

To form SNAs, 3' cholesterol-terminated CpG 1826 or CpG 7909 DNA were added to the liposomes in one of the three oligonucleotide to liposome ratios defined: 75:1, 150: 1, or 200:1, depending on the experiment. Solutions were incubated at 37° C. overnight and stored at 4° C.

Characterization of RBD-Loaded Liposomal SNAs

Figure 9:
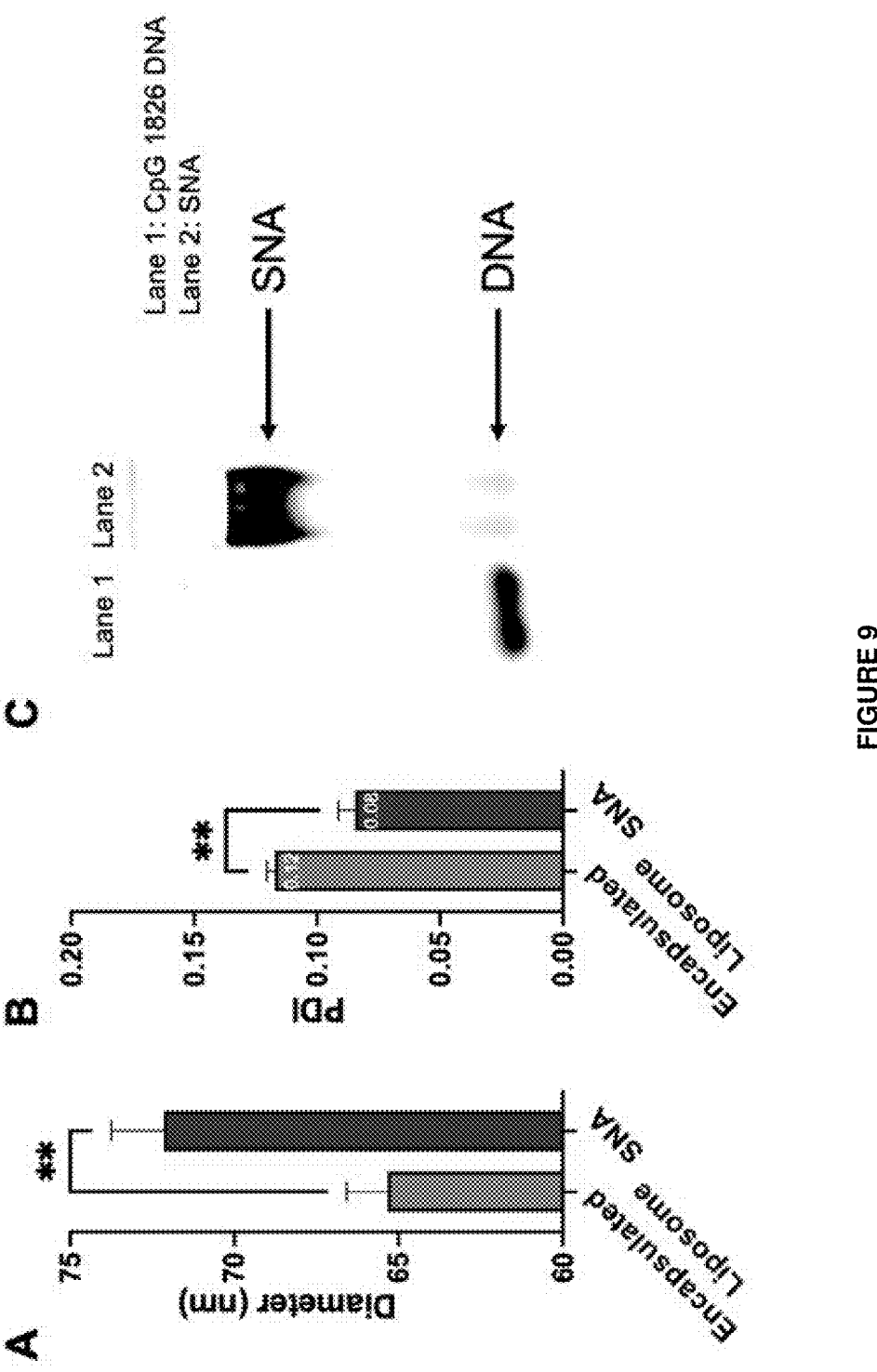
FIG. 9 shows SNA formation confirmed through dynamic light scattering (DLS) and agarose gel electrophoresis. (A) DLS demonstrates a significant increase in diameter and (B) a decrease in polydispersity index (PDI) as a result of addition of the DNA shell. (C) Agarose gel electrophoresis highlights the mobility shift of DNA as a result of SNA formation.

Successful SNA formation was characterized by dynamic light scattering (DLS, Malvern Zetasizer) and visualized by agarose gel electrophoresis. Free linear Cyanine 5-fluorophore-labeled DNA (Table 2), CpG 1826 Cy5 Fluorophore-labeled) and formed SNAs were loaded into a 1% agarose gel on ice and run at 70V for 45 minutes prior to imaging with a Chemidoc Gel Scanner (BioRad) (FIG. 9).

In Vitro Human Peripheral Blood Mononuclear Cell (hPBMC) B Cell Activation

Human PBMCs were thawed from storage in liquid nitrogen in a water bath. Cells were mixed and added to 10 mL of RPMI containing 10% heat-inactivated fetal bovine serum (HI-FBS) and 1% Penicillin-Streptomycin (denoted herein as RPMI+/+). The solution was centrifuged at 300×g for 10 minutes to pellet the cells. The supernatant was aspirated, and the cells were resuspended in 4 mL of media to count using a Vi-Cell. Cells were diluted to a concentration of $1 \times 10^6$ cells/mL and 100 μL of cell stock was added to wells in a 96 round bottom plate. Respective samples were added to cells in 100 μL volume so that the final concentrations were 5 and 124 nM by RBD protein and CpG 7909 DNA, respectively. After either 1 or 3 days, samples were transferred to flow inserts and washed with 600 μL of PBS. Tubes were spun at 1200 rpm for 5 minutes, after which the supernatant was aspirated, and the samples were stained at 4° C. for 15 minutes in 100 μL PBS containing a solution of (0.5 μL of: fixable live/dead antibody-UV, CD19-BV421; HLA-DR-PerCP-Cy5.5; CD27-BV605). Cells were then washed with 600 μL PBS, centrifuged at 1200 rpm for 5 minutes, aspirated, and resuspended in 100 μL of fixation buffer (BioLegend). Samples were stored at 4° C. prior to flow cytometry analysis. Cells were analyzed by flow cytometry using a BD FACSymphony flow cytometer, and cell events were gated and analyzed on FlowJo.

In Vivo Immunization in Mice

Mice were generally injected subcutaneously in the abdomen with 1.4 nmol by RBD protein (either as an SNA or as a simple mixture). Volume was kept below 200 μL. Specifically, mice were injected subcutaneously in the abdomen with one of the following treatments diluted in saline. SNA 200 and simple mixture equivalent were dosed at 1.4 nmol by RBD protein, 60 nmol by CpG DNA. SNA 150 was dosed at 1.4 nmol by RBD protein, 44 nmol by CpG DNA. SNA 75 was dosed at 1.4 nmol by RBD protein, 22 nmol by CpG DNA. Alum Admix was dosed at 1.4 nmol by RBD protein, 40 μg by $Al^{3+}$(H. HogenEsch, D. T. O'Hagan, C. B. Fox, Optimizing the utilization of aluminum adjuvants in vaccines: you might just get what you want. npj Vaccines 3, 51 (2018)). Alhyrdogel adjuvant 2% was used as the source (obtained from InvivoGen). MF59 Admix was dosed at 1.4 nmol by RBD protein, 25 μL by AddaVax adjuvant (obtained from InvivoGen) (M. Dupuis, D. M. McDonald, G. Ott, Distribution of adjuvant MF59 and antigen gD2 after intramuscular injection in mice. Vaccine 18, 434-439 (1999)). AS01b Admix was first synthesized as described in WO 96/33739. Briefly, liposomes were made comprising DOPC, cholesterol, and MPLA4 in a ratio of 20:5:1 respectively. These liposomes were added to QS21 (Quil-A, InvivoGen) at a ratio of 1:1 MPLA4:QS21. The dose used was determined by converting the typical human dose to the mouse dose used in Brando, et al, 4.2 μg by QS21 and MPLA4 (C. Brando et al., Murine immune responses to liver-stage antigen 1 protein FMP011, a malaria vaccine candidate, delivered with adjuvant AS01B or AS02A. Infect Immun 75, 838-845 (2007)).

Retro-Orbital Blood Collection

Two weeks following the injection, blood was collected via a retro-orbital blood draw. Animals were anesthetized with isoflurane, and once asleep, a heparin (Sigma) lined pipette was inserted through the conjunctiva and into the orbital sinus by quickly rotating the tube. Approximately 100 μL of blood was drawn and stored at RT for at least 30 minutes to allow the blood to clot. The blood was then centrifuged at 1000×g for 10 minutes, and the supernatant (serum) was carefully removed and transferred to a 96 well plate for downstream analysis. If not used immediately, serum was stored at −80° C.

RBD-Specific IgG Binding Antibodies Via ELISA

A 96 well ELISA Uncoated Plate (BioLegend Nunc™ Maxi Sorp™) was coated with 2.5 μg/mL of RBD protein diluted in 5× ELISA Coating Buffer (BioLegend) for 2 hours at 37° C. After coating, the plate was washed and subsequently blocked for 2 hours at 37° C. with 200 μL of PBS containing 10% FBS and 0.1% Tween-20 (Sigma). Mouse sera were diluted to various dilution concentrations (e.g., 50×, 100×, 500×, 1000×, 2500×, and/or 5000×) in 5× ELISA dilution buffer (eBioscience). Upon completion of blocking, the blocking solution was removed, and 100 uL of each diluted sample was added immediately to each well and the plate was incubated for 1 hour at 37° C. Following incubation, the plate was washed three times with PBS containing 0.1% Tween-20. 100 μL of secondary antibody (Goat anti-mouse IgG-HRP, BioLegend), diluted 1:4000 in 5× ELISA dilution buffer, was added to each well and incubated at room temperature for 1 hour. The solution was washed out with three cycles of PBS containing 0.1% Tween-20. A 1:1 mixture of TMB Reagent A and Reagent B (BioLegend) were made and immediately used by adding 100 uL to each well. The plate was incubated at room temperature in the dark for 3 minutes, at which point, once the color became pronounced, 100 μl of TMB Stop Solution (BioLegend) was added. The absorbance was immediately read at 450 nm using a BioTek Cytation 5. Titers were defined as the reciprocal serum dilution where 450 nm absorbance was at least 0.5 units above the background sample (i.e., naïve sera).

Neutralizing Antibody Surrogate Virus Neutralization Test (sVNT) Assay

Neutralization titers were determined using a GenScript SARS-CoV-2 Surrogate Virus Neutralization Test (sVNT) Kit. Manufacturer's instructions were followed. Briefly, negative Matrix Control (NMC) was made using mouse naïve serum diluted 10-fold with sample dilution buffer. A standard curve was generated using a monoclonal antibody purchased from the manufacturer (MAB, GenScript, A02051) which was first diluted to a final working concentration of 3 µg/mL with sterile water. A standard curve was created by diluting the MAB in NMC at the following concentrations: 300, 150, 75, 37.5, 18.75, 9.38, 4.7 ng/mL. Samples from serum were diluted serially 1:3 starting at a 1:10 dilution and going down to a 1:810 dilution in sample dilution buffer. Positive and negative controls were provided by the manufacturer and used as instructed. HRP functionalized RBD (RBD-HRP) was made into a working solution following the manufacturer's instructions. Upon preparation of all samples, a 96 well flat bottom plate was obtained and 120 µL of each standard curve dilution, 60 µL of each sample dilution, and 60 µL of each positive and negative control were added to individual wells. Immediately after, an equal volume of RBD-HRP working solution was added to each well, and the plate was incubated at 37° C. for 30 minutes. After incubation, 100 uL of these mixtures were immediately transferred to the manufacturer provided ELISA plate pre-coated with ACE2 receptor, and the plate was sealed and incubated at 37° C. for 15 minutes. Wells were then washed four times with 1× wash solution (provided by kit), after which 100 µL of TMB solution was added to each well and incubated at room temperature for 15 minutes, protected from light. Timing was started after the addition of TMB to the first set of well, as per manufacturer's instructions. After 15 minutes, 50 uL of Stop Solution was added to each well in the exact same order as the TMB solution was added. Absorbance at 450 nm was immediately read using a BioTek Cytation 5.

Proteomics Sample Preparation

Total protein content in sera was quantified in order to compare relative amounts of proteins amongst different samples. To do this, a BCA assay was performed (Thermo-Fisher). Samples were sent to the NU Proteomics Core, where they were resuspended in 8 M urea, reduced with 4 mM dithiothreitol, and then alkylated with 18 mM iodoacetamide. The solution was then diluted to <2 M urea (final concentration), and trypsin was added at the final trypsin/protein ratio of 1:100 for overnight incubation at 37° C. The resulting peptides were desalted using solid-phase extraction

44

Spectrometer (Thermo Fisher). Samples were loaded onto a house-packed C18 column and separated with a 5-40% of solvent (0.1% FA in ACN) for 120 minutes by an analytical column (PicoChip, New Objective, Inc. Woburn, MA). MS/MS spectra were searched against the SwissProt *Mus musculus* database using Mascot search engine (Matrix Science, London, UK; version 2.7.0.1). All searches included carbamidomethyl Cys as a fixed modification and oxidized Met; deamidated Asn and Gln; and acetylated N-term as variable modifications. The search result was visualized by Scaffold v 5.0.1 (Proteome Software, INC., Portland, OR). A 1% false discovery rate of the protein with a minimum of two unique peptides were identified. Statistical analysis, specifically a Fisher's exact test with a Benjamini-Hochberg multiple test correction, was performed for comparison between 200 SNA and 150 SNA groups (n=4 and 3 samples per group, respectively).

In Vivo Live Viral Challenge

All work with live SARS-CoV-2 was performed safely in the BSL-3 facility of the Ricketts Regional Biocontainment Laboratory, operated by the University of Chicago following a protocol approved by IACUC of both Northwestern University and the University of Chicago. 6-8 week old female and male B6.Cg-Tg(K18-ACE2)₂Prlmn/J (k18-hACE2) mice (Jackson) were challenged with 2×104 PFU of USA-WA1/2020 SARS-CoV-2 (2019-nCoV) in 20 µl by intranasal injection. Mice were monitored twice daily to record clinical symptoms and weighed daily. Categories in clinical scoring can be found in Table 3. Animals that lost 20% of their baseline body weight or had a clinical score of 3 were sacrificed for humane reasons. Animals that did not meet these criteria were monitored for up to 12 days while in the BSL-3 facility. On day of sacrifice (either day five for PBS or admix treated groups or day twelve for SNA treated groups), animals were killed and subjected to necropsy to remove the lungs. One part of the lungs was homogenized in 2% DMEM to measure viral titers (see Quantification of Virus in Lung by Plaque Assay) whereas the other part was fixed in paraffin embedded blocks for histopathology.

TABLE 3

| Clinical Scoring Table for in vivo Lethal Viral Challenge Study | |
| --- | --- |
| Clinical Score | Description |
| 0 | (Pre-Inoculation) - Mice Are Bright, Alert, Active, Normal Fur Coat and Posture. |
| 1 | (Post-Inoculation) - Mice Are Bright, Alert, Active, Normal Fur Coat and Posture, No Weight Loss. |
| 1.5 | (Post-Inoculation) - Mice Present with Slightly Ruffled Fur but Are Active OR Weight Loss Might Occur But Does Not Reach 2.5%; Recovery Can Be Expected. |
| 2 | (Post-Inoculation) - Ruffled Fur OR Less Active OR <5% Weight Loss; Recovery Might Occur. |
| 2.5 | (Post-Inoculation) - Ruffled Fur OR Not Active but Moves When Touched OR Hunched Posture OR Difficulty Breathing OR Weight Loss 5-10%; Recovery Is Unlikely But Still Might Occur |
| 3 | (Post-Inoculation) - Ruffled Fur OR Inactive but Moves When Touched OR Difficulty Breathing OR Weight Loss At 11-20%; Recovery Is Not Expected |
| 4 | (Post-Inoculation) - Ruffled Fur OR Positioned on Its Side or Back OR Dehydrated OR Difficulty Breathing OR Weight Loss >20% OR Labored Breathing; Recovery Is Not Expected |
| 5 | (Post-Inoculation) - Death | on a Pierce C18 Spin column. The eluates were dried under a vacuum and reconstituted with 5% ACN/0.1% FA in water.

Mass Spectrometry Analysis and Database Search

The obtained peptides were analyzed by LC-MS/MS using a Dionex UltiMate 3000 Rapid Separation nanoLC and a Q Exactive™ HF Hybrid Quadrupole-Orbitrap Mass Lung Histopathology Formalin-fixed lung sections were embedded in paraffin blocks released from the BSL-3 facility after verifying the absence of infectious virus and used to generate slides for staining studies by the Mouse Histology & Phenotyping Laboratory (MHPL) center, Northwestern University, Chicago as previously described (L. Hassler et al., A novel soluble ACE2 protein totally protects from lethal disease caused by SARS-CoV-2 infection. bioRxiv 10.1101/2021.03.12.435191, 2021.2003.2012.435191 (2021)). Histopathology was evaluated by two expert lung pathologists. One blinded lung pathologist evaluated the severity and presence of lung injury using a scoring system recently described in k18-hACE2 mice infected with SARS-CoV-2 (L. Hassler et al., A novel soluble ACE2 protein totally protects from lethal disease caused by SARS-CoV-2 infection. bioRxiv 10.1101/2021.03.12.435191, 2021.2003.2012.435191 (2021); J. Zheng et al., COVID-19 treatments and pathogenesis including anosmia in K18-hACE2 mice. Nature 589, 603-607 (2021)). The alterations scored were mononuclear infiltrates, neutrophils, edema, and necrosis. The scale was as follows: 0=no detection, 1=uncommon detection in <5% lung fields (200 Å~), 2=detectable in up to 30% of lung fields, 3=detectable in 33-66% of lung fields and 4=detectable in >66% of lung fields. Neutrophil infiltration was evaluated on a scale of 0-3 as follows: 0=within normal range, 1=scattered polymorphonuclear leukocytes (PMNs) sequestered in septa, 2=score 1 and solitary PMNs extravasated in airspaces, 3=score 2 plus and aggregates in vessel and airspaces.

Quantification of Virus in Lung by Plaque Assay

Tissue samples were collected in DMEM containing 2% FBS and were homogenized with 1.4 mm ceramic beads in a tissue homogenizer using two 30 s pulses. Samples were subsequently centrifuged at 1000×g for 5 minutes and the supernatant was collected and serially diluted 10-fold to infect VeroE6 cells. Cells were infected for 1 hour, after which inoculum was removed and 1.25% methylcellulose DMEM solution was added to the cells and incubated for 3 days. Plates were fixed in 1:10 formalin and stained with crystal violet for 1 hour for counting to determine plaque forming units (PFU)/ml. Samples were normalized to mg of lung tissue, which was determined prior to homogenization.

Statistical Analysis

All values shown in graphs were mean±standard deviation (SD) or standard error of the mean (SEM), as described in each figure caption. Individual biological replicates are shown as points. Group sample size is described in each figure caption. Statistical analysis was performed using GraphPad Prism 9 software and specific analysis is provided in each figure caption. Comparisons between two groups utilized an unpaired t-test. Comparisons assessing more than two groups used an ANOVA with a post-hoc test for multiple comparisons analysis between individual groups. Depending on if the SD between groups could be assumed to be equivalent, either an ordinary one-way or a Brown-Forsythe ANOVA was used. Post-hoc tests employed were either Sidak, Tukey, or Dunnett, depending on the assumptions based on SD differences. No specific preprocessing of data was performed prior to statistical analyses. Significance was defined as $p<0.05$ (*$p<0.05$; $p<0.01$; *$p<0.001$; ****$p<0.0001$; ns=non-significant).

Results

SNA Design and Characterization

Figure 10:
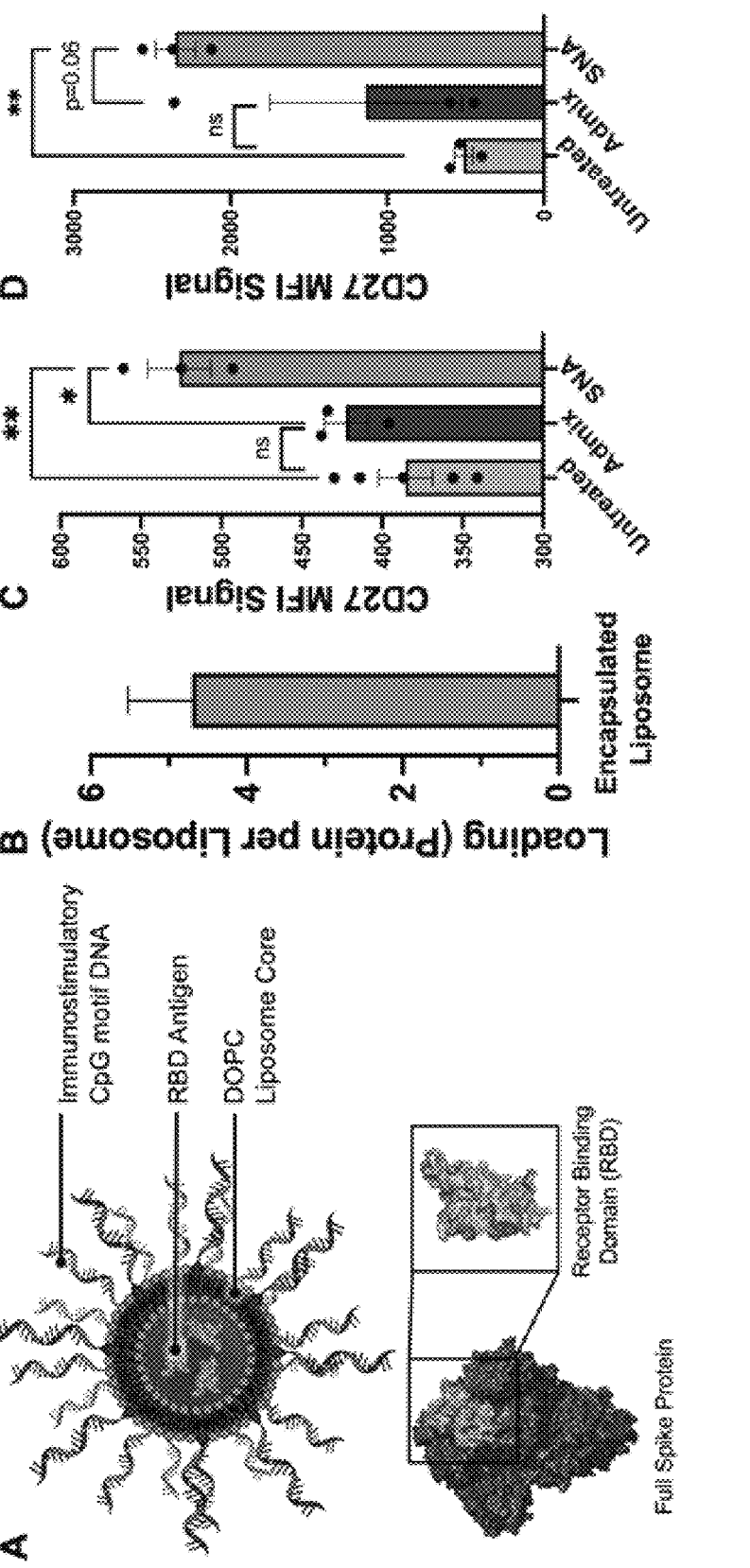
FIG. 10 shows a Spherical Nucleic Acid (SNA) vaccine containing receptor binding domain (RBD) antigen is capable of activating B cells in vitro. (A) (top) A schematic of the SNA used in the Examples herein encapsulating RBD antigen within an 80 nm DOPC liposome core, and radially displaying a shell of TLR9-agonist CpG motif DNA. (bottom) RBD structure (purple) as a subset of the full COVID-19 Spike protein (red). This representation of the full spike protein and RBD was adapted from PDB ID: 6VXX. (B) Minimal batch-to-batch variation of the amount of RBD protein loaded per liposome (mean and 95% confidence interval shown, n=10). (C & D) In vitro activation of hPBMCs to increase expression of CD27 among CD19+B cells. Incubation with hPBMCs was performed for both 1 (C) and 3 (D) days. Mean and SEM shown; analysis was done using an ordinary one-way ANOVA followed by a (C)

To synthesize SNA vaccines capable of raising robust, prophylactic responses against SARS-CoV-2, the modularity of the liposomal SNA was harnessed to simultaneously deliver encapsulated protein antigen and CpG motif DNA adjuvant. The modularity of the SNA platform enables fine-tuned control over vaccine structure, allowing for the rational design of the most effective vaccine. For these studies, the receptor-binding domain (RBD, FIG. 8 of the SARS-CoV-2 Spike protein was used as the antigen because this domain is responsible for recognizing and binding to human cell's angiotensin-converting enzyme 2 (ACE2) receptor and facilitating cellular entry. SNAs were synthesized using previously established protocols (8, 17). Briefly, protein antigens were encapsulated in 80-nm liposomes prepared from 1,2-dioleoyl-sn-glycero-3-phosphocholine (DOPC) films and purified using tangential flow filtration (TFF) to remove any unencapsulated protein. To form SNAs, protein-encapsulated liposomes were incubated with 3'-cholesterol-modified CpG DNA (FIG. 10A). The CpG DNA used was either a human or murine TLR9 agonist sequence depending on the experiment (Table 2). Successful DNA incorporation and SNA formation was confirmed by dynamic light scattering (DLS) and agarose gel electrophoresis, which shows a decrease in electrophoretic mobility commensurate with DNA loading and increased size. (FIG. 9). The average RBD protein loading per liposome across 10 distinct batches was 4.7±1.6 (FIG. 10B). This is equivalent to a loading capacity of 0.52 wt/wt %.

B Cell Activation In Vitro in hPBMCs

A necessary step in effective vaccination is immunological memory carried by memory B cells, as these are easily reactivated upon exposure to antigen (18, 19, 20). Moreover, their activation results in rapid proliferation and differentiation into plasma cells that produce large amounts of higher-affinity antibodies (18, 19). SNAs were therefore assessed for their ability to robustly activate naïve B cells in human peripheral blood mononuclear cells (hPBMCs). For these studies, SNAs comprising a human CpG 7909 oligonucleotide shell were used (Table 2). After one and three days of incubation, cells were measured for the presence of CD27, an activation marker which can contribute to B cell expansion, differentiation, and antibody production (21). A significant difference in CD27 expression was observed when comparing the SNA to simple mixtures of RBD and CpG, termed admix, and when compared to untreated cells (FIGS. 100 and 10D). This can be attributed to the advantageous properties that emerge when utilizing the SNA architecture including but not limited to improved co-delivery of antigen and adjuvant components, increased and rapid cellular uptake, and enhanced resistance to nuclease degradation. While using human cells, this demonstration of B cell activation was in vitro, and does not consider the complexity involved in multi-cell cross talk that leads to robust antibody production. Therefore, the ability of the SNA to stimulate the adaptive immune system in vivo to generate robust, antigen-specific antibody responses was assessed.

In Vivo Antibody Production

RBD IgG-specific binding and neutralizing antibody production following a single subcutaneous injection in 057BL/6 mice (n=3-6 per group) was evaluated. RBD-specific binding antibodies were assessed by ELISA on mouse sera collected two weeks post-prime injection. For SNA-immunized mice, a ca. 1000-fold enhancement in the reciprocal serum end-point antibody titer compared to the simple mixture control (FIG. 11A) was quantified. Furthermore, SNA-treated mice elicited a potent pseudovirus-neutralizing ability, whereby the generated antibodies inhibited 58% of the interaction between RBD and ACE2 at a 1:10 dilution in a surrogate virus neutralization test (sVNT) assay (FIG. 11B). Overall, a ca. 16.5-fold enhancement of final neutralizing antibody titer was measured for SNA-treated mice compared to those that received admix (FIG. 11O), which had no detectable inhibition ability (threshold was 30% inhibition as per manufacturer's specifications) (FIG. 11B).

These assays validated that serum antibodies were more robustly produced with SNA immunization compared to admix vaccination, and also that a single dose of the SNA vaccine generated antibodies that recognized and blocked a pseudoviral RBD domain from binding to an ACE2 receptor. This underscored the importance of structuring components into an SNA architecture in order to achieve enhanced biological and therapeutic responses, as proteins and DNA alone exhibit poor biodistribution to draining lymph nodes and rapid clearance (22). By contrast, these results upheld that SNAs effectively deliver cargo to immune cells in vivo. Moreover, high neutralizing antibody levels are correlated with protection against infection (23); therefore, these results established the potential for SNA vaccines to be a viable vaccination strategy for COVID-19.

Comparison of SNA Performance to Simple Mixtures of RBD and Commercial Adjuvants To further compare the SNA platform against commercially available alternatives that did not consider structure, how the SNA vaccine compared against mixtures of commercial clinically-used adjuvants and the RBD antigen was evaluated. Specifically, Alum, MF59, and AS01b were employed as adjuvants. All of these have been used to protect against infectious diseases, including Hepatitis B or Influenza (24-26). In an assessment of RBD IgG-specific binding antibodies two weeks post-prime, the SNA outperformed all tested simple mixtures of adjuvants, even surpassing the best performing commercial adjuvant AS01b simple mixture by 14-fold. It ultimately reached a reciprocal serum end-point titer of 2464 (FIG. 11D). The simple mixture formulated with alum admix has undetectable binding antibodies indistinguishable from those raised by naïve mice, and MF59 admix had only one responder out of three mice, which had a reciprocal serum end-point titer of 74, 33-fold lower than SNA vaccination. When comparing the SNA against commercial adjuvant-containing simple mixtures in a pseudoviral neutralizing study (FIG. 11E), even the best performing group, AS01b admix, only reached 41 ng/mL neutralizing antibodies in sera, whereas the SNA concentration was nearly 9-fold higher, 339 ng/mL. This trend was similarly observed three weeks post-prime (FIG. 17), where the sera neutralizing antibodies generated from the SNA immunization were highest at 1193 ng/mL, 4-fold greater than the closest admix (AS01b).

Stoichiometry Between Adjuvant and Antigen Impacts Immune Response

As the SNA modularity can be easily tuned, it was sought to understand the impact of the amount of adjuvant DNA loading on the SNA shell. An agarose gel was performed on 80-nm DOPC liposomes to evaluate the range of DNA that could fit on the surface before dissociating (27) (FIG. 12).

This revealed a maximum of ca. 200 DNA strands per liposome (surface density of 1.7 $pmol/cm^2$), which aligns with other liposomal SNA structures (9, 28). To investigate the adjuvant loading dependence on vaccine efficacy, the DNA surface coverage was varied to synthesize three different SNAs containing 75, 150, and 200 strands per liposome, while keeping the encapsulation of protein in the core constant. This provided three different adjuvant:antigen ratios that were ca. 16:1, 32:1, and 43:1, respectively. It was hypothesized that enhanced loading would propagate an initial innate response, which could enhance an adaptive response. Mice were inoculated with one of the three different SNAs or one of three TLR9 admix controls that matched these adjuvant:antigen ratios. Two weeks post-prime injection, RBD-specific binding and neutralizing antibodies were quantified from sera and were plotted against adjuvant loading to determine any linear relationships (FIGS. 13A and 13B). There was a strong positive correlation between adjuvant loading and immune response for SNA immunization ($R^2=0.99$ for both binding and neutralizing antibodies). Moreover, the ability of antibodies generated from the best performing SNA (200 adjuvant strands per liposome), to bind to a mutated RBD of one of the most evasive variants uncovered thus far, B.1.351 (29), was assessed. There was a non-significant difference in the reciprocal serum end-point titer when binding to the RBD B.1.351 variant, termed RBD-SA (FIG. 13C), when compared to the reciprocal serum end-point titer for binding to wildtype RBD. This promising retention of antibody binding ability led to the proposal that the SNA platform can generate robust humoral responses that are resistant to mutational viral changes.

Identification of Upregulated Immunoglobulin (Ig) Classes Using Proteomics

To understand how the different stoichiometries of adjuvant on the SNA induced different levels of binding and neutralizing antibodies, proteomics was performed to assess the expression of different immunoglobulins. Eighteen immunoglobulins (Igs) were identified amongst all the SNA formulations (75, 150, or 200 adjuvant strands/liposome termed 75 SNA, 150 SNA, and 200 SNA, respectively), with an additional five distinct Ig proteins present in the 200 SNA treatment group (FIG. 13D). In particular, the five significant proteins have increased fold changes in the 200 SNA immunization compared to 150 SNA (FIG. 13E). Furthermore, the total spectra of these proteins, an indicator of protein abundance (30), increases as the adjuvant loading increases (FIG. 13F). The IgM antibody was one of the 18 Ig proteins present among all SNA vaccine groups (Table 4) and is the first immunoglobulin class produced in the primary response to antigens (31). The five significant Igs in the 200 SNA group are involved in antigen binding, positive regulation of B cell activation and B cell receptor signaling, Ig receptor binding and mediated immune response, and overall, the adaptive immune response (32). This showed that the increased expression of these proteins and subsequent processes that they are involved in, results in the measurable increase in immune outputs.

TABLE 4

List of Immunoglobulin (Ig) proteins detected by proteomics. Bolded
rows (2, 3, 4, 6, and 7) indicate those that were significant in
a Fisher's Exact T test between the 200 SNA and 150 SNA group.

| Name | Molecular Weight | Fisher's Exact Test (p-value): *(p < 0.0063)$^2$ | Total Spectra Count (Integer avg for group) | | |
|---|---|---|---|---|---|
| | | | 75 SNA | 150 SNA | 200 SNA |
| Immunoglobulin kappa constant | 12 kDa | 0.37 | 4 | 37 | 26 |
| Immunoglobulin heavy constant mu | 50 kDa | <0.00010 | 13 | 20 | 32 |
| Ig gamma-2B chain C region | 44 kDa | <0.00010 | 6 | 12 | 19 |
| Ig kappa chain V-III region ABPC 22/PC 9245 | 12 kDa | 0.00016 | 7 | 12 | 17 |
| Ig gamma-1 chain C region, membrane-bound form | 43 kDa | 0.059 | 4 | 14 | 14 |
| Ig kappa chain V-III region PC 7043 | 12 kDa | 0.00032 | 6 | 10 | 15 |
| Ig kappa chain V-III region PC 2880/PC 1229 | 12 kDa | 0.0011 | 0 | 11 | 15 |
| Ig gamma-3 chain C region | 44 kDa | 0.17 | 2 | 7 | 6 |
| Ig kappa chain V-V region HP R16.7 | 12 kDa | 0.25 | 3 | 4 | 4 |
| H-2 class I histocompatibility antigen, Q10 alpha chain | 37 kDa | 0.53 | 3 | 8 | 5 |
| Ig kappa chain V-II region 26-10 | 12 kDa | 0.079 | 1 | 4 | 5 |
| Ig kappa chain V-V region MOPC 173 | 12 kDa | 0.45 | 1 | 2 | 1 |
| Ig heavy chain V region AC38 205.12 | 13 kDa | 0.4 | 0 | 3 | 3 |
| Ig gamma-2A chain C region secreted form | 37 kDa | 0.32 | 2 | 2 | 2 |
| Ig heavy chain V region 93G7 | 16 kDa | 0.56 | 0 | 1 | 1 |
| Ig heavy chain V-III region HPC76 (Fragment) | 12 kDa | 0.086 | 0 | 0 | 1 |
| Ig kappa chain V-V region MOPC 41 | 14 kDa | 0.18 | 0 | 1 | 1 |
| Ig heavy chain V region HPCG14 | 14 kDa | 0.29 | 0 | 1 | 1 |
| Polymeric immunoglobulin receptor | 85 kDa | 0.47 | 0 | 0 | 0 |
| Ig alpha chain C region | 37 kDa | 1 | 0 | 0 | 0 |

Dosing of SNA Vaccine Enhances Immune Responses

The impact of multiple doses of the best-performing SNA vaccine (200 SNA) on the resulting amplification of immune responses was quantified. Many ongoing vaccines that were granted Emergency Use Authorization or are in development have utilized a prime-boost vaccine schedule to enhance immune responses (33). Therefore, mice were immunized with a prime-boost schedule (boost was two weeks post prime) to assess any elevation in antibody production. Sera were collected from the mice two weeks after the boost, which is 4 weeks (28 days) after the initial prime immunization. An increase in both binding antibodies (FIG. 14A); 6.5-fold) and neutralizing antibodies (FIG. 14B); 126-fold) was observed when comparing sera from two doses to that from one. The admix vaccination did improve with a second administration, but levels of binding and neutralizing antibodies were still 4000-fold and 1500-fold lower, respectively, compared to the SNA immunization (FIG. 14), and proteomics signatures were significantly different (FIG. 18).

Live Viral In Vivo Challenge Using Transgenic ACE2 Mice

As a direct test of vaccine efficacy, a viral challenge study was conducted using transgenic mice that are susceptible to infection through expression of the human ACE2 protein: k18-hACE2 (34, 35). Animals were challenged with a lethal dose of the virus (36-40). The top performing vaccine design (200 SNA) was compared to the admix vaccine, and also to mice receiving only saline (PBS) as a negative control. Mice were given either one or two doses of the SNA or admix vaccine. Mice (n=10 per group, comprising 5 females and 5 males) were challenged with virus two weeks after receiving the final vaccine dose (complete schedule in FIG. 15A). Just prior to viral infection, blood was collected from the mice to verify neutralizing antibody production (FIG. 16). After viral infection, animals were monitored twice daily for signs of disease, and weighed daily. Within the first five days post infection, mice that received either saline or one or two doses of admix vaccine experienced a rapid decline in body weight and an increase in clinical score, both of which indicate that the mice were not protected from the virus (FIGS. 15B and 15C). These animals were euthanized at day 5, as per study protocol, for humane reasons, and lungs were removed to measure viral loads (FIGS. 15D and 15E). In stark contrast, mice that were treated with either one or two doses of the SNA vaccine displayed no evidence of declining health. Body weight and clinical scores remained stable throughout the entire study, and thus survival of the SNA treated mice was 100% (FIG. 15B-FIG. 15D). All surviving animals were killed at day 12 post infection. Lungs from sacrificed mice (day 5 for PBS and admix vaccine either dose, and day 12 for SNA vaccine either dose) were collected and quantified for viral titers measured by plaque assay. Mice receiving either one or two doses of SNA vaccine had no measurable viral titers in the lungs (FIG. 15E). Mice immunized with PBS or either admix dose and sacrificed on day 5, had viral titers around $7 \times 10^1$ or $2$-$3 \times 10^1$ PFU/mL/mg lung, respectively. Histopathological examination of the lungs, performed following methods used in the same transgenic model (J. Zheng et al., COVID-19 treatments and pathogenesis including anosmia in K18-hACE2 mice. Nature 589, 603-607 (2021)), showed extensive neutrophil infiltration for mice that did not receive the SNA vaccine (mean=1.6, 1.85, and 1.95 for PBS-treated, Admix 1, and Admix 2 dose treated mice, respectively) (FIG. 15F). In mice that received the SNA vaccine, neutrophil infiltration was reduced (mean=0.7 and 0.15 for 1 and 2 doses, respectively). This indicated that the SNA vaccine is capable of avoiding or greatly attenuating outcomes of severe COVID-19 pneumonia, which is characterized by elevated neutrophil infiltration (J. Wang et al., Excessive Neutrophils and Neutrophil Extracellular Traps in COVID-19. Front. Immunol. 11 (2020)). Additional histopathological analysis and representative images are shown in FIG. 19). Overall, these results emphasize the impact that the SNA vaccine platform, and more broadly rational vaccinology, can have on elevating antiviral vaccine efficacy.

Discussion

This work established the SNA as an effective platform for antiviral vaccines. Use of the spherical nucleic acid architecture elucidated structure-function relationships of antiviral vaccines, ultimately generating a highly potent COVID-19 vaccine that protected mice in a lethal viral challenge. By utilizing the highly modular SNA architecture, the importance of packaging viral antigens to raise humoral immune responses that can effectively fight a live virus was highlighted. This work has important implications on the design of next generation infectious disease vaccines. It illustrated that antibody production is tunable through simple chemical adjustments (i.e., the adjuvant loading on a liposome), and that a simple change to the ratio of components can greatly alter immunoglobulin expression. This work offers alternative strategies to enhancing antibody responses than traditional approaches which involve administering multiple doses. Importantly, it was also observed that a traditional approach of supplementing a vaccine with adjuvant to enhance an antibody response is not a consistently effective strategy. The results using the SNA, which compositionally is similar to the AS01b simple mixture in that both involve liposomal constructs, suggests that radial display of CpG adjuvant and co-delivery of vaccine components, which the SNA provides, leads to a more effective vaccine that prevented mortality and attenuated lung injury. Consistently, the 3D arrangement of components on the SNA architecture led to significant increases in vaccine functionality compared to numerous tested simple mixtures.

Taken together, this work underscored the SNA's potential to be used as a platform for infectious diseases, and that the concept of rational vaccinology holds equally as true for infectious disease as it does for cancer vaccine applications. Given the SNA's easily adaptable structure to contain any viral antigen and combinations thereof, modulate positions and tune the stoichiometry of each component, and remain stable at room temperature, the SNA is poised to be a rapidly accessible future platform for targets yet to be discovered. When considering the programmability of the SNA architecture, rapid translation to antigenic variants and human adjuvant sequences is easily feasible. Collectively, these results have broad implications for the development of vaccines for COVID-19 and potentially other infectious diseases.

Using SARS-CoV-2 as a relevant case study for infectious disease, this example investigated the structure-function relationships that dictate antiviral spherical nucleic acid (SNA) vaccine efficacy. The example showed that the SNA architecture can be rapidly employed to target COVID-19 through incorporation of the receptor binding domain, and that the resulting vaccine potently activates human cells in vitro and mice in vivo. Furthermore, when challenged with a lethal viral infection, only mice treated with the SNA vaccine survived.

Further experiments like those described herein were conducted using the Omicron variant of the SARS-CoV-2 RBD sequence. The methods for the additional experiments were the same as those described herein above, including the methods described in the section titled "Live Viral In vivo Challenge using Transgenic ACE2 Mice". Specifically, just prior to viral infection, blood was collected from the mice to verify neutralizing antibody production. The method for neutralizing antibody production was performed as described herein in the section titled "Neutralizing Antibody Surrogate Virus Neutralization Test (sVNT) Assay" except the Omicron mutated HRP functionalized RBD was utilized for the Omicron samples. Results of the experiments are shown in FIGS. 20 and 21.

The following references are cited throughout Example 2 according to the number below.

1. Excler, J.-L.; Saville, M.; Berkley, S.; Kim, J. H., Vaccine development for emerging infectious diseases. Nat. Med. 2021, 27 (4), 591-600.
2. Marston, H. D.; Folkers, G. K.; Morens, D. M.; Fauci, A. S., Emerging Viral Diseases: Confronting Threats with New Technologies. Sci. Transl. Med. 2014, 6 (253), 253ps10.
3. Morens, D. M.; Fauci, A. S., Emerging infectious diseases: threats to human health and global stability. PLoS pathogens 2013, 9 (7), e1003467-e1003467.
4. Wei, C.-J.; Crank, M. C.; Shiver, J.; Graham, B. S.; Mascola, J. R.; Nabel, G. J., Next-generation influenza vaccines: opportunities and challenges. Nature Reviews Drug Discovery 2020, 19 (4), 239-252.
5. Wong, S. S.; Webby, R. J., Traditional and new influenza vaccines. Clin. Microbiol. Rev. 2013, 26 (3), 476-92.
6. Tregoning, J. S.; Russell, R. F.; Kinnear, E., Adjuvanted influenza vaccines. Hum. Vaccin. Immunother. 2018, 14 (3), 550-564.
7. Kanekiyo, M.; Wei, C.-J.; Yassine, H. M.; McTamney, P. M.; Boyington, J. C.; Whittle, J. R. R.; Rao, S. S.; Kong, W.-P.; Wang, L.; Nabel, G. J., Self-assembling influenza nanoparticle vaccines elicit broadly neutralizing H1 N1 antibodies. Nature 2013, 499 (7456), 102-106.
8. Wang, S.; Qin, L.; Yamankurt, G.; Skakuj, K.; Huang, Z.; Chen, P.-C.; Dominguez, D.; Lee, A.; Zhang, B.; Mirkin, C. A., Rational vaccinology with spherical nucleic acids. Proceedings of the National Academy of Sciences 2019, 116 (21), 10473-10481.
9. Yamankurt, G.; Berns, E. J.; Xue, A.; Lee, A.; Bagheri, N.; Mrksich, M.; Mirkin, C. A., Exploration of the nanomedicine-design space with high-throughput screening and machine learning. Nature biomedical engineering 2019, 3 (4), 318-327.
10. Qin, L.; Wang, S.; Dominguez, D.; Long, A.; Chen, S.; Fan, J.; Ahn, J.; Skakuj, K.; Huang, Z.; Lee, A.; Mirkin, C.; Zhang, B., Development of Spherical Nucleic Acids for Prostate Cancer Immunotherapy. Front. Immunol. 2020, 11, 1333-1333.
11. Mirkin, C. A.; Letsinger, R. L.; Mucic, R. C.; Storhoff, J. J., A DNA-based method for rationally assembling nanoparticles into macroscopic materials. Nature 1996, 382 (6592), 607-9.
12. Seferos, D. S.; Prigodich, A. E.; Giljohann, D. A.; Patel, P. C.; Mirkin, C. A., Polyvalent DNA nanoparticle conjugates stabilize nucleic acids. Nano Lett. 2009, 9 (1), 308-311.
13. Cutler, J. I.; Auyeung, E.; Mirkin, C. A., Spherical Nucleic Acids. Journal of the American Chemical Society 2012, 134 (3), 1376-1391.
14. Choi, C. H. J.; Hao, L.; Narayan, S. P.; Auyeung, E.; Mirkin, C. A., Mechanism for the endocytosis of spherical nucleic acid nanoparticle conjugates. Proc. Natl. Acad. Sci. U.S.A 2013, 110 (19), 7625-7630.

15. Banga, R. J.; Chernyak, N.; Narayan, S. P.; Nguyen, S. T.; Mirkin, C. A., Liposomal Spherical Nucleic Acids. Journal of the American Chemical Society 2014, 136 (28), 9866-9869.

16. Radovic-Moreno, A. F.; Chernyak, N.; Mader, C. C.; Nallagatla, S.; Kang, R. S.; Hao, L.; Walker, D. A.; Halo, T. L.; Merkel, T. J.; Rische, C. H.; Anantatmula, S.; Burkhart, M.; Mirkin, C. A.; Gryaznov, S. M., Immuno-modulatory spherical nucleic acids. Proc. Natl. Acad. Sci. U.S.A 2015, 112 (13), 3892-7.

17. Callmann, C. E.; Cole, L. E.; Kusmierz, C. D.; Huang, Z.; Horiuchi, D.; Mirkin, C. A., Tumor cell lysate-loaded immunostimulatory spherical nucleic acids as therapeutics for triple-negative breast cancer. Proc. Natl. Acad. Sci. U.S.A 2020, 117 (30), 17543-17550.

18. Palm, A.-K. E.; Henry, C., Remembrance of Things Past: Long-Term B Cell Memory After Infection and Vaccination. Front. Immunol. 2019, 10, 1787-1787.

19. Siegrist, C.-A., Chapter 2—Vaccine immunology. In Vaccines (Fifth Edition), Plotkin, S. A.; Orenstein, W. A.; Offit, P. A., Eds. W. B. Saunders: Edinburgh, 2008; pp 17-36.

20. Chapter 14—B Cell Memory and Plasma Cell Development. In Molecular Biology of B Cells (Second Edition), Alt, F. W.; Honjo, T.; Radbruch, A.; Reth, M., Eds. Academic Press: London, 2015; pp 227-249.

21. Wu, Y.-C. B.; Kipling, D.; Dunn-Walters, D., The Relationship between CD27 Negative and Positive B Cell Populations in Human Peripheral Blood. Front. Immunol. 2011, 2 (81).

22. Ezan, E., Pharmacokinetic studies of protein drugs: Past, present and future. Advanced Drug Delivery Reviews 2013, 65 (8), 1065-1073.

23. Lau, E. H. Y.; Tsang, 0. T. Y.; Hui, D. S. C.; Kwan, M. Y. W.; Chan, W.-H.; Chiu, S. S.; Ko, R. L. W.; Chan, K. H.; Cheng, S. M. S.; Perera, R. A. P. M.; Cowling, B. J.; Poon, L. L. M.; Peiris, M., Neutralizing antibody titres in SARS-CoV-2 infections. Nature Communications 2021, 12 (1).

24. Reed, S. G.; Orr, M. T.; Fox, C. B., Key roles of adjuvants in modern vaccines. Nat. Med. 2013, 19 (12), 1597-1608.

25. Sarkar, I.; Garg, R.; van Drunen Littel-van den Hurk, S., Selection of adjuvants for vaccines targeting specific pathogens. Expert review of vaccines 2019, 18 (5), 505-521.

26. CDC Adjuvants and Vaccines. https://www.cdc.gov/vaccinesafety/concerns/adjuvants.html.

27. Meckes, B.; Banga, R. J.; Nguyen, S. T.; Mirkin, C. A., Enhancing the Stability and Immunomodulatory Activity of Liposomal Spherical Nucleic Acids through Lipid-Tail DNA Modifications. Small 2018, 14 (5), 1702909.

28. Callmann, C. E.; Kusmierz, C. D.; Dittmar, J. W.; Broger, L.; Mirkin, C. A., Impact of Liposomal Spherical Nucleic Acid Structure on Immunotherapeutic Function. ACS Central Science 2021, 7 (5), 892-899.

29. CDC SARS-CoV-2 Variant Classifications and Definitions. https://www.cdc.gov/coronavirus/2019-ncov/variants/variant-info.html.

30. Lundgren, D. H.; Hwang, S. I.; Wu, L.; Han, D. K., Role of spectral counting in quantitative proteomics. Expert Rev Proteomics 2010, 7 (1), 39-53.

31. Schroeder, H. W., Jr.; Cavacini, L., Structure and function of immunoglobulins. J Allergy Clin Immunol 2010, 125 (2 Suppl 2), S41-52.

32. The UniProt, C., UniProt: the universal protein knowledgebase in 2021. Nucleic Acids Res. 2021, 49 (D1), D480-D489.

33. Barros-Martins, J.; Hammerschmidt, S. I.; Cossmann, A.; Odak, I.; Stankov, M. V.; Morillas Ramos, G.; Dopfer-Jablonka, A.; Heidemann, A.; Ritter, C.; Friedrichsen, M.; Schultze-Florey, C.; Ravens, I.; Willenzon, S.; Bubke, A.; Ristenpart, J.; Janssen, A.; Ssebyatika, G.; Bernhardt, G.; Munch, J.; Hoffmann, M.; Pohlmann, S.; Krey, T.; Bošnjak, B.; Forster, R.; Behrens, G. M. N., Immune responses against SARS-CoV-2 variants after heterologous and homologous ChAdOx1 nCoV-19/BNT162b2 vaccination. Nat. Med. 2021.

34. McCray, P. B., Jr.; Pewe, L.; Wohlford-Lenane, C.; Hickey, M.; Manzel, L.; Shi, L.; Netland, J.; Jia, H. P.; Halabi, C.; Sigmund, C. D.; Meyerholz, D. K.; Kirby, P.; Look, D. C.; Perlman, S., Lethal infection of K18-hACE2 mice infected with severe acute respiratory syndrome coronavirus. J. Virol. 2007, 81 (2), 813-21.

35. Hassler, L.; Wysocki, J.; Gelarden, I.; Tomatsidou, A.; Gula, H.; Nicoleascu, V.; Randall, G.; Henkin, J.; Yeldandi, A.; Bathe, D., A novel soluble ACE2 protein totally protects from lethal disease caused by SARS-CoV-2 infection. bioRxiv 2021, 2021.03.12.435191.

36. Zheng, J.; Wong, L.-Y. R.; Li, K.; Verma, A. K.; Ortiz, M. E.; Wohlford-Lenane, C.; Leidinger, M. R.; Knudson, C. M.; Meyerholz, D. K.; McCray, P. B., Jr.; Perlman, S., COVID-19 treatments and pathogenesis including anosmia in K18-hACE2 mice. Nature 2021, 589 (7843), 603-607.

37. Winkler, E. S.; Bailey, A. L.; Kafai, N. M.; Nair, S.; McCune, B. T.; Yu, J.; Fox, J. M.; Chen, R. E.; Earnest, J. T.; Keeler, S. P.; Ritter, J. H.; Kang, L.-I.; Dort, S.; Robichaud, A.; Head, R.; Holtzman, M. J.; Diamond, M. S., SARS-CoV-2 infection of human ACE2-transgenic mice causes severe lung inflammation and impaired function. Nat. Immunol. 2020, 21 (11), 1327-1335.

38. Golden, J. W.; Cline, C. R.; Zeng, X.; Garrison, A. R.; Carey, B. D.; Mucker, E. M.; White, L. E.; Shamblin, J. D.; Brocato, R. L.; Liu, J.; Babka, A. M.; Rauch, H. B.; Smith, J. M.; Hollidge, B. S.; Fitzpatrick, C.; Badger, C. V.; Hooper, J. W., Human angiotensin-converting enzyme 2 transgenic mice infected with SARS-CoV-2 develop severe and fatal respiratory disease. JCI Insight 2020, 5 (19).

39. Silvas Jesus, A.; Vasquez Desarey, M.; Park, J.-G.; Chiem, K.; Allué-Guardia, A.; Garcia-Vilanova, A.; Platt Roy, N.; Miorin, L.; Kehrer, T.; Cupic, A.; Gonzalez-Reiche Ana, S.; Bakel Harm, v.; Garcia-Sastre, A.; Anderson, T.; Torrelles Jordi, B.; Ye, C.; Martinez-Sobrido, L.; Parrish Colin, R., Contribution of SARS-CoV-2 Accessory Proteins to Viral Pathogenicity in K18 Human ACE2 Transgenic Mice. J. Virol. 95 (17), e00402-21.

40. Moreau, G. B.; Burgess, S. L.; Sturek, J. M.; Donlan, A. N.; Petri, W. A.; Mann, B. J., Evaluation of K18-hACE2 Mice as a Model of SARS-CoV-2 Infection. Am J Trop Med Hyg 2020, 103 (3), 1215-1219.

What is claimed is:

1. A spherical nucleic acid (SNA) comprising:
   (a) a nanoparticle core, wherein the nanoparticle core is a liposomal core or a lipid nanoparticle core;
   (b) a shell of oligonucleotides attached to the external surface of the nanoparticle core, the shell of oligonucleotides comprising one or more immunostimulatory oligonucleotides; and
   (c) a coronavirus antigen or a nucleic acid that encodes a coronavirus antigen encapsulated in the nanoparticle core.

2. The SNA of claim 1, wherein the coronavirus antigen is receptor binding domain (RBD) (SEQ ID NO: 4), S1 subunit of Spike (SEQ ID NO: 5), SARS-COV-2 Spike (SEQ ID NO: 2), a variant of any of the foregoing, or a combination thereof.

3. The SNA of claim 1, wherein the coronavirus antigen comprises or consists of a sequence that is at least 80% identical to receptor binding domain (RBD) (SEQ ID NO: 4), S1 subunit of Spike (SEQ ID NO: 5), SARS-COV-2 Spike (SEQ ID NO: 2), SARS-COV-2 surface glycoprotein (SEQ ID NO: 14), SARS-COV-2 RBD (SEQ ID NO: 15), SARS-COV-2 Omicron variant RBD (SEQ ID NO: 16), RBD (SEQ ID NO: 17), or a combination thereof.

4. The SNA of claim 1, wherein at least about 0.5 milligram (mg) of the coronavirus antigen is encapsulated in the nanoparticle core per micromole (μmol) of oligonucleotides in the shell of oligonucleotides.

5. The SNA of claim 4, wherein about 0.5 mg to about 10 mg of the coronavirus antigen is encapsulated in the nanoparticle core per micromole (μmol) of oligonucleotides in the shell of oligonucleotides.

6. The SNA of claim 1, wherein the nanoparticle core is a lipid nanoparticle core.

7. The SNA of claim 1, wherein the shell of oligonucleotides comprises DNA, RNA, or a combination thereof.

8. The SNA of claim 1, wherein the nanoparticle core comprises DNA, RNA, or a combination thereof encapsulated therein.

9. The SNA of claim 1, wherein the ratio of oligonucleotides in the shell of oligonucleotides to the coronavirus antigen encapsulated in the nanoparticle core is about 10:1 to about 70:1 (number of oligonucleotides in the shell of oligonucleotides to the number of coronavirus antigen molecules encapsulated in the nanoparticle core).

10. The SNA of claim 9, wherein the ratio of oligonucleotides in the shell of oligonucleotides to the coronavirus antigen encapsulated in the nanoparticle core is about 16:1.

11. The SNA of claim 9, wherein the ratio of oligonucleotides in the shell of oligonucleotides to the coronavirus antigen encapsulated in the nanoparticle core is about 32:1.

12. The SNA of claim 9, wherein the ratio of oligonucleotides in the shell of oligonucleotides to the coronavirus antigen encapsulated in the nanoparticle core is about 43:1.

13. The SNA of claim 1, wherein the shell of oligonucleotides comprises a targeting oligonucleotide, an inhibitory oligonucleotide, or a combination thereof.

14. The SNA of claim 1, wherein the immunostimulatory oligonucleotide is a CpG-motif containing oligonucleotide, a double-stranded DNA oligonucleotide, or a single-stranded RNA oligonucleotide.

15. The SNA of claim 6, wherein each of the immunostimulatory oligonucleotides is a toll-like receptor (TLR) agonist.

16. A pharmaceutical formulation comprising the SNA of claim 1 and a pharmaceutically acceptable carrier or diluent.

17. An antigenic composition comprising the SNA of claim 1 in a pharmaceutically acceptable carrier, diluent, stabilizer, preservative, or adjuvant, wherein the antigenic composition is capable of generating an immune response including antibody generation or a protective immune response in a mammalian subject.

18. The SNA of claim 6, wherein the nucleic acid is mRNA.

19. The SNA of claim 6, wherein the lipid nanoparticle core comprises an ionizable lipid, a phospholipid, a sterol, and a lipid-polyethylene glycol (lipid-PEG) conjugate.

20. The SNA of claim 19, wherein each oligonucleotide in the shell of oligonucleotides is covalently attached to the exterior of the lipid nanoparticle core through the lipid-PEG conjugate.

21. The SNA of claim 1, wherein the nanoparticle core is a liposomal core.

22. The SNA of claim 21, wherein the liposomal core comprises a plurality of lipid groups.

23. The SNA of claim 22, wherein the plurality of lipid groups comprises a lipid selected from the group consisting of the phosphatidylcholine, phosphatidylglycerol, and phosphatidylethanolamine families of lipids.

24. The SNA of claim 1, wherein at least one oligonucleotide in the shell of oligonucleotides is attached to the exterior of the liposomal or lipid nanoparticle core through a lipid anchor group.

25. The SNA of claim 24, wherein the lipid anchor group is attached to the 5' end or the 3' end of the at least one oligonucleotide.

26. The SNA of claim 24, wherein the lipid anchor group is tocopherol or cholesterol.

27. The SNA of claim 1, wherein the shell of oligonucleotides comprises DNA oligonucleotides and RNA oligonucleotides.

28. The SNA of claim 1, wherein the shell of oligonucleotides comprises single-stranded DNA, double-stranded DNA, single-stranded RNA, double-stranded RNA, or a combination thereof.

29. The SNA of claim 6, wherein the nanoparticle core comprises single-stranded DNA, double-stranded DNA, single-stranded RNA, double-stranded RNA, or a combination thereof encapsulated therein.

30. The SNA of claim 1, wherein the shell of oligonucleotides comprises at least 200 oligonucleotides.

31. The SNA of claim 1, wherein the shell of oligonucleotides is attached to the external surface of the nanoparticle core at a surface density of about 2 pmol/cm$^2$ to about 200 pmol/cm$^2$.

32. The SNA of claim 6, wherein each oligonucleotide in the shell of oligonucleotides is about 10 to about 50 nucleotides in length.

33. The SNA of claim 32, wherein each oligonucleotide in the shell of oligonucleotides is about 20 to about 30 nucleotides in length.

34. The SNA of claim 6, wherein diameter of the SNA is about 10 nanometer (nm) to about 150 nm.

35. The SNA of claim 1, wherein diameter of the SNA is less than or equal to about 50 nanometers.

36. The SNA of claim 6, wherein each oligonucleotide in the shell of oligonucleotides is an immunostimulatory oligonucleotide.

37. The SNA of claim 15, wherein the TLR is toll-like receptor 9 (TLR9).

38. A method of producing an immune response to a coronavirus antigen in a subject, comprising administering to the subject an effective amount of the antigenic composition of claim 17, thereby producing an immune response to the viral antigen in the subject.

39. A method of treating a coronavirus infection in a subject in need thereof, comprising administering to the subject an effective amount of the SNA of claim 1, thereby treating the coronavirus infection in the subject.

40. The method of claim 38, wherein the administering is intravenous, intraperitoneal, intranasal, subcutaneous, or intramuscular.

41. The method of claim 38, wherein the administering comprises at least one dose of the antigenic composition.

* * * * *

SEQUENCE LISTING

<160> NUMBER OF SEQ ID NOS: 17

<210> SEQ ID NO 1
<211> LENGTH: 8537
<212> TYPE: DNA
<213> ORGANISM: Artificial Sequence
<220> FEATURE:
<223> OTHER INFORMATION: Synthetic

<400> SEQUENCE: 1
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtcgagg tgagccccac gttctgcttc actctcccca     420
tctccccccc ctccccaccc ccaattttgt atttatttat tttttaatta ttttgtgcag     480 cgatggggc gggggggggg ggggcgcgcg ccaggcgggg cggggcgggg cgaggggcgg     540
ggcggggcga ggcggagagg tgcggcggca gccaatcaga gcggcgcgct ccgaaagttt     600 cctttttatgg cgaggcggcg gcggcggcgg ccctataaaa agcgaagcgc gcggcgggcg     660
ggagtcgctg cgcgcgctgc cttcgccccg tgccccgctc cgccgccgcc tcgcgccgcc     720
cgccccggct ctgactgacc gcgttactcc cacaggtgag cgggcgggac ggcccttctc     780
ctccgggctg taattagcgc ttggtttaat gacggcttgt ttcttttctg tggctgcgtg     840
aaagccttga ggggctccgg gagggccctt tgtgcggggg gagcggctcg ggggtgcgt     900 gcgtgtgtgt gtgcgtgggg agcgccgcgt gcggctccgc gctgcccggc ggctgtgagc     960
gctgcgggcg cggcgcgggg ctttgtgcgc tccgcagtgt gcgcgagggg agcgcggccg    1020
ggggcggtgc cccgcggtgc gggggggggct gcgaggggaa caaaggctgc gtgcggggtg    1080
tgtgcgtggg ggggtgagca ggggtgtgg gcgcgtcggt cgggctgcaa ccccccctgc    1140
acccccctcc ccgagttgct gagcacggcc cggcttcggg tgcggggctc cgtacggggc    1200
gtggcgcggg gctcgccgtg ccgggcgggg ggtggcggca ggtggggggtg ccgggcgggg    1260 cggggccgcc tcgggccggg gagggctcgg gggaggggcg cggcggcccc cggagcgccg    1320
gcggctgtcg aggcgcggcg agccgcagcc attgcctttt atggtaatcg tgcgagaggg    1380
cgcagggact tcctttgtcc caaatctggc ggagccgaaa tctgggaggc gccgccgcac    1440
cccctctagc gggcgcgggg cgaagcggtg cggcgccggc aggaaggaaa tgggcgggga    1500
gggccttcgt gcgtcgccgc gccgccgtcc ccttctccct ctccagcctc ggggctgtcc    1560
gcggggggac ggctgccttc gggggggacg gggcagggcg gggttcggct tctggcgtgt    1620
gaccggcggc tctagagcct ctgctaacca tgttcatgcc ttcttctttt tcctacagct    1680
cctgggcaac gtgctggtta ttgtgctgtc tcatcatttt ggcaaaggcc accatgttcg    1740
tgtttctggt gctgctgcct ctggtgtcca gccagtgtgt gaacctgacc acaagaaccc    1800
agctgcctcc agcctacacc aacagcttta ccagaggcgt gtactacccc gacaaggtgt    1860
tcagatccag cgtgctgcac tctacccagg acctgttcct gcctttcttc agcaacgtga    1920
cctggttcca cgccatccac gtgtccggca ccaatggcac caagagattc gacaaccccg    1980
tgctgccctt caacgacggg gtgtactttg ccagcaccga gaagtccaac atcatcagag    2040

-continued

```
gctggatctt cggcaccaca ctggacagca agacccagag cctgctgatc gtgaacaacg   2100
ccaccaacgt ggtcatcaaa gtgtgcgagt tccagttctg caacgacccc ttcctgggcg   2160
tctactatca caagaacaac aagagctgga tggaaagcga gttccgggtg tacagcagcg   2220
ccaacaactg caccttcgag tacgtgtccc agcctttcct gatggacctg gaaggcaagc   2280
agggcaactt caagaacctg cgcgagttcg tgttcaagaa catcgacggc tacttcaaga   2340
tctacagcaa gcacacccct atcaacctcg tgcgggatct gcctcagggc ttctctgctc   2400
tggaacccct ggtggatctg cccatcggca tcaacatcac ccggtttcag acactgctgg   2460
ccctgcacag aagctacctg acacctggcg atagcagcag cggatggaca gctggtgccg   2520
ccgcttacta tgtgggctac ctgcagccta gaacctttct gctgaagtac aacgagaacg   2580
gcaccatcac cgacgccgtg gattgtgctc tggatcctct gagcgagaca aagtgcaccc   2640
tgaagtcctt caccgtggaa aagggcatct accagaccag caacttccgg gtgcagccca   2700
ccgaatccat cgtgcggttc cccaatatca ccaatctgtg ccccttcggc gaggtgttca   2760
atgccaccag attcgcctct gtgtacgcct ggaaccggaa gcggatcagc aattgcgtgg   2820
ccgactactc cgtgctgtac aactccgcca gcttcagcac cttcaagtgc tacggcgtgt   2880
cccctaccaa gctgaacgac ctgtgcttca caaacgtgta cgccgacagc ttcgtgatcc   2940
ggggagatga agtgcggcag attgcccctg gacagacagg caagatcgcc gactacaact   3000
acaagctgcc cgacgacttc accggctgtg tgattgcctg aacagcaac aacctggact   3060 ccaaagtcgg cggcaactac aattacctgt accggctgtt ccggaagtcc aatctgaagc   3120
ccttcgagcg ggacatctcc accgagatct atcaggccgg cagcacccct tgtaacggcg   3180
tggaaggctt caactgctac ttcccactgc agtcctacgg ctttcagccc acaaatggcg   3240
tgggctatca gcccctacaga gtggtggtgc tgagcttcga actgctgcat gcccctgcca   3300
cagtgtgcgg ccctaagaaa agcaccaatc tcgtgaagaa caaatgcgtg aacttcaact   3360
tcaacggcct gaccggcacc ggcgtgctga cagagagcaa caagaagttc ctgccattcc   3420
agcagtttgg ccgggatatc gccgatacca cagacgccgt tagagatccc cagacactgg   3480
aaatcctgga catcacccct tgcagcttcg gcggagtgtc tgtgatcacc cctggcacca   3540
acaccagcaa tcaggtggca gtgctgtacc aggacgtgaa ctgtaccgaa gtgcccgtgg   3600
ccattcacgc cgatcagctg acacctacat ggcgggtgta ctccaccggc agcaatgtgt   3660
ttcagaccag agccggctgt ctgatcggag ccgagcacgt gaacaatagc tacgagtgcg   3720
acatccccat cggcgctggc atctgtgcca gctaccagac acagacaaac agccccgcct   3780
ctgtggccag ccagagcatc attgcctaca caatgtctct gggcgccgag aacagcgtgg   3840
cctactccaa caactctatc gctatcccca ccaacttcac catcagcgtg accacagaga   3900
tcctgcctgt gtccatgacc aagaccagcg tggactgcac catgtacatc tgcggcgatt   3960
ccaccgagtg ctccaacctg ctgctgcagt acggcagctt ctgcacccag ctgaatagag   4020
ccctgacagg gatcgccgtg gaacaggaca agaacaccca agaggtgttc gcccaagtga   4080
agcagatcta caagaccccc ctatcaagg acttcggcgg cttcaatttc agccagattc   4140
tgcccgatcc tagcaagccc agcaagcgga gcttcatcga ggacctgctg ttcaacaaag   4200
tgacactggc cgacgccggc ttcatcaagc agtatggcga ttgtctgggc gacattgccg   4260
ccagggatct gatttgcgcc cagaagtttar acggactgac agtgctgcct cctctgctga   4320
ccgatgagat gatcgcccag tacacatctg ccctgctggc cggcacaatc acaagcggct   4380
```

-continued

```
ggacatttgg agctggcgcc gctctgcaga tcccctttgc tatgcagatg gcctaccggt      4440
tcaacggcat cggagtgacc cagaatgtgc tgtacgagaa ccagaagctg atcgccaacc      4500
agttcaacag cgccatcggc aagatccagg acagcctgag cagcacagca agcgccctgg      4560
gaaagctgca ggacgtggtc aaccagaatg cccaggcact gaacaccctg gtcaagcagc      4620
tgtcctccaa cttcggcgcc atcagctctg tgctgaacga tatcctgagc agactggacc      4680
ctcctgaagc cgaggtgcag atcgacagac tgatcaccgg aaggctgcag tccctgcaga      4740
cctacgttac ccagcagctg atcagagccg ccgagattag agcctctgcc aatctggccg      4800
ccaccaagat gtctgagtgt gtgctgggcc agagcaagag agtggacttt tgcggcaagg      4860
gctaccacct gatgagcttc cctcagtctg cccctcacgg cgtggtgttt ctgcacgtga      4920
catacgtgcc cgctcaagag aagaatttca ccaccgctcc agccatctgc cacgacggca      4980
aagcccactt tcctagagaa ggcgtgttcg tgtccaacgg cacccattgg ttcgtgaccc      5040
agcggaactt ctacgagccc cagatcatca ccaccgacaa caccttcgtg tctggcaact      5100
gcgacgtcgt gatcggcatt gtgaacaata ccgtgtacga ccctctgcag cccgagctgg      5160
acagcttcaa agaggaactg gataagtact ttaagaacca cacaagcccc gacgtggacc      5220
tgggcgatat cagcggaatc aatgccacg tcgtgaacat ccagaaagag atcgaccggc      5280
tgaacgaggt ggccaagaat ctgaacgaga gcctgatcga cctgcaagaa ctggggaagt      5340
acgagcagta catcaagtgg cccagcggcc gcttggtccc acgtggctca cccggatctg      5400
gatacatccc ggaggcccct agggacggtc aagcttacgt gagaaaggac ggcgaatggg      5460
ttctgctgtc gaccttcttg ggacatcatc atcatcatca ctaatgaaat tcgagctcgc      5520
ggccgcatcg atcttaagtc gcgactcgag ctagcagatc tttttccctc tgccaaaaat      5580 tatgggggaca tcatgaagcc ccttgagcat ctgacttctg gctaataaag gaaatttatt      5640
ttcattgcaa tagtgtgttg gaatttttttg tgtctctcac tcggaaggac atatgggagg      5700
gcaaatcatt taaaacatca gaatgagtat ttggtttaga gtttggcaac atatgcccat      5760
atgctggctg ccatgaacaa aggttggcta taaagaggtc atcagtatat gaaacagccc      5820
cctgctgtcc attccttatt ccatagaaaa gccttgactt gaggttagat ttttttttata      5880 ttttgtttg tgttattttt ttctttaaca tccctaaaat tttccttaca tgttttacta      5940
gccagatttt tcctcctctc ctgactactc ccagtcatag ctgtccctct tctcttatgg      6000
agatccctcg acctgcagcc caagcttggc gtaatcatgg tcatagctgt ttcctgtgtg      6060
aaattgttat ccgctcacaa ttccacacaa catacgagcc ggaagcataa agtgtaaagc      6120
ctggggtgcc taatgagtga gctaactcac attaattgcg ttgcgctcac tgcccgcttt      6180
ccagtcggga aacctgtcgt gccagcggat ccgcatctca attagtcagc aaccatagtc      6240
ccgcccctaa ctccgcccat cccgccccta actccgccca gttccgccca ttctccgccc      6300
catggctgac taattttttt tatttatgca gaggccgagg ccgcctcggc ctctgagcta      6360
ttccagaagt agtgaggagg cttttttgga ggcctaggct tttgcaaaaa gctaacttgt      6420
ttattgcagc ttataatggt tacaaataaa gcaatagcat cacaaatttc acaaataaag      6480 cattttttttc actgcattct agttgtggtt tgtccaaact catcaatgta tcttatcatg      6540
tctggatccg ctgcattaat gaatcggcca acgcgcgggg agaggcggtt tgcgtattgg      6600
gcgctcttcc gcttcctcgc tcactgactc gctgcgctcg gtcgttcggc tgcggcgagc      6660
ggtatcagct cactcaaagg cggtaatacg gttatccaca gaatcagggg ataacgcagg      6720
aaagaacatg tgagcaaaag gccagcaaaa ggccaggaac cgtaaaaagg ccgcgttgct      6780
```

-continued

```
ggcgttttc cataggctcc gcccccctga cgagcatcac aaaaatcgac gctcaagtca      6840
gaggtggcga aacccgacag gactataaag ataccaggcg tttccccctg gaagctccct      6900
cgtgcgctct cctgttccga ccctgccgct taccggatac ctgtccgcct ttctcccttc      6960
gggaagcgtg gcgctttctc atagctcacg ctgtaggtat ctcagttcgg tgtaggtcgt      7020
tcgctccaag ctgggctgtg tgcacgaacc ccccgttcag cccgaccgct gcgccttatc      7080
cggtaactat cgtcttgagt ccaacccggt aagacacgac ttatcgccac tggcagcagc      7140
cactggtaac aggattagca gagcgaggta tgtaggcggt gctacagagt tcttgaagtg      7200
gtggcctaac tacggctaca ctagaagaac agtatttggt atctgcgctc tgctgaagcc      7260
agttaccttc ggaaaaagag ttggtagctc ttgatccggc aaacaaacca ccgctggtag      7320
cggtggtttt tttgtttgca agcagcagat tacgcgcaga aaaaaaggat ctcaagaaga      7380
tcctttgatc ttttctacgg ggtctgacgc tcagtggaac gaaaactcac gttaagggat      7440
tttggtcatg agattatcaa aaaggatctt cacctagatc cttttaaatt aaaaatgaag      7500
ttttaaatca atctaaagta tatatgagta aacttggtct gacagttacc aatgcttaat      7560
cagtgaggca cctatctcag cgatctgtct atttcgttca tccatagttg cctgactccc      7620
cgtcgtgtag ataactacga tacgggaggg cttaccatct ggccccagtg ctgcaatgat      7680
accgcgagac ccacgctcac cggctccaga tttatcagca ataaaccagc cagccggaag      7740
ggccgagcgc agaagtggtc ctgcaacttt atccgcctcc atccagtcta ttaattgttg      7800
ccgggaagct agagtaagta gttcgccagt taatagtttg cgcaacgttg ttgccattgc      7860
tacaggcatc gtggtgtcac gctcgtcgtt tggtatggct tcattcagct ccggttccca      7920
acgatcaagg cgagttacat gatcccccat gttgtgcaaa aaagcggtta gctccttcgg      7980
tcctccgatc gttgtcagaa gtaagttggc cgcagtgtta tcactcatgg ttatggcagc      8040
actgcataat tctcttactg tcatgccatc cgtaagatgc ttttctgtga ctggtgagta      8100
ctcaaccaag tcattctgag aatagtgtat gcggcgaccg agttgctctt gcccggcgtc      8160
aatacgggat aataccgcgc cacatagcag aactttaaaa gtgctcatca ttggaaaacg      8220
ttcttcgggg cgaaaactct caaggatctt accgctgttg agatccagtt cgatgtaacc      8280
cactcgtgca cccaactgat cttcagcatc ttttactttc accagcgttt ctgggtgagc      8340
aaaaacagga aggcaaaatg ccgcaaaaaa gggaataagg gcgacacgga aatgttgaat      8400
actcatactc ttcctttttc aatattattg aagcatttat cagggttatt gtctcatgag      8460
cggatacata tttgaatgta tttagaaaaa taaacaaata ggggttccgc gcacatttcc      8520
ccgaaaagtg ccacctg                                                    8537
```

```
<210> SEQ ID NO 2
<211> LENGTH: 1284
<212> TYPE: PRT
<213> ORGANISM: Artificial Sequence
<220> FEATURE:
<223> OTHER INFORMATION: Synthetic

<400> SEQUENCE: 2

Met Phe Met Pro Ser Ser Phe Ser Tyr Ser Ser Trp Ala Thr Cys Trp
1               5                   10                  15

Leu Leu Cys Cys Leu Ile Ile Leu Ala Lys Ala Thr Met Phe Val Phe
            20                  25                  30

Leu Val Leu Leu Pro Leu Val Ser Ser Gln Cys Val Asn Leu Thr Thr
        35                  40                  45
```

-continued

```
Arg Thr Gln Leu Pro Pro Ala Tyr Thr Asn Ser Phe Thr Arg Gly Val
    50                  55                  60

Tyr Tyr Pro Asp Lys Val Phe Arg Ser Ser Val Leu His Ser Thr Gln
65                  70                  75                  80

Asp Leu Phe Leu Pro Phe Phe Ser Asn Val Thr Trp Phe His Ala Ile
                85                  90                  95

His Val Ser Gly Thr Asn Gly Thr Lys Arg Phe Asp Asn Pro Val Leu
                100                 105                 110

Pro Phe Asn Asp Gly Val Tyr Phe Ala Ser Thr Glu Lys Ser Asn Ile
                115                 120                 125

Ile Arg Gly Trp Ile Phe Gly Thr Thr Leu Asp Ser Lys Thr Gln Ser
    130                 135                 140

Leu Leu Ile Val Asn Asn Ala Thr Asn Val Val Ile Lys Val Cys Glu
145                 150                 155                 160

Phe Gln Phe Cys Asn Asp Pro Phe Leu Gly Val Tyr Tyr His Lys Asn
                165                 170                 175

Asn Lys Ser Trp Met Glu Ser Glu Phe Arg Val Tyr Ser Ser Ala Asn
                180                 185                 190

Asn Cys Thr Phe Glu Tyr Val Ser Gln Pro Phe Leu Met Asp Leu Glu
                195                 200                 205

Gly Lys Gln Gly Asn Phe Lys Asn Leu Arg Glu Phe Val Phe Lys Asn
    210                 215                 220

Ile Asp Gly Tyr Phe Lys Ile Tyr Ser Lys His Thr Pro Ile Asn Leu
225                 230                 235                 240

Val Arg Asp Leu Pro Gln Gly Phe Ser Ala Leu Glu Pro Leu Val Asp
                245                 250                 255

Leu Pro Ile Gly Ile Asn Ile Thr Arg Phe Gln Thr Leu Leu Ala Leu
                260                 265                 270

His Arg Ser Tyr Leu Thr Pro Gly Asp Ser Ser Ser Gly Trp Thr Ala
    275                 280                 285

Gly Ala Ala Ala Tyr Tyr Val Gly Tyr Leu Gln Pro Arg Thr Phe Leu
    290                 295                 300

Leu Lys Tyr Asn Glu Asn Gly Thr Ile Thr Asp Ala Val Asp Cys Ala
305                 310                 315                 320

Leu Asp Pro Leu Ser Glu Thr Lys Cys Thr Leu Lys Ser Phe Thr Val
                325                 330                 335

Glu Lys Gly Ile Tyr Gln Thr Ser Asn Phe Arg Val Gln Pro Thr Glu
                340                 345                 350

Ser Ile Val Arg Phe Pro Asn Ile Thr Asn Leu Cys Pro Phe Gly Glu
                355                 360                 365

Val Phe Asn Ala Thr Arg Phe Ala Ser Val Tyr Ala Trp Asn Arg Lys
    370                 375                 380

Arg Ile Ser Asn Cys Val Ala Asp Tyr Ser Val Leu Tyr Asn Ser Ala
385                 390                 395                 400

Ser Phe Ser Thr Phe Lys Cys Tyr Gly Val Ser Pro Thr Lys Leu Asn
                405                 410                 415

Asp Leu Cys Phe Thr Asn Val Tyr Ala Asp Ser Phe Val Ile Arg Gly
                420                 425                 430

Asp Glu Val Arg Gln Ile Ala Pro Gly Gln Thr Gly Lys Ile Ala Asp
                435                 440                 445

Tyr Asn Tyr Lys Leu Pro Asp Asp Phe Thr Gly Cys Val Ile Ala Trp
    450                 455                 460
```

```
Asn Ser Asn Asn Leu Asp Ser Lys Val Gly Gly Asn Tyr Asn Tyr Leu
465             470             475             480

Tyr Arg Leu Phe Arg Lys Ser Asn Leu Lys Pro Phe Glu Arg Asp Ile
            485             490             495

Ser Thr Glu Ile Tyr Gln Ala Gly Ser Thr Pro Cys Asn Gly Val Glu
            500             505             510

Gly Phe Asn Cys Tyr Phe Pro Leu Gln Ser Tyr Gly Phe Gln Pro Thr
            515             520             525

Asn Gly Val Gly Tyr Gln Pro Tyr Arg Val Val Leu Ser Phe Glu
            530             535             540

Leu Leu His Ala Pro Ala Thr Val Cys Gly Pro Lys Lys Ser Thr Asn
545             550             555             560

Leu Val Lys Asn Lys Cys Val Asn Phe Asn Phe Asn Gly Leu Thr Gly
                565             570             575

Thr Gly Val Leu Thr Glu Ser Asn Lys Lys Phe Leu Pro Phe Gln Gln
            580             585             590

Phe Gly Arg Asp Ile Ala Asp Thr Thr Asp Ala Val Arg Asp Pro Gln
            595             600             605

Thr Leu Glu Ile Leu Asp Ile Thr Pro Cys Ser Phe Gly Gly Val Ser
            610             615             620

Val Ile Thr Pro Gly Thr Asn Thr Ser Asn Gln Val Ala Val Leu Tyr
625             630             635             640

Gln Asp Val Asn Cys Thr Glu Val Pro Val Ala Ile His Ala Asp Gln
                645             650             655

Leu Thr Pro Thr Trp Arg Val Tyr Ser Thr Gly Ser Asn Val Phe Gln
            660             665             670

Thr Arg Ala Gly Cys Leu Ile Gly Ala Glu His Val Asn Asn Ser Tyr
            675             680             685

Glu Cys Asp Ile Pro Ile Gly Ala Gly Ile Cys Ala Ser Tyr Gln Thr
            690             695             700

Gln Thr Asn Ser Pro Ala Ser Val Ala Ser Gln Ser Ile Ile Ala Tyr
705             710             715             720

Thr Met Ser Leu Gly Ala Glu Asn Ser Val Ala Tyr Ser Asn Asn Ser
                725             730             735

Ile Ala Ile Pro Thr Asn Phe Thr Ile Ser Val Thr Thr Glu Ile Leu
            740             745             750

Pro Val Ser Met Thr Lys Thr Ser Val Asp Cys Thr Met Tyr Ile Cys
            755             760             765

Gly Asp Ser Thr Glu Cys Ser Asn Leu Leu Leu Gln Tyr Gly Ser Phe
            770             775             780

Cys Thr Gln Leu Asn Arg Ala Leu Thr Gly Ile Ala Val Glu Gln Asp
785             790             795             800

Lys Asn Thr Gln Glu Val Phe Ala Gln Val Lys Gln Ile Tyr Lys Thr
                805             810             815

Pro Pro Ile Lys Asp Phe Gly Gly Phe Asn Phe Ser Gln Ile Leu Pro
            820             825             830

Asp Pro Ser Lys Pro Ser Lys Arg Ser Phe Ile Glu Asp Leu Leu Phe
            835             840             845

Asn Lys Val Thr Leu Ala Asp Ala Gly Phe Ile Lys Gln Tyr Gly Asp
    850             855             860

Cys Leu Gly Asp Ile Ala Ala Arg Asp Leu Ile Cys Ala Gln Lys Phe
865             870             875             880

Asn Gly Leu Thr Val Leu Pro Pro Leu Leu Thr Asp Glu Met Ile Ala
```

-continued

```
                    885                 890                 895
    Gln Tyr Thr Ser Ala Leu Leu Ala Gly Thr Ile Thr Ser Gly Trp Thr
                     900                 905                 910

Phe Gly Ala Gly Ala Ala Leu Gln Ile Pro Phe Ala Met Gln Met Ala
                     915                 920                 925

Tyr Arg Phe Asn Gly Ile Gly Val Thr Gln Asn Val Leu Tyr Glu Asn
          930                 935                 940

Gln Lys Leu Ile Ala Asn Gln Phe Asn Ser Ala Ile Gly Lys Ile Gln
    945                 950                 955                 960

Asp Ser Leu Ser Ser Thr Ala Ser Ala Leu Gly Lys Leu Gln Asp Val
                     965                 970                 975

Val Asn Gln Asn Ala Gln Ala Leu Asn Thr Leu Val Lys Gln Leu Ser
                     980                 985                 990

Ser Asn Phe Gly Ala Ile Ser Ser  Val Leu Asn Asp Ile  Leu Ser Arg
                     995                 1000                 1005

Leu Asp  Pro Pro Glu Ala Glu  Val Gln Ile Asp Arg  Leu Ile Thr
         1010                 1015                 1020

Gly Arg  Leu Gln Ser Leu Gln  Thr Tyr Val Thr Gln  Gln Leu Ile
         1025                 1030                 1035

Arg Ala  Ala Glu Ile Arg Ala  Ser Ala Asn Leu Ala  Ala Thr Lys
         1040                 1045                 1050

Met Ser  Glu Cys Val Leu Gly  Gln Ser Lys Arg Val  Asp Phe Cys
         1055                 1060                 1065

Gly Lys  Gly Tyr His Leu Met  Ser Phe Pro Gln Ser  Ala Pro His
         1070                 1075                 1080

Gly Val  Val Phe Leu His Val  Thr Tyr Val Pro Ala  Gln Glu Lys
         1085                 1090                 1095

Asn Phe  Thr Thr Ala Pro Ala  Ile Cys His Asp Gly  Lys Ala His
         1100                 1105                 1110

Phe Pro  Arg Glu Gly Val Phe  Val Ser Asn Gly Thr  His Trp Phe
         1115                 1120                 1125

Val Thr  Gln Arg Asn Phe Tyr  Glu Pro Gln Ile Ile  Thr Thr Asp
         1130                 1135                 1140

Asn Thr  Phe Val Ser Gly Asn  Cys Asp Val Val Ile  Gly Ile Val
         1145                 1150                 1155

Asn Asn  Thr Val Tyr Asp Pro  Leu Gln Pro Glu Leu  Asp Ser Phe
         1160                 1165                 1170

Lys Glu  Glu Leu Asp Lys Tyr  Phe Lys Asn His Thr  Ser Pro Asp
         1175                 1180                 1185

Val Asp  Leu Gly Asp Ile Ser  Gly Ile Asn Ala Ser  Val Val Asn
         1190                 1195                 1200

Ile Gln  Lys Glu Ile Asp Arg  Leu Asn Glu Val Ala  Lys Asn Leu
         1205                 1210                 1215

Asn Glu  Ser Leu Ile Asp Leu  Gln Glu Leu Gly Lys  Tyr Glu Gln
         1220                 1225                 1230

Tyr Ile  Lys Trp Pro Ser Gly  Arg Leu Val Pro Arg  Gly Ser Pro
         1235                 1240                 1245

Gly Ser  Gly Tyr Ile Pro Glu  Ala Pro Arg Asp Gly  Gln Ala Tyr
         1250                 1255                 1260

Val Arg  Lys Asp Gly Glu Trp  Val Leu Leu Ser Thr  Phe Leu Gly
         1265                 1270                 1275

His His  His His His His
         1280
```

-continued

```
<210> SEQ ID NO 3
<211> LENGTH: 5501
<212> TYPE: DNA
<213> ORGANISM: Artificial Sequence
<220> FEATURE:
<223> OTHER INFORMATION: Synthetic

<400> SEQUENCE: 3
rbdgtcgaca ttgattattg actagttatt aatagtaatc aattacgggg tcattagttc      60
atagcccata tatggagttc cgcgttacat aacttacggt aaatggcccg cctggctgac     120
cgcccaacga cccccgccca ttgacgtcaa taatgacgta tgttcccata gtaacgccaa     180
tagggacttt ccattgacgt caatgggtgg agtatttacg gtaaactgcc cacttggcag     240
tacatcaagt gtatcatatg ccaagtacgc cccctattga cgtcaatgac ggtaaatggc     300
ccgcctggca ttatgcccag tacatgacct tatgggactt cctacttgg cagtacatct      360 acgtattagt catcgctatt accatggtcg aggtgagccc cacgttctgc ttcactctcc     420
ccatctcccc cccctcccca cccccaattt tgtatttatt tattttttaa ttattttgtg     480
cagcgatggg ggcggggggg ggggggcgc gcgccaggcg gggcggggcg gggcgagggg      540
cggggcgggg cgaggcggag aggtgcggcg gcagccaatc agagcggcgc gctccgaaag     600
tttcctttta tggcgaggcg gcggcggcgg cggccctata aaaagcgaag cgcgcggcgg     660
gcgggagtcg ctgcgcgcgc tgccttcgcc ccgtgccccg ctccgcgccg cctcgcgccg     720
cccgccccgg ctctgactga ccgcgttact cccacaggtg agcgggcggg acggcccttc     780
tcctccgggc tgtaattagc gcttggttta atgacggctt gtttcttttc tgtggctgcg     840
tgaaagcctt gaggggctcc gggagggccc tttgtgcggg gggagcggc tcggggggtg      900 cgtgcgtgtg tgtgtgcgtg gggagcgccg cgtgcggctc cgcgctgccc ggcggctgtg     960
agcgctgcgg gcgcgcgcg gggctttgtg cgctccgcag tgtgcgcgag gggagcgcgg    1020 ccggggggcgg tgccccgcgg tgcgggggggg gctgcgaggg aacaaaggc tgcgtgcggg    1080 gtgtgtgcgt ggggggggtga gcaggggggtg tgggcgcgtc ggtcgggctg caacccccc    1140 ctgcacccc ctccccgagt tgctgagcac ggcccggctt cgggtgcggg gctccgtacg    1200
gggcgtggcg cggggctcgc cgtgccgggc ggggggtggc ggcaggtggg ggtgccgggc    1260
ggggcggggc cgcctcgggc cggggagggc tcggggagg ggcgcggcgg cccccggagc    1320
gccggcggct gtcgaggcgc ggcgagccgc agccattgcc ttttatggta atcgtgcgag    1380
agggcgcagg gacttccttt gtcccaaatc tggcggagcc gaaatctggg aggcgccgcc    1440 gcacccctc tagcgggcgc ggggcgaagc ggtgcggcgc cggcaggaag gaaatgggcg    1500
gggagggcct tcgtgcgtcg ccgcgccgcc gtcccttct ccctctccag cctcggggct    1560
gccgcggggg gacggctgcc ttcggggggg acggggcagg gcggggttcg gcttctggcg    1620
tgtgaccggc ggctctagag cctctgctaa ccatgttcat gccttcttct tttcctaca    1680 gctcctgggc aacgtgctgg ttattgtgct gtctcatcat tttggcaaag gccaccatgt    1740
tcgtgtttct ggtgctgctg cctctggtgt ccagccagcg ggtgcagccc accgaatcca    1800
tcgtgcggtt ccccaatatc accaatctgt gcccccttcgg cgaggtgttc aatgccacca    1860
gattcgcctc tgtgtacgcc tggaaccgga agcggatcag caattgcgtg gccgactact    1920
ccgtgctgta caactccgcc agcttcagca ccttcaagtg ctacggcgtg tcccctacca    1980
agctgaacga cctgtgcttc acaaacgtgt acgccgacag cttcgtgatc cggggagatg    2040
```

-continued

```
aagtgcggca gattgcccct ggacagacag gcaagatcgc cgactacaac tacaagctgc    2100
ccgacgactt caccggctgt gtgattgcct ggaacagcaa caacctggac tccaaagtcg    2160
gcggcaacta caattacctg taccggctgt tccggaagtc caatctgaag cccttcgagc    2220
gggacatctc caccgagatc tatcaggccg gcagcacccc ttgtaacggc gtggaaggct    2280
tcaactgcta cttcccactg cagtcctacg gctttcagcc cacaaatggc gtgggctatc    2340
agccctacag agtggtggtg ctgagcttcg aactgctgca tgcccctgcc acagtgtgcg    2400
gccctaagaa aagcaccaat ctcgtgaaga acaaatgcgt gaacttccac catcaccatc    2460
accattgata aaattcgagc tcgcggccgc atcgatctta agtcgcgact cgagctagca    2520
gatctttttc cctctgccaa aaattatggg gacatcatga gccccttga gcatctgact    2580 tctggctaat aaaggaaatt tattttcatt gcaatagtgt gttggaattt tttgtgtctc    2640
tcactcggaa ggacatatgg gagggcaaat catttaaaac atcagaatga gtatttggtt    2700
tagagtttgg caacatatgc ccatatgctg gctgccatga acaaaggttg gctataaaga    2760
ggtcatcagt atatgaaaca gcccctgct gtccattcct tattccatag aaaagccttg    2820
acttgaggtt agattttttt tatattttgt tttgtgttat tttttctttt aacatcccta    2880
aaattttcct tacatgtttt actagccaga ttttcctcc tctcctgact actcccagtc    2940
atagctgtcc ctcttctctt atggagatcc ctcgacctgc agcccaagct tggcgtaatc    3000
atggtcatag ctgtttcctg tgtgaaattg ttatccgctc acaattccac acaacatacg    3060
agccggaagc ataaagtgta aagcctgggg tgcctaatga gtgagctaac tcacattaat    3120
tgcgttgcgc tcactgcccg ctttccagtc gggaaacctg tcgtgccagc ggatccgcat    3180
ctcaattagt cagcaaccat agtcccgccc ctaactccgc ccatcccgcc cctaactccg    3240
cccagttccg cccattctcc gccccatggc tgactaattt tttttattta tgcagaggcc    3300
gaggccgcct cggcctctga gctattccag aagtagtgag gaggcttttt tggaggccta    3360
ggcttttgca aaaagctaac ttgtttattg cagcttataa tggttacaaa taaagcaata    3420
gcatcacaaa tttcacaaat aaagcatttt tttcactgca ttctagttgt ggtttgtcca    3480
aactcatcaa tgtatcttat catgtctgga tccgctgcat taatgaatcg gccaacgcgc    3540
ggggagaggc ggtttgcgta ttgggcgctc ttccgcttcc tcgctcactg actcgctgcg    3600
ctcggtcgtt cggctgcggc gagcggtatc agctcactca aaggcggtaa tacggttatc    3660
cacagaatca ggggataacg caggaaagaa catgtgagca aaaggccagc aaaaggccag    3720
gaaccgtaaa aaggccgcgt tgctggcgtt tttccatagg ctccgccccc ctgacgagca    3780
tcacaaaaat cgacgctcaa gtcagaggtg gcgaaacccg acaggactat aaagatacca    3840
ggcgtttccc cctggaagct ccctcgtgcg ctctcctgtt ccgaccctgc cgcttaccgg    3900
atacctgtcc gcctttctcc cttcgggaag cgtggcgctt tctcatagct cacgctgtag    3960
gtatctcagt tcggtgtagg tcgttcgctc caagctgggc tgtgtgcacg aaccccccgt    4020
tcagcccgac cgctgcgcct tatccggtaa ctatcgtctt gagtccaacc cggtaagaca    4080
cgacttatcg ccactggcag cagccactgg taacaggatt agcagagcga ggtatgtagg    4140
cggtgctaca gagttcttga agtggtggcc taactacggc tacactagaa gaacagtatt    4200
tggtatctgc gctctgctga agccagttac cttcggaaaa agagttggta gctcttgatc    4260
cggcaaacaa accaccgctg gtagcggtgg tttttttgtt tgcaagcagc agattacgcg    4320
cagaaaaaaa ggatctcaag aagatccttt gatcttttct acggggtctg acgctcagtg    4380
gaacgaaaac tcacgttaag ggattttggt catgagatta tcaaaaagga tcttcaccta    4440
```

-continued

```
gatccttta aattaaaaat gaagttttaa atcaatctaa agtatatatg agtaaacttg    4500
gtctgacagt taccaatgct taatcagtga ggcacctatc tcagcgatct gtctatttcg    4560
ttcatccata gttgcctgac tccccgtcgt gtagataact acgatacggg agggcttacc    4620
atctggcccc agtgctgcaa tgataccgcg agacccacgc tcaccggctc cagatttatc    4680
agcaataaac cagccagccg gaagggccga gcgcagaagt ggtcctgcaa ctttatccgc    4740
ctccatccag tctattaatt gttgccggga agctagagta agtagttcgc cagttaatag    4800
tttgcgcaac gttgttgcca ttgctacagg catcgtggtg tcacgctcgt cgtttggtat    4860
ggcttcattc agctccggtt cccaacgatc aaggcgagtt acatgatccc ccatgttgtg    4920
caaaaaagcg gttagctcct tcggtcctcc gatcgttgtc agaagtaagt tggccgcagt    4980
gttatcactc atggttatgg cagcactgca taattctctt actgtcatgc catccgtaag    5040
atgcttttct gtgactggtg agtactcaac caagtcattc tgagaatagt gtatgcggcg    5100
accgagttgc tcttgcccgg cgtcaatacg ggataatacc gcgccacata gcagaacttt    5160
aaaagtgctc atcattggaa aacgttcttc ggggcgaaaa ctctcaagga tcttaccgct    5220
gttgagatcc agttcgatgt aacccactcg tgcacccaac tgatcttcag catcttttac    5280
tttcaccagc gtttctgggt gagcaaaaac aggaaggcaa aatgccgcaa aaaagggaat    5340
aagggcgaca cggaaatgtt gaatactcat actcttcctt tttcaatatt attgaagcat    5400
ttatcagggt tattgtctca tgagcggata catatttgaa tgtatttaga aaaataaaca    5460
aataggggtt ccgcgcacat ttccccgaaa agtgccacct g                        5501
```

<210> SEQ ID NO 4
<211> LENGTH: 271
<212> TYPE: PRT
<213> ORGANISM: Artificial Sequence
<220> FEATURE:
<223> OTHER INFORMATION: Synthetic

<400> SEQUENCE: 4

```
Met Phe Met Pro Ser Ser Phe Ser Tyr Ser Ser Trp Ala Thr Cys Trp
1               5                   10                  15

Leu Leu Cys Cys Leu Ile Ile Leu Ala Lys Ala Thr Met Phe Val Phe
            20                  25                  30

Leu Val Leu Leu Pro Leu Val Ser Ser Gln Arg Val Gln Pro Thr Glu
        35                  40                  45

Ser Ile Val Arg Phe Pro Asn Ile Thr Asn Leu Cys Pro Phe Gly Glu
    50                  55                  60

Val Phe Asn Ala Thr Arg Phe Ala Ser Val Tyr Ala Trp Asn Arg Lys
65                  70                  75                  80

Arg Ile Ser Asn Cys Val Ala Asp Tyr Ser Val Leu Tyr Asn Ser Ala
                85                  90                  95

Ser Phe Ser Thr Phe Lys Cys Tyr Gly Val Ser Pro Thr Lys Leu Asn
            100                 105                 110

Asp Leu Cys Phe Thr Asn Val Tyr Ala Asp Ser Phe Val Ile Arg Gly
        115                 120                 125

Asp Glu Val Arg Gln Ile Ala Pro Gly Gln Thr Gly Lys Ile Ala Asp
        130                 135                 140

Tyr Asn Tyr Lys Leu Pro Asp Asp Phe Thr Gly Cys Val Ile Ala Trp
145                 150                 155                 160

Asn Ser Asn Asn Leu Asp Ser Lys Val Gly Gly Asn Tyr Asn Tyr Leu
                165                 170                 175
```

```
Tyr Arg Leu Phe Arg Lys Ser Asn Leu Lys Pro Phe Glu Arg Asp Ile
            180                 185                 190

Ser Thr Glu Ile Tyr Gln Ala Gly Ser Thr Pro Cys Asn Gly Val Glu
            195                 200                 205

Gly Phe Asn Cys Tyr Phe Pro Leu Gln Ser Tyr Gly Phe Gln Pro Thr
        210                 215                 220

Asn Gly Val Gly Tyr Gln Pro Tyr Arg Val Val Val Leu Ser Phe Glu
225                 230                 235                 240

Leu Leu His Ala Pro Ala Thr Val Cys Gly Pro Lys Lys Ser Thr Asn
                245                 250                 255

Leu Val Lys Asn Lys Cys Val Asn Phe His His His His His His
            260                 265                 270

<210> SEQ ID NO 5
<211> LENGTH: 691
<212> TYPE: PRT
<213> ORGANISM: Artificial Sequence
<220> FEATURE:
<223> OTHER INFORMATION: Synthetic

<400> SEQUENCE: 5

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
        210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270
```

-continued

```
Thr Asp Ala Val Asp Cys Ala Leu Asp Pro Leu Ser Glu Thr Lys Cys
    275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
    355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
                595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg His His
                660                 665                 670

His His His His Gly Leu Asn Asp Ile Phe Glu Ala Gln Lys Ile Glu
    675                 680                 685
```

-continued

```
Trp His Glu
    690

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Lys Arg Ser Phe Ile Glu Asp Leu Leu Phe Asn Lys Val
1               5                   10

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
tcgtcgtttt gtcgttttgt cgtt                                                           24

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
tgactgtgaa cgttcgagat ga                                                             22

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tccatgacgt tcctgacgtt                                                                20

<210> SEQ ID NO 10
<211> LENGTH: 229
<212> TYPE: PRT
<213> ORGANISM: Artificial Sequence
<220> FEATURE:
<223> OTHER INFORMATION: Synthetic

<400> SEQUENCE: 10

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95
```

```
Thr Gly Lys Ile Ala Asp Tyr Asn Tyr Lys Leu Pro Asp Asp Phe Thr
        100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
            165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe His
    210                 215                 220

His His His His His
225
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: 18-O-Dimethoxytritylhexaethyleneglycol,1-[(2-
      cyanoethyl)-(N,N-diisopropyl)]-phosphoramidite (Spacer18)
<220> FEATURE:
<221> NAME/KEY: misc_feature
<222> LOCATION: (20)..(20)
<223> OTHER INFORMATION: 18-O-Dimethoxytritylhexaethyleneglycol,1-[(2-
      cyanoethyl)-(N,N-diisopropyl)]-phosphoramidite (Spacer18)
<220> FEATURE:
<221> NAME/KEY: misc_feature
<222> LOCATION: (20)..(20)
<223> OTHER INFORMATION: Cholesterol

<400> SEQUENCE: 11
tccatgacgt tcctgacgtt                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: 1-[3-(4-monomethoxytrityloxy)propyl]-1'-[3-[(2-
      cyanoethyl)-(N,N-diisopropylphosphoramidityl]propyl]-3,3,3',3'-
      tetramethylindodicarbocyanine chloride (Cy5)
<220> FEATURE:
<221> NAME/KEY: misc_feature
<222> LOCATION: (20)..(20)
<223> OTHER INFORMATION: 18-O-Dimethoxytritylhexaethyleneglycol,1-[(2-
      cyanoethyl)-(N,N-diisopropyl)]-phosphoramidite (Spacer18)
<220> FEATURE:
<221> NAME/KEY: misc_feature
<222> LOCATION: (20)..(20)
<223> OTHER INFORMATION: 18-O-Dimethoxytritylhexaethyleneglycol,1-[(2-
      cyanoethyl)-(N,N-diisopropyl)]-phosphoramidite (Spacer18)
<220> FEATURE:
<221> NAME/KEY: misc_feature
```

-continued

```
<222> LOCATION: (20)..(20)
<223> OTHER INFORMATION: Cholesterol

<400> SEQUENCE: 12
tccatgacgt tcctgacgtt                                                    20

<210> SEQ ID NO 13
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 18-O-Dimethoxytritylhexaethyleneglycol,1-[(2-
      cyanoethyl)-(N,N-diisopropyl)]-phosphoramidite (Spacer18)
<220> FEATURE:
<221> NAME/KEY: misc_feature
<222> LOCATION: (24)..(24)
<223> OTHER INFORMATION: 18-O-Dimethoxytritylhexaethyleneglycol,1-[(2-
      cyanoethyl)-(N,N-diisopropyl)]-phosphoramidite (Spacer18)
<220> FEATURE:
<221> NAME/KEY: misc_feature
<222> LOCATION: (24)..(24)
<223> OTHER INFORMATION: Cholesterol

<400> SEQUENCE: 13
tcgtcgtttt gtcgttttgt cgtt                                               24

<210> SEQ ID NO 14
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: SARS-CoV-2 surface glycoprotein

<400> SEQUENCE: 14

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

-continued

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
            210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
```

-continued

```
            595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020
```

-continued

```
Leu Ala  Ala Thr Lys Met Ser  Glu Cys Val Leu Gly  Gln Ser Lys
    1025             1030              1035

Arg Val  Asp Phe Cys Gly Lys  Gly Tyr His Leu Met  Ser Phe Pro
    1040             1045              1050

Gln Ser  Ala Pro His Gly Val  Val Phe Leu His Val  Thr Tyr Val
    1055             1060              1065

Pro Ala  Gln Glu Lys Asn Phe  Thr Thr Ala Pro Ala  Ile Cys His
    1070             1075              1080

Asp Gly  Lys Ala His Phe Pro  Arg Glu Gly Val Phe  Val Ser Asn
    1085             1090              1095

Gly Thr  His Trp Phe Val Thr  Gln Arg Asn Phe Tyr  Glu Pro Gln
    1100             1105              1110

Ile Ile  Thr Thr Asp Asn Thr  Phe Val Ser Gly Asn  Cys Asp Val
    1115             1120              1125

Val Ile  Gly Ile Val Asn Asn  Thr Val Tyr Asp Pro  Leu Gln Pro
    1130             1135              1140

Glu Leu  Asp Ser Phe Lys Glu  Glu Leu Asp Lys Tyr  Phe Lys Asn
    1145             1150              1155

His Thr  Ser Pro Asp Val Asp  Leu Gly Asp Ile Ser  Gly Ile Asn
    1160             1165              1170

Ala Ser  Val Val Asn Ile Gln  Lys Glu Ile Asp Arg  Leu Asn Glu
    1175             1180              1185

Val Ala  Lys Asn Leu Asn Glu  Ser Leu Ile Asp Leu  Gln Glu Leu
    1190             1195              1200

Gly Lys  Tyr Glu Gln Tyr Ile  Lys Trp Pro Trp Tyr  Ile Trp Leu
    1205             1210              1215

Gly Phe  Ile Ala Gly Leu Ile  Ala Ile Val Met Val  Thr Ile Met
    1220             1225              1230

Leu Cys  Cys Met Thr Ser Cys  Cys Ser Cys Leu Lys  Gly Cys Cys
    1235             1240              1245

Ser Cys  Gly Ser Cys Cys Lys  Phe Asp Glu Asp Asp  Ser Glu Pro
    1250             1255              1260

Val Leu  Lys Gly Val Lys Leu  His Tyr Thr
    1265             1270
```

```
<210> SEQ ID NO 15
<211> LENGTH: 223
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: SARS-CoV-2 RBD

<400> SEQUENCE: 15

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80
```

-continued

```
Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
               100                 105                 110

Gly Cys Val Ile Ala Trp Asn Ser Asn Asn Leu Asp Ser Lys Val Gly
               115                 120                 125

Gly Asn Tyr Asn Tyr Leu Tyr Arg Leu Phe Arg Lys Ser Asn Leu Lys
           130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
               165                 170                 175

Tyr Gly Phe Gln Pro Thr Asn Gly Val Gly Tyr Gln Pro Tyr Arg Val
               180                 185                 190

Val Val Leu Ser Phe Glu Leu Leu His Ala Pro Ala Thr Val Cys Gly
               195                 200                 205

Pro Lys Lys Ser Thr Asn Leu Val Lys Asn Lys Cys Val Asn Phe
           210                 215                 220
```

```
<210> SEQ ID NO 16
<211> LENGTH: 223
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: SARS-CoV-2 Omicron variant RBD

<400> SEQUENCE: 16
```

```
Arg Val Gln Pro Thr Glu Ser Ile Val Arg Phe Pro Asn Ile Thr Asn
1                   5                   10                  15

Leu Cys Pro Phe Asp Glu Val Phe Asn Ala Thr Arg Phe Ala Ser Val
               20                  25                  30

Tyr Ala Trp Asn Arg Lys Arg Ile Ser Asn Cys Val Ala Asp Tyr Ser
           35                  40                  45

Val Leu Tyr Asn Leu Ala Pro Phe Phe Thr Phe Lys Cys Tyr Gly Val
           50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Asn Ile Ala Asp Tyr Asn Tyr Lys Leu Pro Asp Asp Phe Thr
               100                 105                 110

Gly Cys Val Ile Ala Trp Asn Ser Asn Lys Leu Asp Ser Lys Val Ser
               115                 120                 125

Gly Asn Tyr Asn Tyr Leu Tyr Arg Leu Phe Arg Lys Ser Asn Leu Lys
           130                 135                 140

Pro Phe Glu Arg Asp Ile Ser Thr Glu Ile Tyr Gln Ala Gly Asn Lys
145                 150                 155                 160

Pro Cys Asn Gly Val Ala Gly Phe Asn Cys Tyr Phe Pro Leu Arg Ser
               165                 170                 175

Tyr Ser Phe Arg Pro Thr Tyr Gly Val Gly His Gln Pro Tyr Arg Val
               180                 185                 190

Val Val Leu Ser Phe Glu Leu Leu His Ala Pro Ala Thr Val Cys Gly
               195                 200                 205
```

-continued

```
Pro Lys Lys Ser Thr Asn Leu Val Lys Asn Lys Cys Val Asn Phe
    210                 215                 220

<210> SEQ ID NO 17
<211> LENGTH: 359
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: RBD

<400> SEQUENCE: 17

Val Ile Val Arg Glu Gly Ala Gly Thr Ser Phe Val Pro Asn Leu Ala
1               5                   10                  15

Glu Pro Lys Ser Gly Arg Arg Arg Thr Pro Ser Ser Gly Arg Gly
            20                  25                  30

Ala Lys Arg Cys Gly Ala Gly Arg Lys Glu Met Gly Gly Glu Gly Leu
        35                  40                  45

Arg Ala Ser Pro Arg Arg Arg Pro Leu Leu Pro Leu Gln Pro Arg Gly
    50                  55                  60

Cys Arg Gly Gly Thr Ala Ala Phe Gly Gly Asp Gly Ala Gly Arg Gly
65                  70                  75                  80

Ser Ala Ser Gly Val Pro Ala Ala Leu Glu Pro Leu Leu Thr Met Phe
                85                  90                  95

Met Pro Ser Ser Phe Ser Tyr Ser Ser Trp Ala Thr Cys Trp Leu Leu
            100                 105                 110

Cys Cys Leu Ile Ile Leu Ala Lys Ala Thr Met Phe Val Phe Leu Val
        115                 120                 125

Leu Leu Pro Leu Val Ser Ser Gln Arg Val Gln Pro Thr Glu Ser Ile
    130                 135                 140

Val Arg Phe Pro Asn Ile Thr Asn Leu Cys Pro Phe Gly Glu Val Phe
145                 150                 155                 160

Asn Ala Thr Arg Phe Ala Ser Val Tyr Ala Trp Asn Arg Lys Arg Ile
                165                 170                 175

Ser Asn Cys Val Ala Asp Tyr Ser Val Leu Tyr Asn Ser Ala Ser Phe
            180                 185                 190

Ser Thr Phe Lys Cys Tyr Gly Val Ser Pro Thr Lys Leu Asn Asp Leu
            195                 200                 205

Cys Phe Thr Asn Val Tyr Ala Asp Ser Phe Val Ile Arg Gly Asp Glu
    210                 215                 220

Val Arg Gln Ile Ala Pro Gly Gln Thr Gly Lys Ile Ala Asp Tyr Asn
225                 230                 235                 240

Tyr Lys Leu Pro Asp Asp Phe Thr Gly Cys Val Ile Ala Trp Asn Ser
                245                 250                 255

Asn Asn Leu Asp Ser Lys Val Gly Gly Asn Tyr Asn Tyr Leu Tyr Arg
            260                 265                 270

Leu Phe Arg Lys Ser Asn Leu Lys Pro Phe Glu Arg Asp Ile Ser Thr
        275                 280                 285

Glu Ile Tyr Gln Ala Gly Ser Thr Pro Cys Asn Gly Val Glu Gly Phe
    290                 295                 300

Asn Cys Tyr Phe Pro Leu Gln Ser Tyr Gly Phe Gln Pro Thr Asn Gly
305                 310                 315                 320

Val Gly Tyr Gln Pro Tyr Arg Val Val Val Leu Ser Phe Glu Leu Leu
                325                 330                 335
```

-continued

```
His Ala Pro Ala Thr Val Cys Gly Pro Lys Lys Ser Thr Asn Leu Val
        340                     345                 350

Lys Asn Lys Cys Val Asn Phe
    355
```